(12) United States Patent
Roell et al.

(10) Patent No.: US 12,234,285 B2
(45) Date of Patent: Feb. 25, 2025

(54) ANTIBODIES THAT BIND INTERLEUKIN-2 AND USES THEREOF

(71) Applicants: XOMA (US) LLC, Emeryville, CA (US); MUSC FOUNDATION FOR RESEARCH DEVELOPMENT, Charleston, SC (US)

(72) Inventors: Marina Roell, Berkeley, CA (US); Mark Rubinstein, Charleston, SC (US); Hassan Issafras, Emeryville, CA (US); Llewelyn Lao, San Francisco, CA (US); Ou Li, Dublin, CA (US); Daniel H. Bedinger, Pleasant Hill, CA (US); Kristin Camfield Lind, Oakland, CA (US); Agnes Choppin Holmes, Mountain View, CA (US); Toshihiko Takeuchi, Oakland, CA (US); Lauren Schwimmer, Alameda, CA (US); Hoa Giang, Alameda, CA (US); Amer M. Mirza, San Francisco, CA (US); Kirk W. Johnson, Moraga, CA (US)

(73) Assignees: XOMA (US) LLC, Emeryville, CA (US); MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 360 days.

(21) Appl. No.: 17/112,664

(22) Filed: Dec. 4, 2020

(65) Prior Publication Data
US 2021/0188969 A1 Jun. 24, 2021

Related U.S. Application Data

(62) Division of application No. 15/718,152, filed on Sep. 28, 2017, now Pat. No. 10,858,428.

(60) Provisional application No. 62/421,038, filed on Nov. 11, 2016, provisional application No. 62/401,158, filed on Sep. 28, 2016.

(51) Int. Cl.
| | | |
|---|---|---|
| C07K 16/24 | (2006.01) | |
| A61K 38/20 | (2006.01) | |
| A61K 39/395 | (2006.01) | |
| A61P 11/06 | (2006.01) | |
| A61P 31/04 | (2006.01) | |
| A61P 35/00 | (2006.01) | |
| A61P 37/06 | (2006.01) | |
| C07K 16/18 | (2006.01) | |
| C07K 16/28 | (2006.01) | |
| A61K 39/00 | (2006.01) | |
| C07K 14/55 | (2006.01) | |

(52) U.S. Cl.
CPC ........ *C07K 16/246* (2013.01); *A61K 38/2013* (2013.01); *A61K 39/395* (2013.01); *A61K 39/3955* (2013.01); *A61P 11/06* (2018.01); *A61P 31/04* (2018.01); *A61P 35/00* (2018.01); *A61P 37/06* (2018.01); *C07K 16/18* (2013.01); *C07K 16/28* (2013.01); *A61K 2039/505* (2013.01); *A61K 2039/507* (2013.01); *C07K 2317/24* (2013.01); *C07K 2317/32* (2013.01); *C07K 2317/33* (2013.01); *C07K 2317/565* (2013.01); *C07K 2317/73* (2013.01); *C07K 2317/76* (2013.01); *C07K 2317/92* (2013.01)

(58) Field of Classification Search
CPC ........ A61K 2039/505; A61K 39/39558; A61K 39/395; A61K 39/3955; A61K 39/00; C07K 2317/92; C07K 2317/76; C07K 2317/56; C07K 2317/565; C07K 16/244; C07K 16/246
See application file for complete search history.

(56) References Cited

U.S. PATENT DOCUMENTS

| | | |
|---|---|---|
| 4,179,337 A | 12/1979 | Davis et al. |
| 4,816,567 A | 3/1989 | Cabilly et al. |
| 5,057,313 A | 10/1991 | Shih et al. |
| 5,223,409 A | 6/1993 | Ladner et al. |
| 5,229,275 A | 7/1993 | Goroff |
| 5,348,867 A | 9/1994 | Georgiou et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,591,669 A | 1/1997 | Krimpenfort et al. |
| 5,624,821 A | 4/1997 | Winter et al. |
| 5,643,768 A | 7/1997 | Kawasaki |
| 5,658,754 A | 8/1997 | Kawasaki |
| 5,723,287 A | 3/1998 | Russell et al. |

(Continued)

FOREIGN PATENT DOCUMENTS

| | | |
|---|---|---|
| EP | 0404097 A2 | 12/1990 |
| WO | WO-8705330 A1 | 9/1987 |

(Continued)

OTHER PUBLICATIONS

Abbas, A. The surprising story of IL-2. From experimental models to clinical application. Am J Pathol 190(9): 1776-1781, 2020.*

(Continued)

*Primary Examiner* — Bridget E Bunner
(74) *Attorney, Agent, or Firm* — MARSHALL, GERSTEIN & BORUN LLP

(57) ABSTRACT

The present disclosure relates, in general, to human antibodies against human interleukin 2 (IL-2) and methods of use of such antibodies for modulating IL-2 activity and use in the treatment of conditions such as cancer, autoimmune disease, or infection.

14 Claims, 26 Drawing Sheets
Specification includes a Sequence Listing.

(56) References Cited

U.S. PATENT DOCUMENTS

| | | | |
|---|---|---|---|
| 5,766,886 | A | 6/1998 | Studnicka et al. |
| 5,770,429 | A | 6/1998 | Lonberg et al. |
| 5,877,293 | A | 3/1999 | Adair et al. |
| 5,939,598 | A | 8/1999 | Kucherlapati et al. |
| 5,969,108 | A | 10/1999 | McCafferty et al. |
| 6,054,287 | A | 4/2000 | Gao et al. |
| 6,091,001 | A | 7/2000 | Jakobovits et al. |
| 6,114,598 | A | 9/2000 | Kucherlapati et al. |
| 6,194,551 | B1 | 2/2001 | Idusogie et al. |
| 6,657,103 | B1 | 12/2003 | Kucherlapati et al. |
| 6,699,658 | B1 | 3/2004 | Wittrup et al. |
| 6,737,056 | B1 | 5/2004 | Presta |
| 6,833,268 | B1 | 12/2004 | Green et al. |
| 8,569,462 | B2 | 10/2013 | Bedinger et al. |
| 8,759,486 | B2 | 6/2014 | Leon Monzon et al. |
| 9,266,938 | B2 | 2/2016 | Ast et al. |
| 10,858,428 | B2 * | 12/2020 | Roell ............. A61P 31/04 |
| 2002/0004215 | A1 | 1/2002 | Osbourn et al. |
| 2002/0199213 | A1 | 12/2002 | Tomizuka et al. |
| 2003/0028071 | A1 | 2/2003 | Handy et al. |
| 2003/0031667 | A1 | 2/2003 | Deo et al. |
| 2003/0032995 | A1 | 2/2003 | Handy et al. |
| 2003/0092125 | A1 | 5/2003 | Davis et al. |
| 2003/0118592 | A1 | 6/2003 | Ledbetter et al. |
| 2003/0133939 | A1 | 7/2003 | Ledbetter et al. |
| 2003/0190317 | A1 | 10/2003 | Baca et al. |
| 2003/0194404 | A1 | 10/2003 | Greenfeder et al. |
| 2004/0132101 | A1 | 7/2004 | Lazar et al. |
| 2005/0037421 | A1 | 2/2005 | Honda et al. |
| 2005/0136049 | A1 | 6/2005 | Ledbetter et al. |
| 2008/0317746 | A1 | 12/2008 | Bauerle et al. |
| 2010/0310501 | A1 | 12/2010 | Boyman et al. |
| 2013/0142755 | A1 | 6/2013 | Boyman et al. |
| 2017/0114130 | A1 | 4/2017 | Rondon et al. |
| 2017/0183403 | A1 | 6/2017 | Boyman et al. |
| 2019/0016797 | A1 | 1/2019 | Arenas-Ramirez et al. |

FOREIGN PATENT DOCUMENTS

| | | |
|---|---|---|
| WO | WO-91/00906 A1 | 1/1991 |
| WO | WO-91/017271 A1 | 11/1991 |
| WO | WO-92/01047 A1 | 1/1992 |
| WO | WO-92/009690 A2 | 6/1992 |
| WO | WO-92/015679 A1 | 9/1992 |
| WO | WO-92/018619 A1 | 10/1992 |
| WO | WO-92/020791 A1 | 11/1992 |
| WO | WO-93/001288 A1 | 1/1993 |
| WO | WO-93/11161 A1 | 6/1993 |
| WO | WO-94/02602 A1 | 2/1994 |
| WO | WO-96/11953 A1 | 4/1996 |
| WO | WO-96/030498 A1 | 10/1996 |
| WO | WO-96/33735 A1 | 10/1996 |
| WO | WO-96/34096 A1 | 10/1996 |
| WO | WO-1998/024893 A2 | 6/1998 |
| WO | WO-03/041600 A1 | 5/2003 |
| WO | WO-2006/128690 A1 | 12/2006 |
| WO | WO-2006/128960 A1 | 12/2006 |
| WO | WO-2007/095643 A2 | 8/2007 |
| WO | WO-2008/003473 A2 | 1/2008 |
| WO | WO-2012/065086 A1 | 5/2012 |
| WO | WO-2013/177187 A2 | 11/2013 |
| WO | WO-2014/100014 A1 | 6/2014 |
| WO | WO-2014/108748 A1 | 7/2014 |
| WO | WO-2015/109212 A1 | 7/2015 |
| WO | WO-2015/118016 A1 | 8/2015 |
| WO | WO-2015/164815 A1 | 10/2015 |
| WO | WO-2016/005950 A1 | 1/2016 |
| WO | WO-2016/022671 A1 | 2/2016 |
| WO | WO-2016/030350 A1 | 3/2016 |

OTHER PUBLICATIONS

Gaffen et al. Overview of interleukin-2 function, production and clinical applications. Cytokine 28: 109-123, 2004.*

Kamimura et al. IL-2 in vivo activities and antitumor efficacy enhanced by an anti-IL-2 mAb. J Immunol 177(1): 306-314, 2006.*

Katzman et al. Opposing functions of IL-2 and IL-7 in the regulation of immune responses. Cytokine 56: 116-121, 2011.*

Klatzmann et al. The promise of low-dose interleukin-2 therapy for autoimmune and inflammatory diseases. Nature Rev 15: 283-294, 2015.*

Lieberman et al. The IL-2 defect in systemic lupus erythematosus disease has an expansive effect on host immunity. J Biomed Biotechnol vol. 2010: 740619 (2010) (6 total pages).*

Vasudevan et al. A single amino acid change in the binding pocket alters specificity of an anti-integrin antibody AP7.4 as revealed by its crystal structure. Blood Cells Mol Dis 32: 176-181, 2004.*

Zhang et al. Comprehensive optimization of a single-chain variable domain antibody fragment as a targeting ligand for a cytotoxic nanoparticle. mAbs 7(1): 42-52, 2014.*

Brown et al., Tolerance of single, but not multiple, amino acid replacements in antibody VH CDR 2: a means of minimizing B cell wastage from somatic hypermutation?, J. Immunol., 156(9):3285-91 (May 1996).

Igawa et al., Engineering the variable region of therapeutic IgG antibodies, MAbs, 3(3):243-52 (2011).

Jibi (Otorhinolaryngology), 2014, 60 (Supplement 1), S63-S69.

Japanese Patent Application No. 2019-538102, Notice of Reasons for Rejection, mailed Aug. 11, 2021.

Amstutz et al., In vitro display technologies: novel developments and applications, Curr. Opin. Biotechnol., 12(4):400-5 (2001).

Aplin et al., Preparation, properties, and applications of carbohydrate conjugates of proteins and lipids, CRC Crit. Rev. Biochem., 10(4):259-306 (1981).

Arenas-Ramirez et al., Interleukin-2: Biology, Design and Application, Trends Immunol., 36(12):763-77 (2015).

Bachmann et al., Interleukin 2: from immunostimulation to immunoregulation and back again, EMBO Rep., 8(12):1142-8 (2007).

Barbas et al., Assembly of combinatorial antibody libraries on phage surfaces: the gene III site, Proc. Natl. Acad. Sci. USA, 88(18):7978-82 (1991).

Bayer et al., The avidin-biotin complex in affinity cytochemistry, Methods Enzymol., 62:308-15 (1979).

Bergamaschi et al., Intracellular interaction of interleukin-15 with its receptor alpha during production leads to mutual stabilization and increased bioactivity, J. Biol. Chem., 283(7):4189-99 (2008).

Better et al., Escherichia coli secretion of an active chimeric antibody fragment. Science. 240: 1041-3 (1988).

Better et al., Potent anti-CD5 ricin A chain immunoconjugates from bacterially produced Fab' and F(ab')2. Proc. Natl. Acad. Sci. USA. 90: 457-61 (1993).

Biocca et al., Expression and targeting of intracellular antibodies in mammalian cells, EMBO J., 9(1):101-8 (1990).

Bird et al., Single-chain antigen-binding proteins, Science, 242(4877):423-6 (1988).

Boulianne et al., Production of functional chimaeric mouse/human antibody, Nature, 312(5995):643-6 (1984).

Boyman et al., Selective stimulation of T cell subsets with antibody-cytokine immune complexes, Science, 311(5769):1924-7 (2006).

Boyman et al., The role of interleukin-2 during homeostasis and activation of the immune system, Nat. Rev. Immunol., 12(3):180-90 (2012).

Brorson et al. Mutational analysis of avidity and fine specificity of anti-levan antibodies. J Immunol 163: 6694-6701, 1999.

Bruggermann et al., Designer mice: the production of human antibody repertoires in transgenic animals, Year Immunol., 7:33-40 (1993).

Brummell et al. Probing the combining site of an anti-carbohydrate antibody by saturation-mutagenesis: role of the heavy-chain CDR3 residues. Biochem 32(4): 1180-1187, 1993 (abstract).

Burks et al. In vitro scanning saturation mutagenesis of an antibody binding pocket. Proc Natl Acad Sci USA 94: 412-417, 1997.

Burton et al., Human antibodies from combinatorial libraries, Adv. Immunol., 57:191-280 (1994).

Carmenate et al., Human IL-2 mutein with higher antitumor efficacy than wild type IL-2, J. Immunol., 190(12):6230-8 (2013).

(56) References Cited

OTHER PUBLICATIONS

Caron et al., Engineered humanized dimeric forms of IgG are more effective antibodies, J. Exp. Med., 176(4):1191-5 (1992).
Carter et al., High level *Escherichia coli* expression and production of a bivalent humanized antibody fragment. *Bio/Technology* 10: 163-7 (1992).
Cassett et al. A peptide mimetic of an anti-CD4 monoclonal antibody by rationale design. Biochem Biophys Res Comm 307: 198205, 2003.
Charych et al., NKTR-214, an Engineered Cytokine with Biased IL2 Receptor Binding, Increased Tumor Exposure, and Marked Efficacy in Mouse Tumor Models, Clin. Cancer Res., 22(3):680-90 (2016).
Chen et al., Selection and analysis of an optimized anti-VEGF antibody: crystal structure of an affinity-matured Fab in complex with antigen, J Mol Biol., 293: 865-881, 1999.
Chothia et al., Canonical structures for the hypervariable regions of immunoglobulins, J. Mol. Biol., 196(4):901-17 (1987).
Chothia et al., Conformations of immunoglobulin hypervariable regions, Nature, 342(6252):877-83 (1989).
Clackson et al., In vitro selection from protein and peptide libraries, Trends Biotechnol., 12(5):173-84 (1994).
Clackson et al., Making antibody fragments using phage display libraries, Nature, 352(6336):624-8 (1991).
Co et al., A humanized antibody specific for the platelet integrin gpIIb/IIIa, J. Immunol., 152)6):2968-76 (1994).
Colby et al., Potent inhibition of huntingtin aggregation and cytotoxicity by a disulfide bond-free single-domain intracellular antibody, Proc. Natl. Acad. Sci. USA, 101(51):17616-21 (2004).
Colman, Effects of amino acid sequence changes on antibody-antigen interactions, Res Immunol. 145:33-36, 1994.
Conrath et al., Beta-lactamase inhibitors derived from single-domain antibody fragments elicited in the camelidae, Antimicro. Agents Chemother., 45(10):2807-12 (2001).
Cortez-Retamozo et al., Efficient cancer therapy with a nanobody-based conjugate, Cancer Res., 64(8):2853-7 (2004).
De Pascalis et al. Grafting and "abbreviated" complementarity-determining regions containing specificity-determining residues essential for ligand contact to engineer a less immunogenic humanized monoclonal antibody. J Immunol 169: 3076-3084, 2002.
Desmyter et al., Antigen specificity and high affinity binding provided by one single loop of a camel single-domain antibody, J. Biol. Chem., 276(28):26285-90 (2001).
Downie et al., Interleukin-2 directly increases albumin permeability of bovine and human vascular endothelium in vitro, Am. J. Respir. Cell Mol. Biol., 7(1):58-65 (1992).
Dutcher et al., High dose interleukin-2 (Aldesleukin)—expert consensus on best management practices-2014, J. Immunother. Cancer, 2:26 (2014).
Edge et al., Deglycosylation of glycoproteins by trifluoromethanesulfonic acid, Anal. Biochem., 118(1):131-7 (1981).
Engvall et al., Enzyme-linked immunosorbent assay, Elisa. 3. Quantitation of specific antibodies by enzyme-labeled anti-immunoglobulin in antigen-coated tubes, J. Immunol., 109(1):129-35 (1972).
Ewert et al., Biophysical properties of camelid V(HH) domains compared to those of human V(H)3 domains, Biochemistry, 41(11):3628-36 (2002).
Eyer et al., Single-domain antibody fragments derived from heavy-chain antibodies: a review, Veterinarni Medicina, 57:439-513 (2012).
Ferrara et al., Modulation of therapeutic antibody effector functions by glycosylation engineering: influence of Golgi enzyme localization domain and co-expression of heterologous beta1, 4-N-acetylglucosaminyltransferase III and Golgi alpha-mannosidase II, Biotechnol. Bioeng., 93(5):851-61 (2006).
Fishwild et al., High-avidity human IgG kappa monoclonal antibodies from a novel strain of minilocus transgenic mice, Nat. Biotechnol., 14(7):845-51 (1996).
Fix, Strategies for delivery of peptides utilizing absorption-enhancing agents, J. Pharm. Sci., 85(12):1282-5 (1996).
Fuchs et al., Targeting recombinant antibodies to the surface of *Escherichia coli*: fusion to a peptidoglycan associated lipoprotein, Bio/Technology, 9:1369-73 (Dec. 1991).
Garcia-Martinez et al., Modeling the role of IL2 in the interplay between CD4+ helper and regulatory T cells: studying the impact of IL2 modulation therapies, Int. Immunol., 24(7):427-46 (2012).
Garrard et al., Fab assembly and enrichment in a monovalent phage display system, Bio/Technology, 9(12):1373-7 (1991).
Gaston et al., Production of bioactive soluble interleukin-15 in complex with interleukin-15 receptor alpha from a conditionally-replicating oncolytic HSV-1, PLoS One, 8(11):e81768 (2013).
Goding, Conjugation of antibodies with fluorochromes: modifications to the standard methods, J. Immunol. Methods, 13(3-4):215-26 (1976).
Goding, Production of monoclonal antibodies, pp. 59-103, IN: Monoclonal Antibodies: Principles and Practice, 2nd edition, Academic Press (1986).
Gram et al., In vitro selection and affinity maturation of antibodies from a naive combinatorial immunoglobulin library, Proc. Natl. Acad. Sci. USA, 89(8):3576-80 (1992).
Green et al., Transgenic mouse strains as platforms for the successful discovery and development of human therapeutic monoclonal antibodies, Curr. Drug Discov. Technol., 11(1):74-84 (2014).
Greenberg et al., A new antigen receptor gene family that undergoes rearrangement and extensive somatic diversification in sharks, Nature, 374(6518):168-73 (1995).
Griffiths et al., Human anti-self antibodies with high specificity from phage display libraries, EMBO J., 12(2):725-34 (1993).
Guss et al., Structure of the IgG-binding regions of streptococcal protein G. *EMBO* 5: 1567-75 (1986).
Haji-Fataliha et al., CAR-modified T-cell therapy for cancer: an updated review, Artif. Cells Nanomed. Biotechnol., 44(16):1339-49 (2016).
Hakimuddin et al., A chemical method for the deglycosylation of proteins, *Arch. Biochem. Biophys.* 259:52-7 (1987).
Hamers-Casterman et al., Naturally occurring antibodies devoid of light chains, Nature, 363(6428):446-8 (1993).
Hanes et al., In vitro selection and evolution of functional proteins by using ribosome display, Proc. Natl. Acad. Sci. USA, 94(10):4937-42 (1997).
Harlow et al. (eds.), Antibodies: A Laboratory Manual, Cold Spring Harbor Laboratory (1988).
Hay et al., Bacteriophage cloning and *Escherichia coli* expression of a human IgM Fab, Hum. Antibodies Hybridomas, 3(2):81-5 (1992).
Heng et al., Making cell-permeable antibodies (Transbody) through fusion of protein transduction domains (PTD) with single chain variable fragment (scFv) antibodies: potential advantages over antibodies expressed within the intracellular environment (Intrabody), Med. Hypotheses, 64(6):1105-8 (2005).
Holliger et al., "Diabodies": small bivalent and bispecific antibody fragments, Proc. Natl. Acad. Sci. USA, 90(14):6444-8 (1993).
Holliger et al., Engineered antibody fragments and the rise of single domains, Nat. Biotechnol., 23(9):1126-36 (2005).
Holm et al. Functional mapping and single chain construction of the anti-cytokeratin 8 monoclonal antibody TS1. Mol Immunol 44: 1075-1084, 2007.
Hoogenboom et al., By-passing immunisation. Human antibodies from synthetic repertoires of germline VH gene segments rearranged in vitro, J. Mol. Biol., 227(2):381-8 (1992).
Hoogenboom et al., Multi-subunit proteins on the surface of filamentous phage: methodologies for displaying antibody (Fab) heavy and light chains, Nucleic Acids Res., 19(15):413-7 (1991).
Huse et al., Generation of a large combinatorial library of the immunoglobulin repertoire in phage lambda, Science. 246:1275-81 (1989).
Huston et al., Protein engineering of antibody binding sites: recovery of specific activity in an anti-digoxin single-chain Fv analogue produced in *Escherichia coli*, Proc. Natl. Acad. Sci. USA, 85(16):5879-83 (1988).
International Application No. PCT/US2017/053880, International Search Report and Written Opinion, mailed May 4, 2018.

(56) References Cited

OTHER PUBLICATIONS

Ishida et al., Production of human monoclonal and polyclonal antibodies in TransChromo animals, Cloning Stem Cells, 4(1):91-102 (2002).
Jakobovits et al., Analysis of homozygous mutant chimeric mice: deletion of the immunoglobulin heavy-chain joining region blocks B-cell development and antibody production, Proc. Natl. Acad. Sci. USA, 90(6):2551-5 (1993).
Jakobovits et al., Germ-line transmission and expression of a human-derived yeast artificial chromosome, Nature, 362(6417):255-8 (1993).
Jang et al. The structural basis for DNA binding by an anti-DNA autobody. Mol Immunol 35: 1207-1217, 1998.
Jespers et al., Guiding the selection of human antibodies from phage display repertoires to a single epitope of an antigen, Biotechnology (N.Y.), 12(9):899-903 (1994).
Jones et al., Replacing the complementarity-determining regions in a human antibody with those from a mouse, Nature, 321(6069):522-5 (1986).
Kabat et al., Sequences of Proteins of Immunological Interest, 4th edition, US Department of Health and Human Services (1987).
Kabat et al., Sequences of Proteins of Immunological Interest, vol. 1, 5th edition, U.S. Department of Health and Human Services (1991).
Kang et al., Antibody redesign by chain shuffling from random combinatorial immunoglobulin libraries, Proc. Natl. Acad. Sci. USA, 88(24):11120-3 (1991).
Kettleborough et al., Humanization of a mouse monoclonal antibody by CDR-grafting: the importance of framework residues on loop conformation, Protein Eng., 4(7):773-83 (1991).
Kobayashi et al. Tryptophan H33 plays an important role in pyrimidine (6-4) pyrimidone photoproduct binding by a high-affinity antibody. Protein Engineering 12(10): 879-884, 1999.
Kohler et al., Continuous cultures of fused cells secreting antibody of predefined specificity, Nature, 256(5517):495-7 (1975).
Krieg et al., Improved IL-2 immunotherapy by selective stimulation of IL-2 receptors on lymphocytes and endothelial cells, Proc. Natl. Acad. Sci. USA, 107(26):11906-11 (2010).
Laurent et al., T-cell activation by treatment of cancer patients with EMD 521873 (Selectikine), an IL-2/anti-DNA fusion protein, J. Transl. Med., 11:5 (2013).
Lee et al., Complete humanization of the mouse immunoglobulin loci enables efficient therapeutic antibody discovery, Nat. Biotechnol., 32(4):356-63 (2014).
Lee et al., Microbial cell-surface display, Trends Biotechnol., 21(1):45-52 (2003).
Lee et al., The application of transgenic mice for therapeutic antibody discovery, Methods Mol. Biol., 901:137-48 (2012).
Lefranc et al., IMGT unique numbering for immunoglobulin and T cell receptor variable domains and Ig superfamily V-like domains, Dev. Comp. Immunol., 27(1):55-77 (2003).
Lefranc, The IMGT unique numbering for immunoglobulins, t-cell receptors, and Ig-like domains, The Immunologist, 7/4:132-6 (1999).
Levin et al., Exploiting a natural conformational switch to engineer an interleukin-2 'superkine', Nature, 484(7395):529-33 (2012).
Lindmark et al., Binding of immunoglobulins to protein A and immunoglobulin levels in mammalian sera. *J. Immunol. Meth.* 62: 1-13 (1983).
Létourneau et al., IL-2/anti-IL-2 antibody complexes show strong biological activity by avoiding interaction with IL-2 receptor alpha subunit CD25, Proc. Natl. Acad. Sci. USA, 107(5):2171-6 (2010).
MacCallum et al. Antibody-antigen interactions: contact analysis and binding site topography. J Mol Biol 262: 732-745, 1996.
Malek et al., The biology of interleukin-2, Annu. Rev. Immunol., 26:453-79 (2008).
Marks et al., By-passing immunization. Human antibodies from V-gene libraries displayed on phage, J. Mol. Biol., 222(3):581-97 (1991).
Marks et al., By-passing immunization: building high affinity human antibodies by chain shuffling, Biotechnology (N.Y.), 10(7):779-83 (1992).
Mather et al., Culture of testicular cells in hormone-supplemented serum-free medium. *Annals N.Y. Acad. Sci.* 383: 44-68 (1982).
Mather, Establishment and characterization of two distinct mouse testicular epithelial cell lines. *Biol. Reprod.* 23: 243-251 (1980).
McCafferty et al., Phage antibodies: filamentous phage displaying antibody variable domains, Nature, 348(6301):552-4 (1990).
Mhashilkar et al., Inhibition of HIV-1 Tat-mediated LTR transactivation and HIV-1 infection by anti-Tat single chain intrabodies, EMBO J., 14(7):1542-51 (1995).
Mitra et al., Interleukin-2 activity can be fine tuned with engineered receptor signaling clamps, Immunity, 42(5):826-38 (2015).
Morrison et al., Chimeric human antibody molecules: mouse antigen-binding domains with human constant region domains, Proc. Natl. Acad. Sci. USA, 81(21):6851-5 (1984).
Morrison et al., Genetically engineered antibody molecules, Adv. Immunol., 44:65-92 (1989).
Nayar et al., Extending the lifespan and efficacies of immune cells used in adoptive transfer for cancer immunotherapies-A review, Oncoimmunology, 4(4):e1002720 (2015).
Nguyen et al., The specific variable domain of camel heavy-chain antibodies is encoded in the germline, J. Mol. Biol., 275(3):413-8 (1998).
Niwa et al., The current status and prospects of antibody engineering for therapeutic use: focus on glycoengineering technology, J. Pharm. Sci., 104(3):930-41 (2015).
Nuttall et al., Isolation of the new antigen receptor from wobbegong sharks, and use as a scaffold for the display of protein loop libraries, Mol. Immunol., 38(4):313-26 (2001).
Olafsen et al., Characterization of engineered anti-p185HER-2 (scFv-CH3)2 antibody fragments (minibodies) for tumor targeting, Protein Eng. Des. Sel., 17(4):315-23 (2004).
Oliyai et al., Prodrugs of peptides and proteins for improved formulation and delivery, Annu. Rev. Pharmacol. Toxicol., 33:521-44 (1993).
Omidfar et al., Advances in phage display technology for drug discovery, Expert Opin. Drug Discov., 10(6):651-69 (2015).
Padlan, A possible procedure for reducing the immunogenicity of antibody variable domains while preserving their ligand-binding properties, Mol. Immunol., 28(4-5):489-98 (1991).
Padlan, Anatomy of the antibody molecule, Mol. Immunol., 31(3):169-217 (1994).
Paul, Fundamental Immunology, 3rd Edition, Raven Press, New York, Chapt. 8, pp. 292-295 (1993).
Poljak, Production and structure of diabodies, Structure, 2(12):1121-3 (1994).
Presta et al., Engineering therapeutic antibodies for improved function, Biochem. Soc. Trans., 30(4):487-90 (2002).
Rafi-Janajreh et al., Evidence for the involvement of CD44 in endothelial cell injury and induction of vascular leak syndrome by IL-2, J. Immunol., 163(3):1619-27 (1999).
Raju et al., Terminal sugars of Fc glycans influence antibody effector functions of IgGs, Curr. Opin. Immunol., 20(4):471-8 (2008).
Reichman et al., Single domain antibodies: comparison of camel VH and camelised human VH domains, J. Immunol. Methods, 231:25-38 (1999).
Revets et al., Nanobodies as novel agents for cancer therapy, Expert Opin. Biol. Ther., 5(1):111-24 (2005).
Riechmann et al., Reshaping human antibodies for therapy, Nature, 332(6162):323-7 (1988).
Rojas et al., Deciphering the molecular bases of the biological effects of antibodies against Interleukin-2: a versatile platform for fine epitope mapping, Immunobiology, 218(1):105-13 (2013).
Rosenberg, IL-2: the first effective immunotherapy for human cancer, J. Immunol., 192(12):5451-8 (2014).
Rothman et al., Antibody-dependent cytotoxicity mediated by natural killer cells is enhanced by castanospermine-induced alterations of IgG glycosylation, Mol. Immunol., 26(12):1113-23 (1989).

(56) References Cited

OTHER PUBLICATIONS

Rubinstein et al., Novel IL-2/mAb complexes mediate potent antitumor immunity which is augmented with anti-PD-1 mAb therapy, Abstract No. P15, J. Immuno Therapy of Cancer, 4(Suppl 2):91 (2016).
Rudikoff et al., Single amino acid substitution altering antigen-binding specificity, *Proc. Natl. Acad. Sci. USA* 79: 1979-1983 (1982).
Safdari et al., Antibody humanization methods—a review and update, Biotechnol. Genet. Eng. Rev., 29:175-86 (2013).
Sanger et al., DNA sequencing with chain-terminating inhibitors, Proc. Natl. Acad. Sci. USA, 74(12):5463-7 (1977).
Sarmay et al., Mapping and comparison of the interaction sites on the Fc region of IgG responsible for triggering antibody dependent cellular cytotoxicity (ADCC) through different types of human Fc gamma receptor, Mol. Immunol., 29(5):633-9 (1992).
Schoonjans et al., Fab chains as an efficient heterodimerization scaffold for the production of recombinant bispecific and trispecific antibody derivatives, J. Immunol., 165(12):7050-7 (2000).
Sergeeva et al., Display technologies: application for the discovery of drug and gene delivery agents, Adv. Drug Deliv. Rev., 58(15):1622-54 (2006).
Shanafelt et al., A T-cell-selective interleukin 2 mutein exhibits potent antitumor activity and is well tolerated in vivo, Nat. Biotechnol., 18(11):1197-202 (2000).
Shields et al., Lack of fucose on human IgG1 N-linked oligosaccharide improves binding to human Fcgamma RIII and antibody-dependent cellular toxicity, J. Biol. Chem., 277(30):26733-40 (2002).
Shih et al., A fluorouridine-anti-CEA immunoconjugate is therapeutically effective in a human colonic cancer xenograft model, Int. J. Cancer, 46(6):1101-6 (1990).
Shih et al., Site-specific linkage of methotrexate to monoclonal antibodies using an intermediate carrier, Int. J. Cancer, 41(6):832-9 (1988).
Shinkawa et al., The absence of fucose but not the presence of galactose or bisecting N-acetylglucosamine of human IgG1 complex-type oligosaccharides shows the critical role of enhancing antibody-dependent cellular cytotoxicity, J. Biol. Chem., 278(5):3466-73 (2003).
Shopes et al., A genetically engineered human IgG mutant with enhanced cytolytic activity, J. Immunol., 148(9):2918-22 (1992).
Spangler et al., Antibodies to Interleukin-2 Elicit Selective T Cell Subset Potentiation through Distinct Conformational Mechanisms, Immunity, 42(5):815-25 (2015).
Stech et al., Cell-Free Synthesis Meets Antibody Production: A Review, Antibodies, 4(1):12-33 (2015).
Sternberger et al., The unlabeled antibody enzyme method of immunohistochemistry: preparation and properties of soluble antigen-antibody complex (horseradish peroxidase-antihorseradish peroxidase) and its use in identification of spirochetes, J. Histochem. Cytochem., 18(5):315-33 (1970).
Stevenson et al., A chimeric antibody with dual Fc regions (bisFabFc) prepared by manipulations at the IgG hinge, Anticancer Drug Des., 3(4):219-30 (1989).
Studnicka et al., Human-engineered monoclonal antibodies retain full specific binding activity by preserving non-CDR complementarity-modulating residues, Protein Eng., 7(6):805-14 (1994).
Su et al., IL-2Ra mediates temporal regulation of IL-2 signaling and enhances immunotherapy, Sci. Transl. Med., 7(311):311ra170 (2015).

Sugimoto et al., The therapeutic potential of a novel PSMA antibody and its IL-2 conjugate in prostate cancer, Anticancer Res., 34(1):89-97 (2014).
Thotakura et al., Enzymatic deglycosylation of glycoproteins, *Methods Enzymol.* 138:350-9 (1987).
Tomala et al., Chimera of IL-2 linked to light chain of anti-IL-2 mAb mimics IL-2/anti-IL-2 mAb complexes both structurally and functionally, ACS Chem. Biol., 8(5):871-6 (2013).
Tomala et al., IL-2/anti-IL-2 mAb immunocomplexes: A renascence of IL-2 in cancer immunotherapy?, Oncoimmunology 5(3):e1102829 (2015).
Umana et al., Engineered glycoforms of an antineuroblastoma IgG1 with optimized antibody-dependent cellular cytotoxic activity, Nat. Biotechnol., 17(2):176-80 (1999).
Urlaub et al., Isolation of Chinese hamster cell mutants deficient in dihydrofolate reductase activity. *Proc. Natl. Acad. Sci. USA* . 77: 4216-20 (1980).
Vajdos et al., Comprehensive functional maps of the antigen-binding site of an anti-ErbB2 antibody obtained with shotgun scanning mutagenesis, *J. Mol. Biol.* 320:415-428 (2002).
Verhoeyen et al., Reshaping human antibodies: grafting an antilysozyme activity, Science, 239(4847):1534-6 (1988).
Waldmann, The contrasting roles of IL-2 and IL-15 in the life and death of lymphocytes: implications for the immunotherapy of rheumatological diseases, Arthritis Res., Suppl 3:S161-7 (2002).
Wang et al., Structural biology of shared cytokine receptors, Annu. Rev. Immunol., 27:29-60 (2009).
Ward et al., Binding activities of a repertoire of single immunoglobulin variable domains secreted from *Escherichia coli*, Nature, 341(6242):544-6 (1989).
Wheeler et al., Intrabody-based strategies for inhibition of vascular endothelial growth factor receptor-2: effects on apoptosis, cell growth, and angiogenesis, FASEB J., 17(12):1733-5 (2003).
Willems et al., Optimizing expression and purification from cell culture medium of trispecific recombinant antibody derivatives, J. Chromatogr. B Analyt. Technol. Biomed. Life Sci., 786(1-2):161-76 (2003).
Winter et al., Making antibodies by phage display technology, Annu. Rev. Immunol., 12:433-55 (1994).
Wittrup, Protein engineering by cell-surface display, Curr. Opin. Biotechnol., 12(4):395-9 (2001).
Wolff et al., Monoclonal antibody homodimers: enhanced antitumor activity in nude mice, Cancer Res., 53(11):2560-5 (1993).
Wu et al. Humanization of a murine monoclonal antibody by simultaneous optimization of framework and CDR residues. J Mol Biol 294: 151-162, 1999.
Wu et al., Fab-based bispecific antibody formats with robust biophysical properties and biological activity, MAbs, 7(3):470-82 (2015).
Yamane-Ohnuki et al., Establishment of FUT8 knockout Chinese hamster ovary cells: an ideal host cell line for producing completely defucosylated antibodies with enhanced antibody-dependent cellular cytotoxicity, Biotechnol. Bioeng., 87(5):614-22 (2004).
Yu et al., Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells, Int. J. Cancer, 56(2):244-8 (1994).

\* cited by examiner

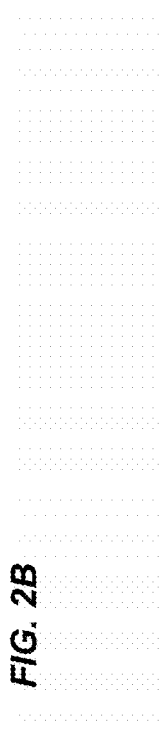
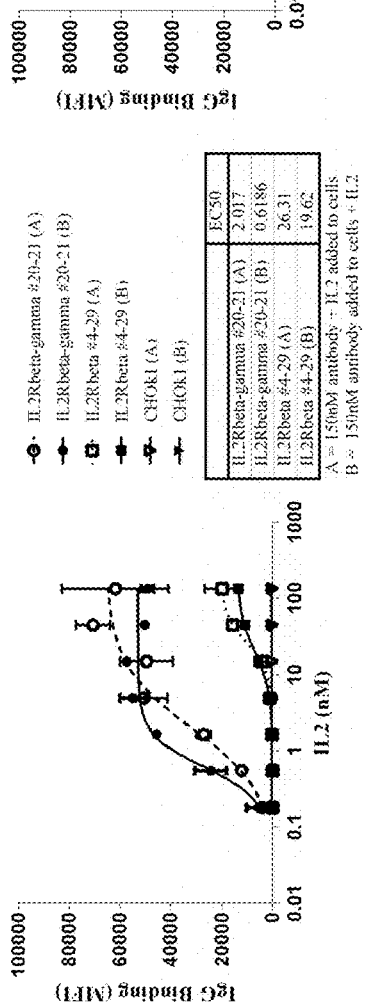
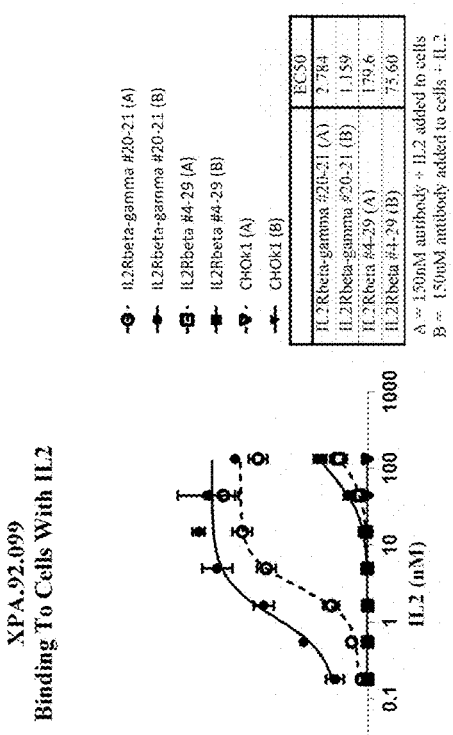
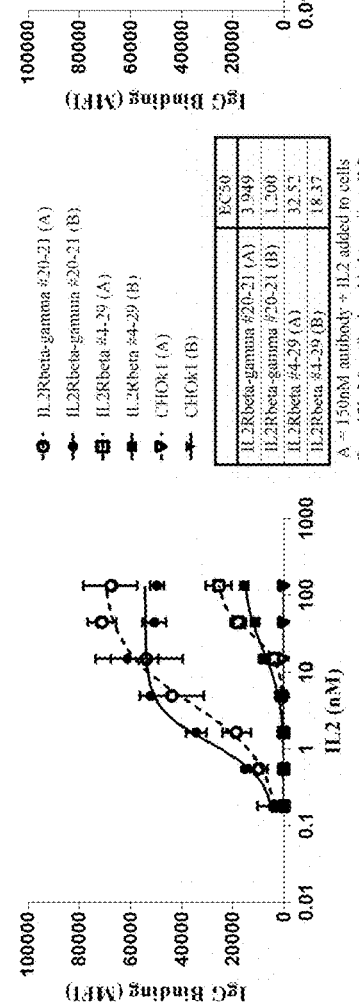
FIG. 2A — XPA.92.019 Binding To Cells With IL2
FIG. 2B — XPA.92.041 Binding To Cells With IL2
FIG. 2C — XPA.92.042 Binding To Cells With IL2
FIG. 2D — XPA.92.099 Binding To Cells With IL2

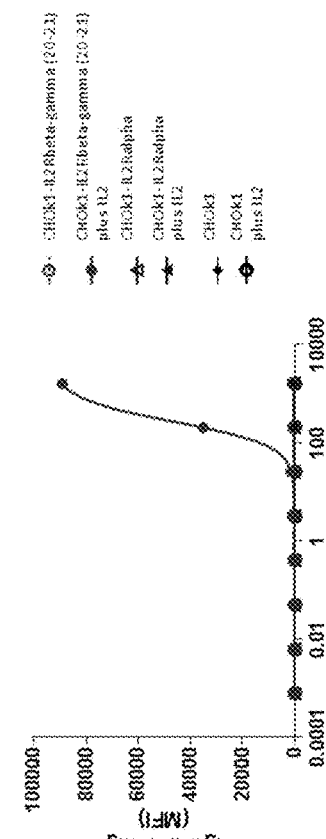
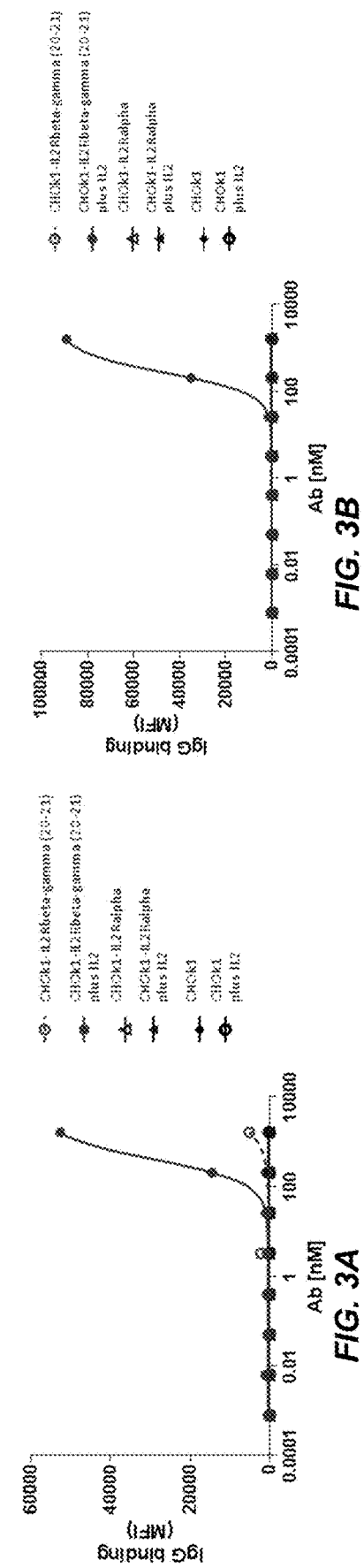
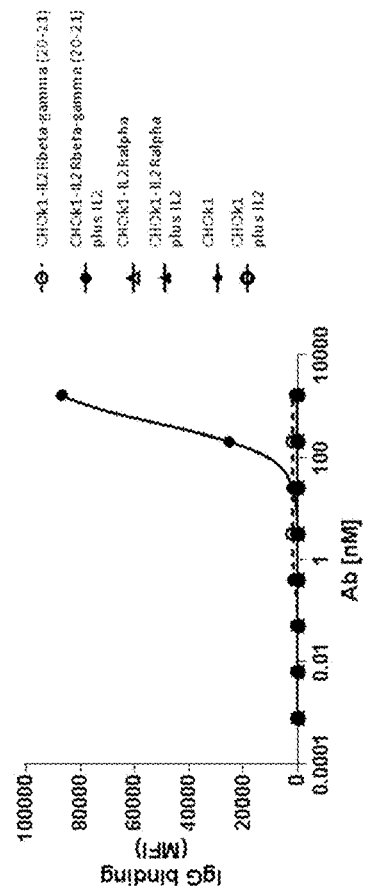
FIG. 3A
FIG. 3B
FIG. 3C

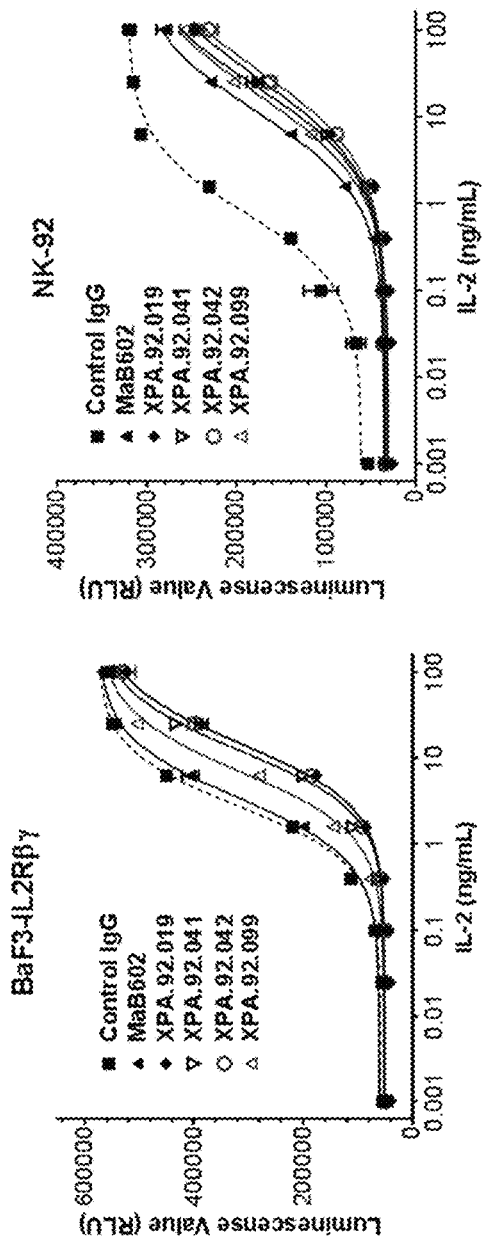
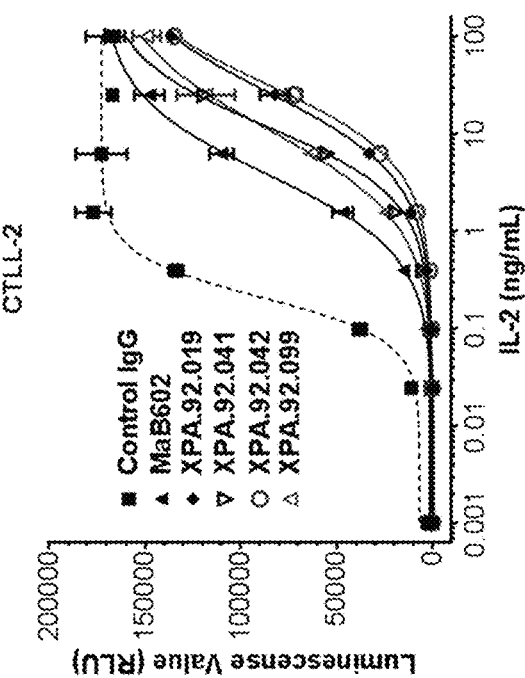
FIG. 4A
FIG. 4B
FIG. 4C

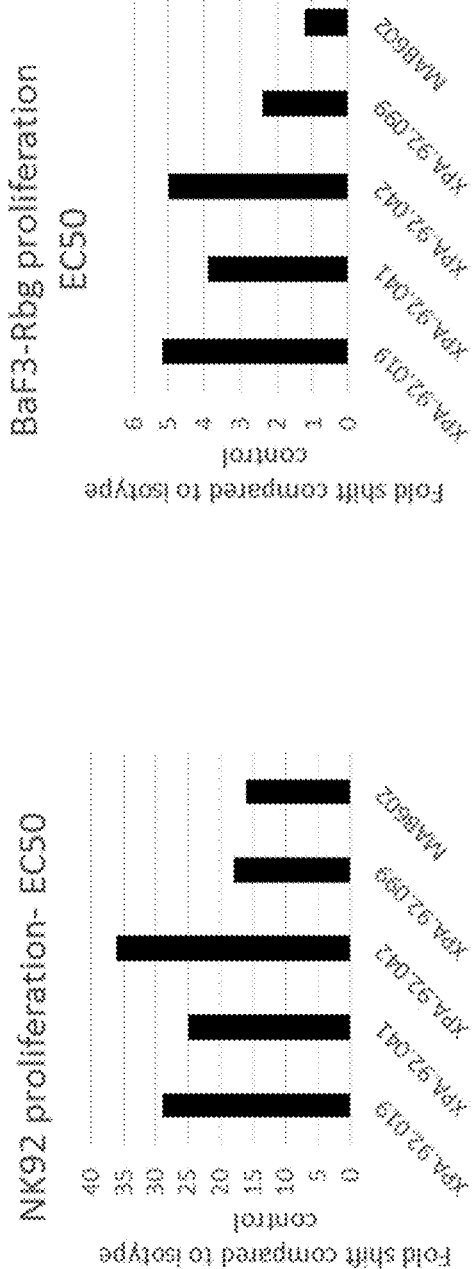
FIG. 5B
FIG. 5A
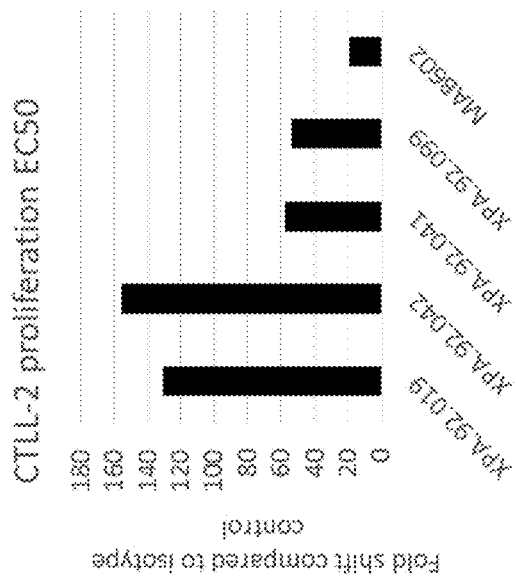
FIG. 5C

Interleukin-2 sequence alignments

```
                            1                                                                           73
                            |                                                                           |
SEQ ID NO: 50 mouse           EAQQQQQQQQQQQ  insertion in mouse sequence only
SEQ ID NO: 51 rat           ...............
SEQ ID NO: 52 human         .........SSSTA.H..Q..M..EL.SRME.....R.L..P.......L..Q......D..GP.RH..D.T
SEQ ID NO: 53 rabbit        .........PA.E.Q.H..Q.......VL.R.D.....L.PM.......L..Q......N..GA.QR..D.T
SEQ ID NO: 54 pig           APTSSSSTKKTQL.QLEHLLLDLQMILNGINNYKNPKLTRMLTFKFYMPKKATELKHLQCLEEELKPLEEVLNLA
                            ..............E..E......DQ........VL.K.V.D.......S..S......V.................
                            ..............N.KK......P.........LL.KEVK........E.AD.S.....Q...........A..G 74                                                                          133
                            |                                                                           |
mouse                       ...S.Q..EDAENE.......R.T.VK........DN....................S..V.D...R..A.......SPQ
rat                         ...............................T.VK........NK.E.QFD..P..V.....R...AI........M.Q
human                       QSKNFHL-RPRDLISNINVIVLELKGSETTFMQEYADETATIVEFLNRWITFCQSIISTLT
rabbit                      G..S.GGNT.ES.......T..K...........-.........V...........................ASSS
pig                         G..SDSANIKESMN.......T..........S.K.........D..V.A..........K...........Y
```

IL-2 Rα binding regions

FIG. 6

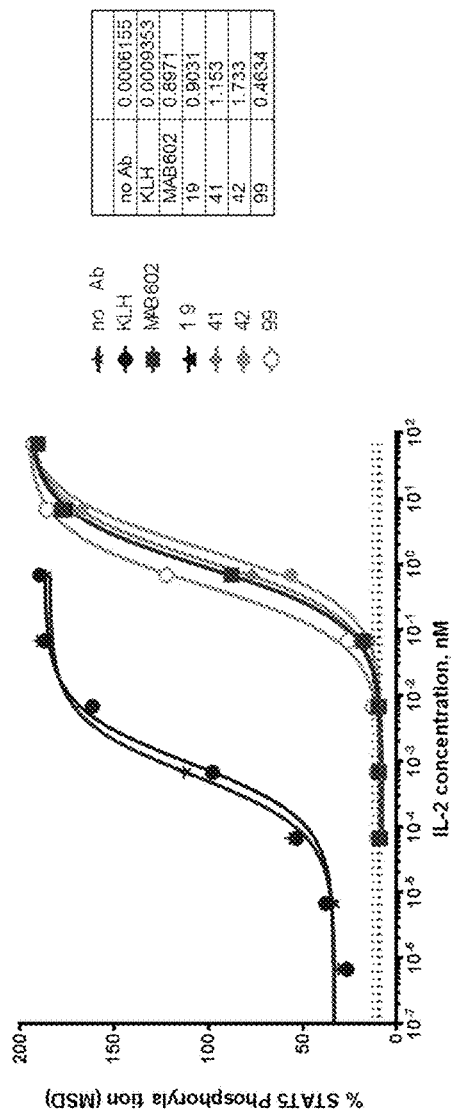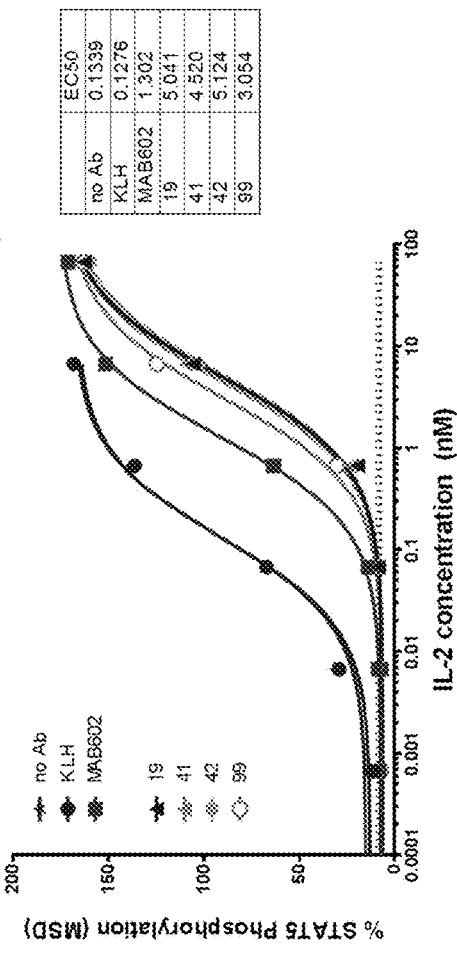
FIG. 7A
FIG. 7B

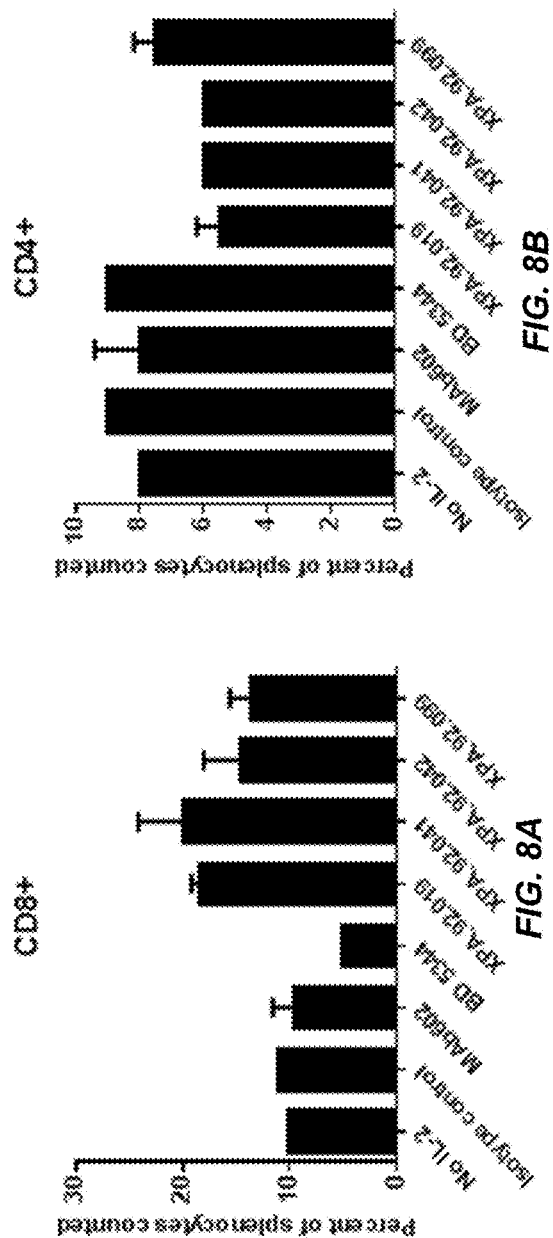
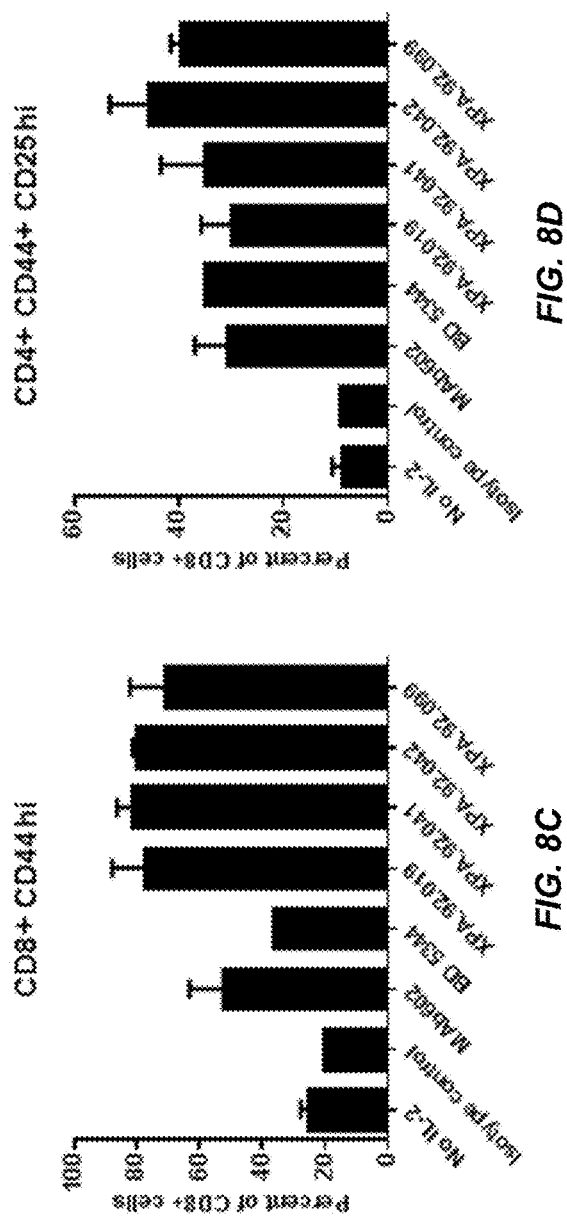
FIG. 8A, FIG. 8B, FIG. 8C, FIG. 8D

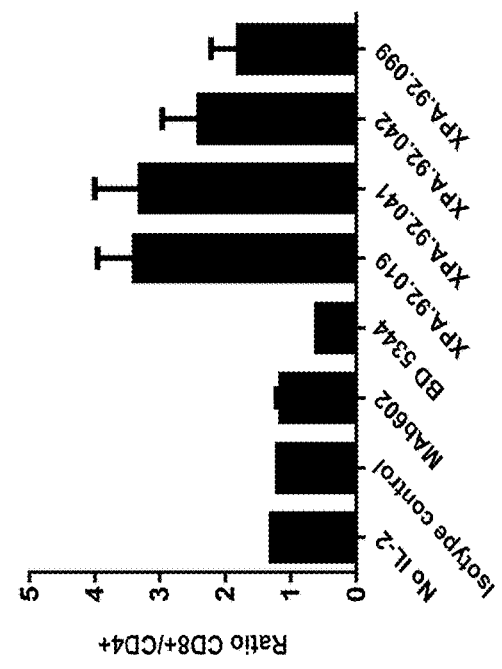
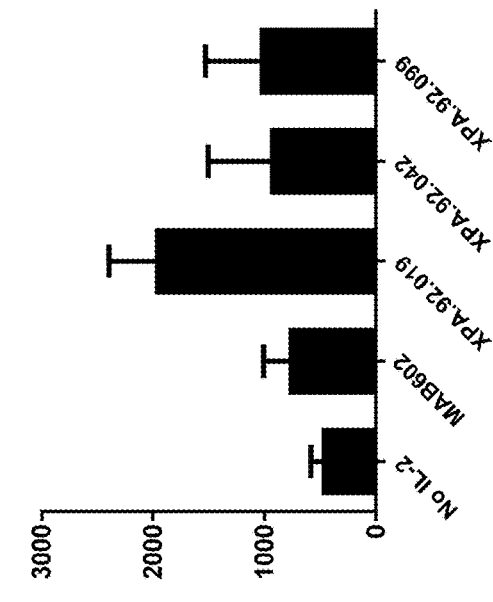
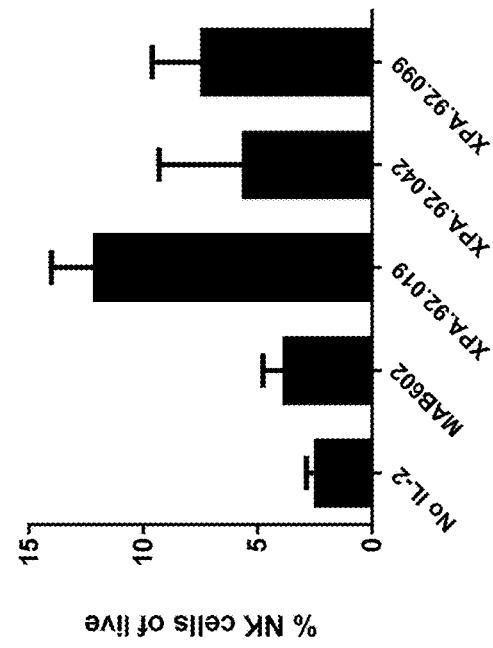
FIG. 8E
FIG. 8F
FIG. 8G

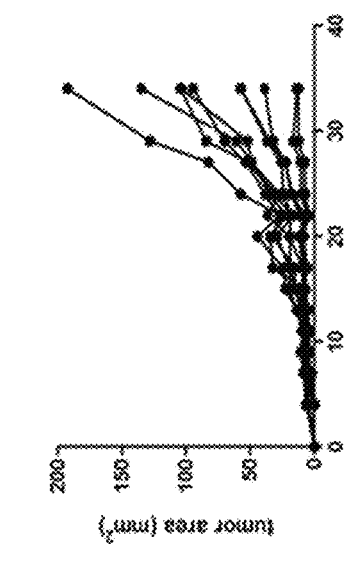
FIG. 9A Vehicle control
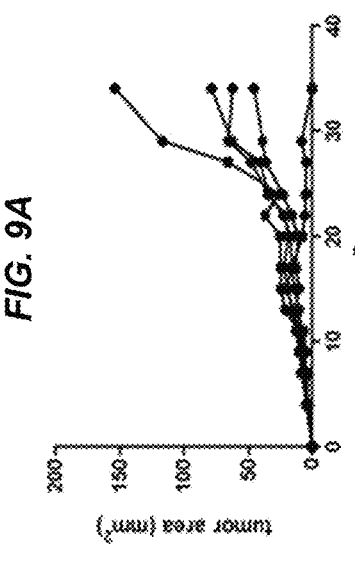
FIG. 9B IL-2/mAb99
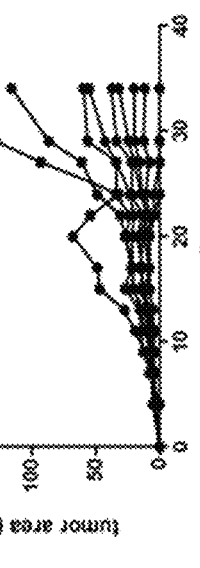
FIG. 9C anti-PD-1 mAb
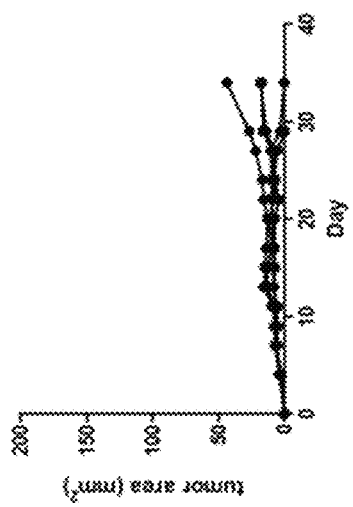
FIG. 9D IL-2/mAb99 + anti-PD-1 mAb
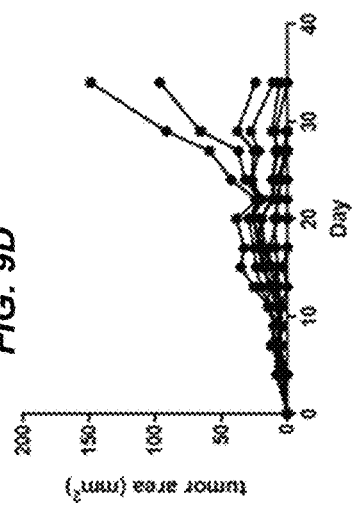
FIG. 9E anti-CTLA-4 mAb
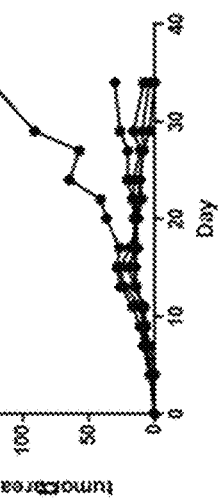
FIG. 9F IL-2/mAb99 + anti-CTLA-4 mAb

| SEQ ID NO: | Name | Sequence |
|---|---|---|
| 1 | XPA.92.019 HV<br>H-CDR1 26-33<br>H-CDR2 51-58<br>H-CDR3 97-108 | EVQLVESGGG LVQPGRSLRL SCAASGFTFS YYGMHWVRQA PGKGLEWVAD ISNDGSNKYY ADSVKGRFTI SRDNSKTTLY LQMNSLRPED TAVYYCATPY YDSSGLDYWG QGTLVTVSS |
| 2 | XPA.92.019 HV | gaagtgcagc tggtggagtc tgggggaggc ttggtccagc ctggggagtc cctgagactc tcctgtgcag cctctggatt cacctttagt tactatggca tgcactgggt ccgccaggct ccaggcaagg ggctagaagtg ggtggcagat atatcaaatg atggaagtaa taaatattac gcagactctg tgaagggccg attcaccatc tccagagaca acgctgtgtat attactgtgc acgcctgtat ctgcaaatga acagcctgag acctgaggac acggctgtat attactgtgc gacccctta ctgcaaatga acagcctgag acctgaggac acggctgtat attactgtgc gacccctta tatgatagta gtggttgga ctactgggc caggaaccc tggtcaccgt ctcctca |
| 3 | XPA.92.041 HV<br>H-CDR1 26-33<br>H-CDR2 51-58<br>H-CDR3 97-106 | EVQLVQSGAE VKKPGESLKI SCKGSGYNFD TYWIGWVRQM PGRGLEWMGT IYPADSDTRY SPSFQGQVTT SADKSISTAY LQWGSLRASD TAMYYCARFS SSAYDIWGQG TMVTVSS |
| 4 | XPA.92.041 HV | gaggtccagc tggtacagtc tggagcagag gtgaaaaagc ccggggagtc tctgaagatt tcctgtaagg gttctggata caacttgat acgtactgga tcggctgggt gcgccagatg cccgggagag gcctggagtg gatgggaacc atctatcctg ctgactcctga gactcctga agtccaagcc tccaagcca ggtcaccacc tcagcccgaca accgcctac ctgcagtggg gcagcctgag agcagaattg gggcaaggg gcagcctgag acaatggtca ccgtctcttc a |
| 5 | XPA.92.042 HV<br>H-CDR1 26-33<br>H-CDR2 51-58<br>H-CDR3 97-106 | EVQLVQSGTE VKKAGDSLKI SCKGSGYNFD TYWIGWVRQM PGRGLEWMGT IYPADSDTRY SPSFQGQVTM SADKSISTAY LQWGSLRASD TAMYYCARFS SSAYDIWGQG TMVTVSS |
| 6 | XPA.92.042 HV | gaggtccagc tggtacagtc tggaacagag gtgaaaaagg ccggggacc tctgaagatt tcctgtaagg gttctggata caacttgat acgtactgga tcggctgggt gcgccagatg cccgggagag gcctggagtg gatgggaacc atctatcctg ctgactcctga gactcctga agtccgtcct ccaagccca ggtcaccatg ggcctcggaa accgcctac ctgcagtggg gcagcctgag agcagaattg gggcaaggg gcagcctgag acaatggtca ccgtctcttc a |
| 7 | XPA.92.099 HV<br>H-CDR1 26-33<br>H-CDR2 51-58<br>H-CDR3 97-110 | QVQLVESGGG LVKPGRSLRL SCAASGFTFN RYAMSWVRQA PGKGLEWVAM ISFDGGNQYY TDSVSGRFTI SRDNSKTTLF LQMDSLRTED TAVYYCVRSP AGDWVAYFDY WGQGTLVTVS S |

FIG. 12A

| SEQ ID NO: | Name | Sequence |
|---|---|---|
| 8 | XPA.92.099 HV | caggtgcagc tggtggagtc tgggggaggc ttggtcaagc ctggagactc<br>tcctgtgcag cctctggatt caccttcaat agatatgcca tgagctgggt ccgccaggct<br>ccaggcaagg ggctagagtg ggtggcgatt attccaagaa cagctgtttt<br>acagactccg tgagtggccg tgagtggccg attcaccatc tccagagaca attccaagac cacgctgtttt<br>ctgcaaatgg acagcctgag aactgaggac acggctgtgt attattgtgt gagatcccccg<br>gcggggact gggttgccta ctttgactac tggggccagg gaaccctggt caccgtctcc<br>tca |
| 9 | XPA.92.019 LV (lambda)<br>H-CDR1 26-31<br>H-CDR2 49-51<br>H-CDR3 88-98 | SYELTQPPSV SVSPGQTARI TCSGDALPKR FAYWYQQKAG QAPVLVIYED NKRPSGIPET<br>LSGSSSGGTTA TLTISGAQEE DEADYYCYST DNTGGLWVFG GGTKLTVLG |
| 10 | XPA.92.019 LV | tcctatgagc tgacacagca accctcggtg tcagtgtccc caggacaaac ggccaggatc<br>acctgctctg gagatgcatt gccaaaaaga tttgcttatt ggtaccagca gaaggcaggc<br>caggccccctg tactggtcat ctatgaggac aacaaacgac ccttcagga cgtgggg cctcaggaga<br>ctctcctggct ccagttcagg acaacggcc acttgacaa actatgaaga ggtgtcctg gctgttccggc<br>gatgaagctg actattactg ttactccaca gacacactg gtgtgtgcggc ggtgttcggc<br>ggagggacca agctgaccgt cctaggt |
| 11 | XPA.92.041 LV (lambda)<br>H-CDR1 26-31<br>H-CDR2 49-51<br>H-CDR3 88-98 | SYELTQPPSV SVSPGQTARI TCSGDALPRQ FAYWYQQKPG QAPVLVIYKD TERPSGIPER<br>FSGSSSGTTV TLTISGVQAE DEADYYCQSA DSSGTYHVFG GGTQLTVLG |
| 12 | XPA.92.041 LV | tcctatgagc tgacacagcc accctcggtg tcagtgtccc caggacagaca ggccaggatc<br>acctgctctg gagatgcgtt ccaaggcaa tatataaagac actgagaggc cccctgagcga<br>caggccctg tactggtgat actgagaggc acgttgacca gacaacagtc actgagcga<br>tctctggct ccagttcagg atataaagac tcaatcagca cgtactatca cgtgttgga<br>gacaggctg actattactg tcaatcagca gacacagtg gtacttatca cgtgttgga<br>ggagggcaccc agctgaccgt cctaggt |
| 13 | XPA.92.042 LV (lambda)<br>H-CDR1 26-31<br>H-CDR2 49-51<br>H-CDR3 88-97 | SYELTQPFSV SVSPGQTARI TCSGDALPRK FAYWYQQKSG QAPVLVIYQD TKRPSGIPER<br>FSGSSSGTTV TLTISDVQAE DDADYYCQSA DRSDSYVFGA GTKLTVLG |

FIG. 12B

| SEQ ID NO: | Name | Sequence |
|---|---|---|
| 14 | XPA.92.042 LV (lambda) | tcctatgagc tgacacagcc accctcggtg tcagtgtccc caggacaaac ggccaggatc acctgctctg gagatgcatt gcctaagcag tttgcttact ggtaccagca gaagtcaggc caggcccctg tcctggtgat atatcaagac actaagagac cctcagcga ttctctggct ccagtcagg gacaacagtc acgttgacca tcagtgacgt ccaggcagag gacgaggctg actattattg tcagtcagcc gacagaagtg atcttatgt cttcggagct gggaccacgc tcaccgtcct aggt |
| 15 | XPA.92.099 LV (kappa) L-CDR1 27-32 L-CDR2 50-52 L-CDR3 89-98 | DIQMTQSPSS LSASIGDRVT IPCQASEDIS NHLSWYQQKP GKAPKPLIFD ASDLETGVPS RFSGSGSGTD FALTISSLRP DDFATYYCHQ YHDYPSYTFG HGTKLEIKR |
| 16 | XPA.92.099 LV (kappa) | gacatccaga tgacccagtc tccttcctcc ctgtctgctt ctattggaga cagagtcacc atcccctgcc agcgagtga ggacattagt aatcattaa gttgtatca gcagaaacca gggaaagccc ctaaaccct gatcttcgat gcatccgatt tggaaacagg ggtcccatca aggttcagtg gaagtggatc tgggacagat tttgctctca ccatcagcag cctgcggcct gatgattttg caacttatta ctgccaccag tatcatgatt atccctcgta cacttttggc cacgggacca agctggagat caaacgt |
| 17 | XPA.92.019 HV H-CDR1 | GFTFSYYG |
| 18 | XPA.92.019 HV H-CDR2 | ISNDGSNK |
| 19 | XPA.92.019 HV H-CDR3 | RFEDTAVYYCAT |
| 20 | XPA.92.041 HV H-CDR1 | GYNFDTYW |
| 21 | XPA.92.041 HV H-CDR2 | IYPADSDT |
| 22 | XPA.92.041 HV H-CDR3 | ARFSSSAYDI |
| 23 | XPA.92.042 HV H-CDR1 | GYNFDTYW |
| 24 | XPA.92.042 HV H-CDR2 | IYPADSDT |

FIG. 12C

| SEQ ID NO: | Name | Sequence |
|---|---|---|
| 25 | XPA.92.042 HV H-CDR3 | SSAYDIARFS |
| 26 | XPA.92.099 HV H-CDR1 | GFTFNRYA |
| 27 | XPA.92.099 HV H-CDR2 | ISFDGGNQ |
| 28 | XPA.92.099 HV H-CDR3 | VRSPAGDWVAYFDY |
| 29 | XPA.92.019 LV (lambda) L-CDR1 | ALPKRF |
| 30 | XPA.92.019 LV (lambda) L-CDR2 | EDN |
| 31 | XPA.92.019 LV (lambda) L-CDR3 | YSTDNTGGLWV |
| 32 | XPA.92.041 LV (lambda) L-CDR1 | ALPRQF |
| 33 | XPA.92.041 LV (lambda) L-CDR2 | KDT |
| 34 | XPA.92.041 LV (lambda) L-CDR3 | DSSGTYHQSA |
| 35 | XPA.92.042 LV (lambda) L-CDR1 | ALPRKF |
| 36 | XPA.92.042 LV (lambda) | QDT |

FIG. 12D

| SEQ ID NO: | Name | Sequence |
|---|---|---|
| | L-CDR2 | |
| 37 | XPA.92.042 LV (lambda) L-CDR3 | QSADRSDSYV |
| 38 | XPA.92.099 LV (kappa) L-CDR1 | EDISNH |
| 39 | XPA.92.099 LV (kappa) L-CDR2 | DAS |
| 40 | XPA.92.099 LV (kappa) L-CDR3 | HQYHDYPSYT |

HV = Heavy Chain Variable Region
LV = Light Chain Variable Region

*FIG. 12E*

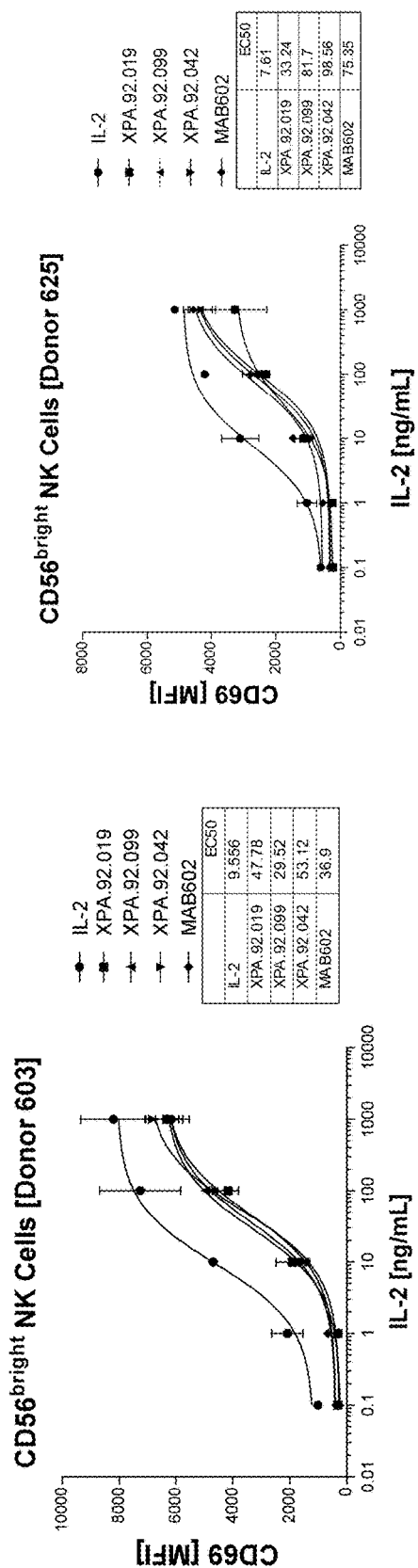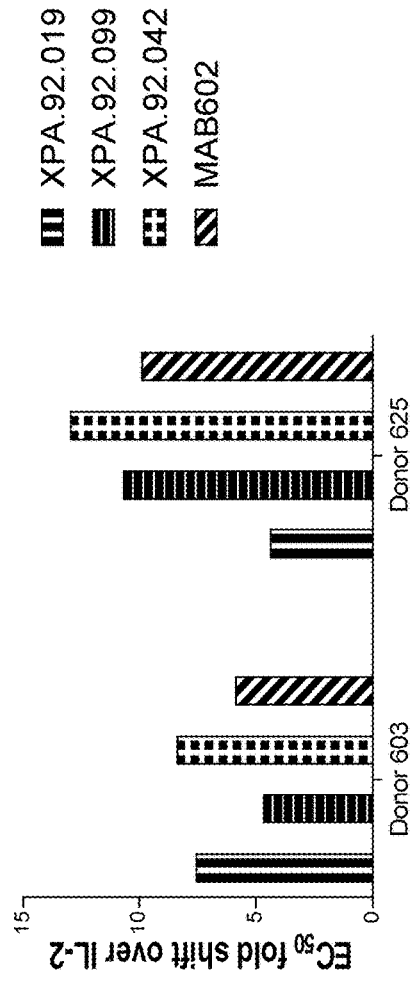
FIG. 13A
FIG. 13B
FIG. 13C

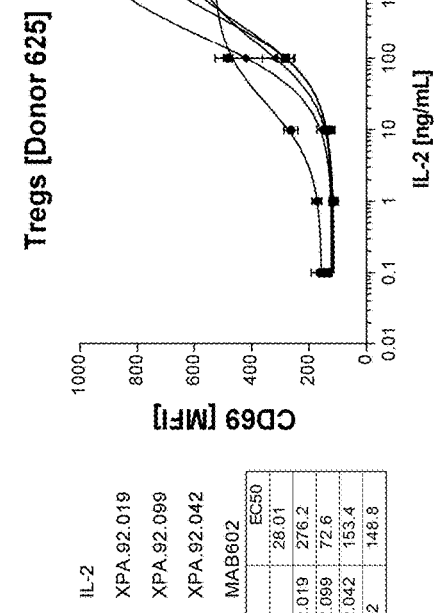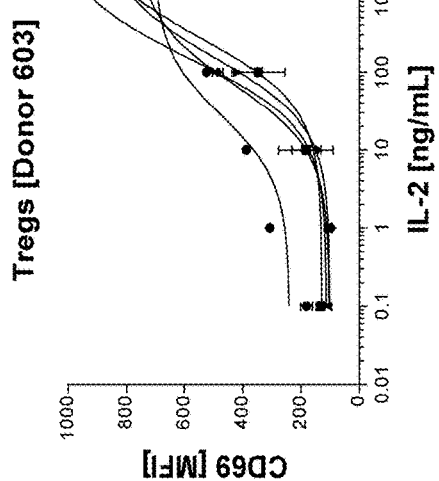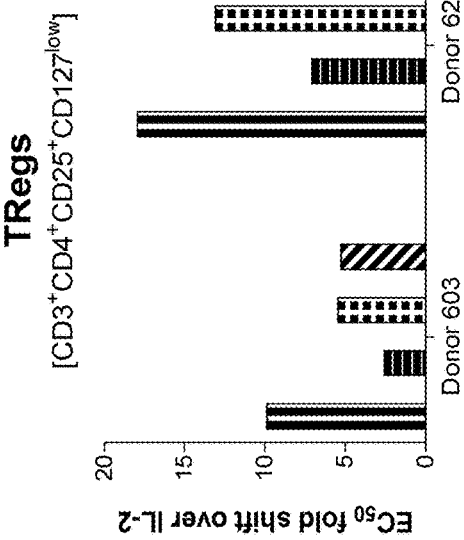
FIG. 14A
FIG. 14B
FIG. 14C

ANTIBODIES THAT BIND INTERLEUKIN-2 AND USES THEREOF

CROSS-REFERENCE TO RELATED APPLICATIONS

The present application is a divisional of Application Ser. No. 15/718,152, filed on Sep. 28, 2017, allowed, which claims the priority benefit of U.S. Provisional Patent Application No. 62/401,158, filed Sep. 28, 2016 and U.S. Provisional Patent Application No. 62/421,038, filed Nov. 11, 2016, hereby incorporated by reference in their entireties.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: Filename: 51134A_Seqlisting.txt; Size: 35,400 bytes; Created: Dec. 4, 2020.

FIELD OF THE INVENTION

The present disclosure relates, in general, to interleukin-2 (IL-2) antibodies and therapy for treating conditions associated with IL-2 signaling comprising administering to a subject in need thereof a therapeutically effective amount of an IL-2 antibody.

BACKGROUND

Interleukin-2 (IL-2) is a 15 kDa peptide that is a member of the four-α helix bundle family of cytokines (Wang et al., *Annual review of immunology* 27, 29-60 (2009)). Originally identified in 1976 as a T cell growth factor, it has been described by a variety of names, including T-cell growth factor (TCGF), lymphocyte-conditioned medium (LCM) factor, T-cell mitogenic factor (TMF), killer helper factor (KHF), and T-cell replacing factor (TRF) (Lotze M T, *Interleukin-2, In Human Cytokines: Handbook for basic and clinical research*, pp 81-96(1992); Smith et al., *Cytokine Reference*, pp 113-125 (2001)). IL-2 is produced by many cells including CD4 T cells, CD8 T cells, dendritic cells (DCs), natural killer (NK) cells, and natural killer T (NKT) cells. IL-2 is produced after a wide range of signals including engagement of the T cell receptor (TCR) and rapidly and transiently produced upon engaging the TCR and costimulatory molecules such as CD28 on naive T cells. The transient nature of IL-2 secretion depends on transcriptional induction by TCR signals and stabilization of IL-2 mRNA by costimulatory signals, followed by transcriptional silencing of the IL-2 gene and rapid degradation of IL-2 mRNA. A classical auto-regulatory feedback loop has recently been described in which IL-2 inhibits its own production (Malek T R, *Annual review of immunology* 26, 453-479 (2008)).

The receptor for IL-2 (IL-2 R) consists of three chains, IL-2 Ra (also known as CD25), IL-2 Rβ (also known as CD122), and the common gamma chain, γc (also known as CD132). The three receptor chains are expressed separately and differently on various cell types. IL-2 signals through interactions between IL-2 Rβ and γc that activate cellular pathways such as the Jak/Stat, PI3K-AKT, and MAPK pathways.

SUMMARY OF THE INVENTION

The present disclosure provides methods and compositions for the treatment of disease or disorders associated with IL-2 signaling or where modulation of IL-2 signaling can lead to improved clinical (or immune) response. The disclosure provides antibodies that bind human IL-2. It is provided that the antibodies described herein can have differential effects on IL-2 binding to any or all of the IL-2 R chains (IL-2 Rα, IL-2 Rβ, and γc). In particular, the present disclosure provides methods of use of such antibodies in the treatment of cancer.

In various embodiments, the disclosure provides an antibody specific for IL-2 with an affinity $K_D$ of $2\times10^{-9}$ M or less. In various embodiments, the disclosure provides an antibody specific for IL-2 with an affinity $K_D$ of $1\times10^{-10}$ M or less. In exemplary embodiments, an anti-IL-2 antibody described herein binds at least with an affinity of $10^{-10}$ M, $10^{-11}$ M, $10^{-12}$ M, $10^{-13}$ M or less. In certain embodiments, the affinity is measured by surface plasmon resonance or KinExA assay.

In various embodiments, the antibody inhibits IL-2 signaling through IL-2 Rαβγ and through IL-2 Rβγ, and the antibody inhibits IL-2 signaling through IL-2 Rαβγ to a greater extent than through IL-2 Rβγ.

In a related embodiment, the antibody binds IL-2 and inhibits binding of IL-2 with an IL-2 receptor alpha (IL-2 Rα) subunit. In various embodiments, the antibody inhibits IL-2 signaling through IL-2 Rαβγ to a greater extent than through IL-2 Rβγ.

In a related embodiment, the antibody does not completely block binding of human IL-2 to cells expressing human or mouse IL-2 Rβ or IL-2 Rβγ complex. In a related aspect, the antibody binds at a site allosteric to binding of IL-2 to IL-2 Ra or IL-2 Rβ and γc chains.

In a various embodiments, the antibody is a negative modulator antibody, optionally wherein the antibody is capable of weakening the binding affinity between IL-2 and IL-2 receptor α (IL-2 Rα) by at least about 2-fold, optionally up to 1000-fold. In other embodiments, an antibody described herein is capable of weakening the binding affinity between IL-2 and IL-2 Ra by at least 2-1000 fold, 10-100 fold, 2-fold, 5-fold, 10-fold, 25-fold, 50-fold, 100-fold, 200-fold, 300-fold, 400-fold, 500-fold, 600-fold, 700-fold, 800-fold, 900-fold or 1000-fold. In various embodiments, the antibody complexed with IL-2 binds to cells expressing IL-2 Rβ and γc with an EC50 of about 5 nM or less. In various embodiments, the antibody binds to cells expressing IL-2 Rβ (but not γc) with an EC50 of about 200 nM or less. In some embodiments, the antibody complexed with IL-2 binds to cells expressing IL-2 Rβ and γc with an EC50 in a range of 0.1-100 nM, 0.1-10 nM, 1-5 nM. In various embodiments, the antibody complexed with IL-2 binds to cells expressing IL-2 Rβ and γc with an EC50 of 1, 2, 3, 4 or 5 nM. In some embodiments, the antibody complexed with IL-2 binds to cells expressing IL-2 Rβ (but not γc) with an EC50 in a range of 10-500 nM, 10-300 nM, 10-200 nM. In various embodiments, the antibody complexed with IL-2 binds to cells expressing IL-2 Rβ and γc with an EC50 of 10, 50, 100, 150 or 200 nM. In related embodiments, the antibody complexed with IL-2 binds to cells expressing IL-2 Rβ and γc 9- to 40-fold more than cells expressing IL-2 Rβ (but not γc).

In various embodiments, the antibody binds to human IL-2 and one or more of mouse, rat or rabbit IL-2.

In various embodiments, the antibody inhibits IL-2 stimulation of STAT5 activation in cells expressing IL-2 Rα, IL-2 RP, and γc to a greater extent than cells expressing IL-2 Rβ and γc, but not IL-2 Rα. For example, in cells expressing mouse IL-2 Rα, Rβ and γc (e.g., CTLL-2), EC50 shifts can range from 293- to 793-fold compared to 13- to 16-fold for cells expressing mouse IL-2 Rβ and γc (e.g., mouse primary NK cells). For cells expressing human IL-2 Rα, RP and γc (e.g., NK92 cell line), EC50 shifts can range from 495- to 1855-fold compared to 45- to 104-fold for cells expressing human IL-2 Rβ and γc (human CD25+ depleted primary NK cells) or 5- to 9-fold for CHO-K1 cells engineered to express human Rβ and γc. The ratios of EC50 shifts were 18- to 60-fold greater for mouse Rα, Rβ, and γc compared to mouse Rβ and γc (76-fold for control antibody MAB602, also known as clone 5355) and 9- to 19-fold for human Rα, Rβ, and γc compared to human Rβ and γc (50-fold for MAB602). In a related embodiment, the antibody inhibits IL-2 stimulation of STAT5 activation in cells that express mouse IL-2 Rα, IL-2 Rβ, and γc by 200-fold or more for cells that express human IL-2 Rα, IL-2 Rβ, and γc by 400-fold or more. In a related embodiment, the antibody inhibits IL-2 stimulation of STAT5 activation in cells that express human IL-2 Rβ and γc, but not IL-2 Ra by less than 10-fold (CHO-Rβγ) or 150-fold (e.g., in Human CD25+ depleted primary NK cells), or cells expressing mouse IL-2 Rβ and γc (e.g., mouse NK cells) by less than 20-fold.

In various embodiments, the antibody inhibits IL-2 stimulation of proliferation in cells expressing IL-2 Rα, IL-2 Rβ, and γc to a greater extent than in cells expressing IL-2 Rβ and γc, but not IL-2 Rα. In various embodiments, the antibody inhibits IL-2 stimulation of proliferation of NK cells that express IL-2 Rα, IL-2 Rβ, and γc, by greater than 20-fold. In various embodiments, the antibody inhibits IL-2 stimulation of proliferation of BaF3 cells that express IL-2 Rβ and γc, but not IL-2 Rα, by less than 12-fold.

In one embodiment, the IL-2 antibody is a monoclonal antibody.

In various embodiments, the IL-2 antibody is a human or humanized antibody.

In various embodiments, the antibody is selected from the group consisting of XPA.92.019, XPA.92.041, XPA.92.042 or XPA.92.099.

In one aspect, the disclosure provides an antibody that binds human interleukin-2 (IL-2) comprising (a) a heavy chain CDR1 amino acid sequence set forth in SEQ ID NOs: 17, 20, 23, or 26, or a variant thereof in which one or two amino acids have been changed; (b) a heavy chain CDR2 amino acid sequence set forth in SEQ ID NOs: 18, 21, 24, or 27 that is from the same heavy chain variable region as (a), or a variant thereof in which one or two amino acids have been changed; and (c) a heavy chain CDR3 amino acid sequence set forth SEQ ID NOs: 41, 22, 25, or 28 that is from the same heavy chain variable region as (a), or a variant thereof in which one or two amino acids have been changed.

In a related aspect, the disclosure provides an antibody that binds human interleukin-2 (IL-2) comprising: (a) a heavy chain CDR1 amino acid sequence set forth in SEQ ID NOs: 17, 20, 23, or 26, or a variant thereof having at least 70% identity thereto; (b) a heavy chain CDR2 amino acid sequence set forth in SEQ ID NOs: 18, 21, 24, or 27 that is from the same heavy chain variable region as (a), or a variant thereof having at least 70% identity thereto; and (c) a heavy chain CDR3 amino acid sequence set forth in SEQ ID NOs: 4119, 22, 25, or 28 that is from the same heavy chain variable region as (a), or a variant thereof having at least 70% identity thereto.

In a further aspect, the disclosure provides an antibody that binds human interleukin-2 (IL-2) comprising: (a) a heavy chain CDR1 amino acid sequence set forth in SEQ ID NOs: 17, 20, 23, or 26, or a variant thereof having at least 70% identity thereto; (b) an independently selected heavy chain CDR2 amino acid sequence set forth in SEQ ID NOs: 18, 21, 24, or 27, or a variant thereof having at least 70% identity thereto; and (c) an independently selected heavy chain CDR3 amino acid sequence set forth in SEQ ID NOs: 41, 22, 25, or 28 or a variant thereof having at least 70% identity thereto.

In certain embodiments, at least two of the heavy chain CDR1, CDR2 or CDR3 amino acid sequences are set forth in any one of SEQ ID NOs: 17, 18, 20-28 and 41. In a related embodiment, three of the heavy chain CDR1, CDR2 and CDR3 amino acid sequences are set forth in any one of SEQ ID NOs: 17, 18, 20-28 and 41.

In some embodiments, an antibody contemplated herein comprises an amino acid sequence at least 85% identical to a heavy chain variable region amino acid sequence set forth in SEQ ID NOs: 1, 3, 5, or 7. In some embodiments, provided herein is an antibody that comprises an amino acid sequence at least 95% identical to a heavy chain variable region amino acid sequence set forth in SEQ ID NOs: 1, 3, 5, or 7.

It is further contemplated that an antibody described herein comprises a polypeptide sequence having an amino acid sequence at least 70% identical over all three HCDRs in a heavy chain variable region, the amino acid sequences of HCDR1, HCDR2 and HCDR3 set forth in any one of SEQ ID NOs: 17, 18, 20-28 and 41.

In certain embodiments, an antibody contemplated herein comprises one or more heavy chain framework amino acids have been replaced with corresponding amino acid(s) from another human antibody amino acid sequence.

In one embodiment, an antibody contemplated herein further comprises any one of the light chain CDR amino acid sequences set forth in any one of SEQ ID NOs: 29-40. In other embodiments, an antibody contemplated herein comprises at least two of the light chain CDR amino acid sequences set forth in any one of SEQ ID NOs: 29-40. In other embodiments, an antibody contemplated herein comprises at least three of the light chain CDR amino acid sequences set forth in any one of SEQ ID NOs: 29-40.

In another aspect, an antibody described herein comprises (a) a light chain CDR1 amino acid sequence set forth in SEQ ID NOs: 29, 32, 35, or 38, or a variant thereof in which one or two amino acids have been changed; (b) a light chain CDR2 amino acid sequence set forth in SEQ ID NOs: 30, 33, 36, or 39 that is from the same light chain variable region as (a), or a variant thereof in which one or two amino acids have been changed; and (c) a light chain CDR3 amino acid sequence set forth in SEQ ID NOs: 31, 34, 37, or 40 that is from the same light chain variable region as (a), or a variant thereof in which one or two amino acids have been changed.

In alternative embodiments, an antibody contemplated herein comprises: (a) a light chain CDR1 amino acid sequence set forth in SEQ ID NOs: 29, 32, 35, or 38, or a variant thereof in which one or two amino acids have been changed; (b) an independently selected light chain CDR2 amino acid sequence set forth in SEQ ID NOs: 30, 33, 36, or 39, or a variant thereof in which one or two amino acids have been changed; and (c) an independently selected light chain CDR3 amino acid sequence set forth in SEQ ID NOs: 31, 34, 37, or 40, or a variant thereof in which one or two amino acids have been changed.

In certain embodiments, at least two of the light chain CDR1, CDR2 or CDR3 amino acid sequences are set forth in any one of SEQ ID NOs: 29-40.

It is further contemplated that an antibody described herein comprises an amino acid sequence at least 70% identical to a light chain variable region amino acid sequence set forth in any one of SEQ ID NOs: 9, 11, 13, or 15. In a related embodiment, the antibody comprises an amino acid sequence at least 85% identical to a light chain variable region amino acid sequence set forth in any one of SEQ ID NOs: 9, 11, 13, or 15. In a further embodiment, the antibody comprises an amino acid sequence at least 95% identical to a light chain variable region amino acid sequence set forth in any one of SEQ ID NOs: 9, 11, 13, or 15. In still another embodiment, the antibody comprises a light chain variable region amino acid sequence set forth in any one of SEQ ID NOs: 9, 11, 13, or 15.

In a further embodiment, an antibody described herein comprises a polypeptide sequence having an amino acid sequence at least 70% identical over all three LCDRs of a light chain variable region, the amino acid sequences of LCDR1, LCDR2 and LCDR3 set forth in any one of SEQ ID NOs: 29-40.

In certain embodiments, an antibody described herein comprises (i) an amino acid sequence at least 70% identical over all three LCDRs, of a light chain variable region, the amino acid sequences of LCDR1, LCDR2 and LCDR3 set forth in any one of SEQ ID NOs: 29-40 and (ii) an amino acid sequence at least 70% identical over all three HCDRs of a heavy chain variable region, the amino acid sequences of HCDR1, HCDR2 and HCDR3 set forth in any one of SEQ ID NOs: 17, 18, 20-28 and 41.

In various embodiments, the disclosure provides an antibody that binds interleukin-2 (IL-2) comprising a light chain variable region and/or a heavy chain variable region, wherein (a) the light chain variable region comprises at least a CDR1 selected from SEQ ID NOs: 29, 32, 35, or 38, or sequences at least 80% identical thereto, a CDR2 selected from SEQ ID NOs: 30, 33, 36, or 39, or sequences at least 80% identical thereto, and/or a CDR3 selected from SEQ ID NOs: 31, 34, 37, or 40, or sequences at least 80% identical thereto; and/or wherein (b) the heavy chain variable region comprises at least a CDR1 selected from SEQ ID NOs: 17, 20, 23, or 26, or sequences at least 80% identical thereto, a CDR2 selected from SEQ ID NOs: 18, 21, 24, or 27, or sequences at least 80% identical thereto, and/or a CDR3 selected from SEQ ID NOs: 41, 22, 25, or 28, or sequences at least 80% identical thereto.

In various embodiments, the disclosure provides an antibody that binds IL-2 comprising a light chain variable region and/or a heavy chain variable region, wherein (a) the light chain variable region comprises at least a CDR1 selected from SEQ ID NOs: 29, 32, 35, or 38, or sequences at least 90% identical thereto, a CDR2 selected from SEQ ID NOs: 30, 33, 36, or 39, or sequences at least 90% identical thereto, and/or a CDR3 selected from SEQ ID NOs: 31, 34, 37, or 40, or sequences at least 90% identical thereto; and/or wherein (b) the heavy chain variable region comprises at least a CDR1 selected from SEQ ID NOs: 17, 20, 23, or 26, or sequences at least 90% identical thereto, a CDR2 selected from SEQ ID NOs: 18, 21, 24, or 27, or sequences at least 90% identical thereto, and/or a CDR3 selected from SEQ ID NOs: 4119, 22, 25, or 28, or sequences at least 90% identical thereto.

In certain embodiments, an antibody described herein inhibits binding of IL-2 with an IL-2 receptor alpha (IL-2 R-α) subunit. In a related embodiment, an antibody described herein does not completely block binding of IL-2 to an IL-2 Rβγ complex.

In certain embodiments, an antibody described herein binds at a site allosteric to binding of IL-2 to IL-2 Rα, IL-2Rβ, IL-2Rγ and/or IL-2 Rβγ. In certain embodiments, an antibody described herein binds to IL-2 and induces a conformational change that impacts binding preference to IL-2Rα, IL-2Rβ, and/or γc.

In certain embodiments, an antibody described herein does not shift the EC50 of binding of IL-2 to IL-2 Rβγ complex by more than 3-fold.

In certain embodiments, an antibody described herein inhibits STAT5 activation in a cell in response to stimulation of the IL-2 R with IL-2.

In some embodiments, an antibody of the disclosure further comprises a heavy chain constant region, wherein the heavy chain constant region is a modified or unmodified IgG, IgM, IgA, IgD, IgE, a fragment thereof, or combinations thereof.

In certain embodiments, an antibody is provided in which one or more light chain framework amino acids have been replaced with corresponding amino acid(s) from another human antibody amino acid sequence, optionally wherein the framework comprises one or more of the changes set out in FIGS. 12A-12E.

In one aspect, the antibody of the disclosure is selected from the group consisting of XPA.92.019, XPA.92.041, XPA.92.042 or XPA.92.099.

In one embodiment, an antibody described herein further comprises a human light chain constant region attached to said light chain variable region. In some embodiments, the light chain constant region is a modified or unmodified lambda light chain constant region, a kappa light chain constant region, a fragment thereof, or combinations thereof.

In another aspect, the disclosure provides an isolated nucleic acid molecule comprising a nucleotide sequence that encodes the heavy chain or light chain as described herein. In various embodiments the nucleotide sequences are set out in SEQ ID NOs: 2, 4, 6, 8, 10, 12, 14, or 16.

In a further aspect, the disclosure provides an expression vector comprising a nucleic acid molecule contemplated herein operably linked to an expression control sequence. Also contemplated is a host cell comprising an expression vector or a nucleic acid molecule of the disclosure. In certain embodiments, the disclosure provides a host cell comprising a nucleic acid molecule encoding a heavy chain and a light chain variable region, wherein the heavy chain and light chain nucleic acids are expressed by different nucleic acids or on the same nucleic acid.

In a related aspect, the disclosure provides a method of using the host cell as described herein to produce an antibody, the method comprising culturing the host cell under suitable conditions and recovering said antibody. Also provided is an antibody produced by the method disclosed herein.

The disclosure further contemplates a sterile pharmaceutical composition comprising the antibody as disclosed herein and a pharmaceutically acceptable carrier.

In another aspect, the disclosure provides a method for suppressing IL-2 activity in a patient in need thereof comprising the step of administering to a subject in need thereof a therapeutically effective amount of an antibody or a pharmaceutical composition contemplated herein. It is contemplated, in various embodiments, that the method suppresses IL-2 activity in cell populations such as regulatory T cells/CD25 hi, T effector/CD 25 lo, and/or cells with high affinity trimeric IL-2 receptor (IL-2 Rαβγ) or IL-2Rα.

In another aspect, the disclosure provides a method for treating a disease, condition or disorder associated with increased interleukin-2 (IL-2) or interleukin-2 receptor (IL-2 R) expression or activity comprising the step of administering to a subject in need thereof a therapeutically effective amount of an antibody or a pharmaceutical composition contemplated herein.

In various embodiments, the disclosure provides a method for treating a disease, condition or disorder in which modulation of interleukin-2 (IL-2) signaling is beneficial to improve immune response in a subject comprising the step of administering to a subject in need thereof a therapeutically effective amount of an antibody or a pharmaceutical composition contemplated herein.

In another aspect, the disclosure provides a method for treating a disease, condition or disorder selected from the group consisting of cancer, microbial infection, asthma and autoimmune disease.

In various embodiments, the cancer is selected from the group consisting of melanoma, renal cell carcinoma, lymphoma, sarcoma, breast cancer, lung cancer, bladder cancer, colon cancer, gastric cancer, non-small cell lung carcinoma (NSCLC), bladder cancer, head and neck cancer, skin cancer, and squamous cell carcinoma (SCC).

In various embodiments, the microbial infection is a viral, bacterial or fungal infection.

In various embodiments, administering to a subject in need thereof a therapeutically effective amount of an antibody or a pharmaceutical composition contemplated herein reduces tumor volume in the subject.

In various embodiments, administering to a subject in need thereof a therapeutically effective amount of an antibody or a pharmaceutical composition contemplated herein increases the ratio of CD8+ T cells to CD4+ T cells in the subject. In various embodiments, the antibody increases the ratio of CD8+ to CD4+ T cells by at least about 1-fold, optionally up to 100-fold. In other embodiments, an antibody described herein is capable of increasing the ratio of CD8+ to CD4+ T cells by at least 1-100 fold, 10-100 fold, 1-fold, 2-fold, 3-fold, 4-fold, 5-fold, 6-fold, 7-fold, 8-fold, 9, fold, 10-fold, 25-fold, 50-fold, or 100-fold.

In various embodiments, the antibody disclosed herein is administered intravenously, intraarterially, intraperitoneally, intratumorally, intramuscularly, intradermally or subcutaneously.

In various embodiments, the antibody disclosed herein is administered in combination with a second agent. In related embodiments, the second agent is IL-2, an IL-2 variant, or an agent that can increase IL-2 levels, a checkpoint inhibitor, a CART/TIL agent, an antibody to a tumor antigen or a vaccine. In related embodiments, the checkpoint inhibitor is selected from the group consisting of an anti-PD-1 antibody, an anti-PDL-1 antibody, an anti-CTLA-4 antibody, a PD-1 inhibitor, a PDL-1 inhibitor or a CTLA-4 inhibitor.

In various embodiments, when the antibody is administered in combination with IL-2, the IL-2 or IL-2 variant and the IL-2 antibody are administered in a 1:1 molar ratio. In various embodiments, administering the IL-2 antibody in combination with IL-2 or an IL-2 variant increases the therapeutic index (TI) of IL-2 by at least 2, 3, 4, 5, 6, 7, 8, 9, or 10-fold or more.

In various embodiments, it is contemplated that the antibody can be administered in combination with IL-2 and a second agent such as a checkpoint inhibitor, a CART/TIL agent, an antibody to a tumor antigen or a vaccine.

In various embodiments, provided herein is a method of treating a disease, e.g., cancer, comprising administering an IL-2 antibody in combination with IL-2, optionally also in combination with a checkpoint inhibitor or other adjunctive oncology therapy, whereby efficacy against a non-IL-2 responsive tumor type is now made sensitive to growth and/or metastasis inhibition.

In various embodiments, IL-2 can be complexed to the antibody prior to administration, with or without administration of another second agent described herein.

In various embodiments, the antibody disclosed herein is administered once per week, once every 2 weeks, twice per month, once monthly, once every two months, or once every three months or less.

In various embodiments, when the IL-2 and IL-2 antibody are pre-mixed, the agents could be administered together twice weekly. In various embodiments, the IL-2 is administered at a dose of 0.1 to 10 mg/kg. In various embodiments, the IL-2 antibody is administered intravenously.

If adding IL-2 dosing relevant to Il-2 antibody, it is contemplated that the IL-2 is administered sequentially, for example on the same day, and in certain embodiments, the IL-2 antibody is administered prior to administration of the IL-2. In various embodiments, the IL-2 antibody is administered weekly with weekly or multi-times per week administration of IL-2 following administration of the antibody.

In various embodiments, the IL-2 antibody is administered 1 time per week and IL-2 therapy (e.g., Proleukin) is administered on the known prescribing schedule, but at a lower IL-2 dose.

In various embodiments, the disclosure provides a method for administering a composition comprising an antibody or a pharmaceutical composition disclosed herein in the treatment a condition or disorder associated with increased or decreased IL-2 or IL-2R expression or activity.

In one aspect, the disclosure provides a method for modulating IL-2 activity in a cell comprising the step of contacting the cell with an amount of an antibody or a pharmaceutical composition disclosed herein effective to modulate IL-2 activity in the cell.

Also contemplated is a composition comprising any of the foregoing antibodies or compositions of the disclosure that bind IL-2, or use thereof in preparation of a medicament, for treatment of any of the disorders described herein associated with IL-2 or IL-2R expression or activity. Syringes, e.g., single use or pre-filled syringes, sterile sealed containers, e.g. vials, bottle, vessel, and/or kits or packages comprising any of the foregoing antibodies or compositions, optionally with suitable instructions for use, are also contemplated.

It is understood that each feature or embodiment, or combination, described herein is a non-limiting, illustrative example of any of the aspects of the invention and, as such, is meant to be combinable with any other feature or embodiment, or combination, described herein. For example, where features are described with language such as "one embodiment", "some embodiments", "certain embodiments", "further embodiment", "specific exemplary embodiments", and/or "another embodiment", each of these types of embodiments is a non-limiting example of a feature that is intended to be combined with any other feature, or combination of features, described herein without having to list every possible combination. Such features or combinations of features apply to any of the aspects of the invention. Where examples of values falling within ranges are disclosed, any of these examples are contemplated as possible endpoints of a range, any and all numeric values between such endpoints are contemplated, and any and all combinations of upper and lower endpoints are envisioned.

The headings herein are for the convenience of the reader and not intended to be limiting. Additional aspects, embodi-

BRIEF DESCRIPTION OF THE DRAWINGS

FIGS. 2A-2D show the measurement of XPA.92.019 (FIG. 2A), XPA.92.041 (FIG. 2B), XPA.92.042 (FIG. 2C), XPA.92.099 (FIG. 2D) binding to cells expressing IL-2 Rβ or IL-2 Rβγ in the presence of variable IL-2 concentrations.

FIGS. 3A-3C show the measurement of XPA.92.019 (FIG. 3A), XPA.92.041 (FIG. 3B) and XPA.92.042 (FIG. 3C) antibody titration and binding to cells expressing IL-2 Rβ or IL-2 Rβγ in the absence and presence of a fixed concentration of IL-2 (100 nM).

FIGS. 4A-4C show the proliferative response to IL-2 of the BaF3-IL-2 Rβγ (FIG. 4A), NK-92 (FIG. 4B) and CTLL-2 (FIG. 4C) cells to IL-2 in the presence of 0.001-100 ng/mL anti-IL-2 antibodies or controls.

FIGS. 5A-5C show the effect of IL-2 antibodies as EC50 shifts for IL-2-induced proliferation of NK92 (FIG. 5A), BaF3-IL-2 Rβγ (FIG. 5B) and CTLL-2 cells (FIG. 5C).

FIG. 6 shows the alignment of IL-2 sequences for different species and the IL-2 R alpha chain binding sites on the IL-2 protein.

FIGS. 7A-7C show IL-2-induced phosphorylation of STAT5 in human NK-92 (FIG. 7A), human primary NK cells (Ra depleted) (FIG. 7B), or mouse primary NK cells (FIG. 7C) in the presence of anti-IL-2 antibody complexes or controls.

FIGS. 8A-8G show graphical representations of the frequency of T cell and NK cell subsets in the spleen: Percentage of CD8+(FIG. 8A); CD4+(FIG. 8B); CD8+CD44hi (FIG. 8C); CD4+CD44+CD25hi (FIG. 8D); the ratio of CD8+ to CD4+ cells (FIG. 8E); the percentage of NK cells (FIG. 8F) and the mean Granzyme B (GRZB) production by NK cells (FIG. 8G) of C57BL/6mice after IL-2/antibody complex administration in vivo.

FIGS. 9A-9F show the response of individual tumors in a subcutaneous LLC xenograft mouse model treated with vehicle control (FIG. 9A), IL-2/anti-IL-2 antibody complex (FIG. 9B), anti-PD-1 antibody alone (FIG. 9C), IL-2/mAb, XPA.92.099+anti-PD-1 antibody, (FIG. 9D), anti-CTLA-4 antibody alone (FIG. 9E) and IL-2/mAb, XPA.92.099+anti-CTLA-4 antibody, (FIG. 9F). In each graph, the line at day 29 represents the last day of treatment.

FIGS. 12A-12E show the sequences and corresponding sequence identification (ID) number (NO) of heavy chain and light chain variable regions and complementarity determining regions (CDRs) as designated by the IMGT system for IL-2 antibodies, XPA.92.019, XPA.92.041, XPA.92.042, and XPA.92.099.

FIGS. 13A-13C show analysis of human PBMCs treated with various doses of IL-2 pre-complexed with a fixed 200 nM concentration of indicated antibodies for 24 hours. Samples were stained for NK cell markers and CD69 expression, and analyzed by flow cytometry, gated on lymphocytes/CD3-/CD56bright. Mean Fluorescence Intensity (MFI) of CD69 was plotted against IL-2 concentration for donor 603 (FIG. 13A) and donor 625 (FIG. 13B). Fold-shifts of EC50 values from antibody treatment curves relative to IL-2 alone were determined (FIG. 13C).

FIGS. 14A-14C show human PBMCs treated with various doses of IL-2 pre-complexed with a fixed 200 nM concentration of indicated antibodies for 24 hours. Samples were stained for $T_{reg}$ markers and CD69 expression and analyzed by flow cytometry gated on lymphocytes/CD3+CD4+/CD25+CD127-. MFI of CD69 was plotted against IL-2 concentration for donor 603 (FIG. 14A) and donor 625 (FIG. 14B). Fold-shifts of EC50 values from antibody treatment curves relative to IL-2 alone were determined (FIG. 14C).

DETAILED DESCRIPTION

Figure 1A:
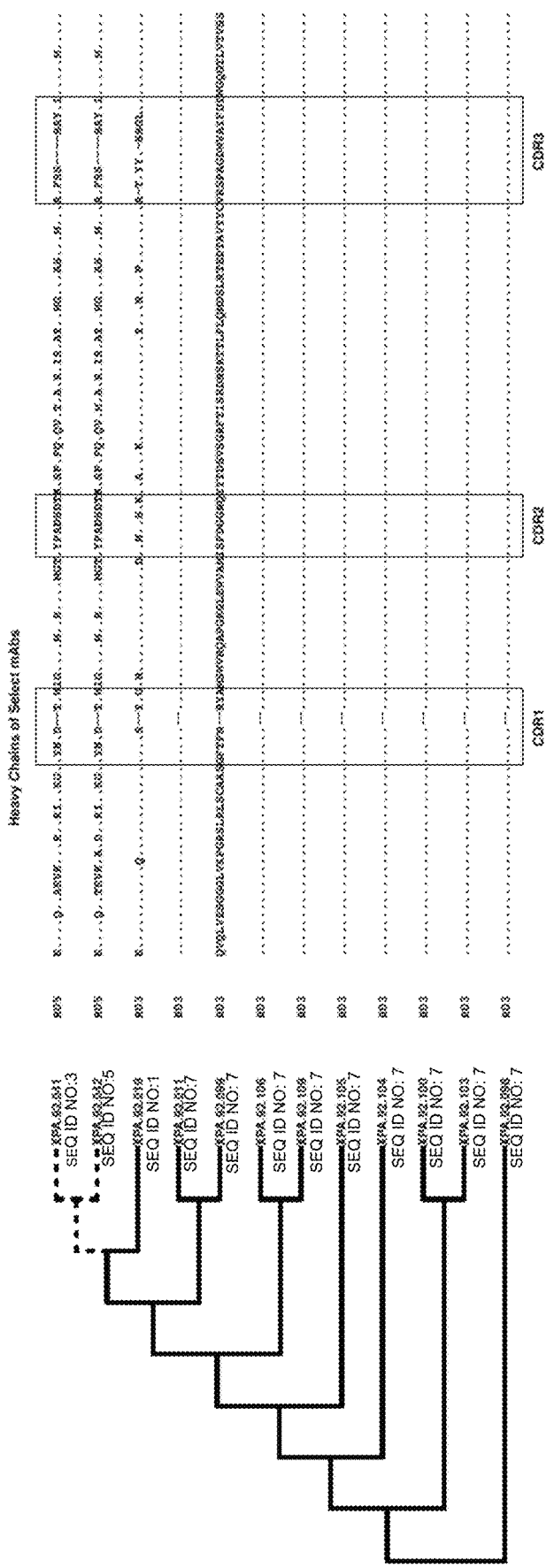
FIG. 1A and FIG. 1B show multiple sequence alignments of the heavy and light chains of selected clones against the sequence of XPA.92.099.
Figure 1B:
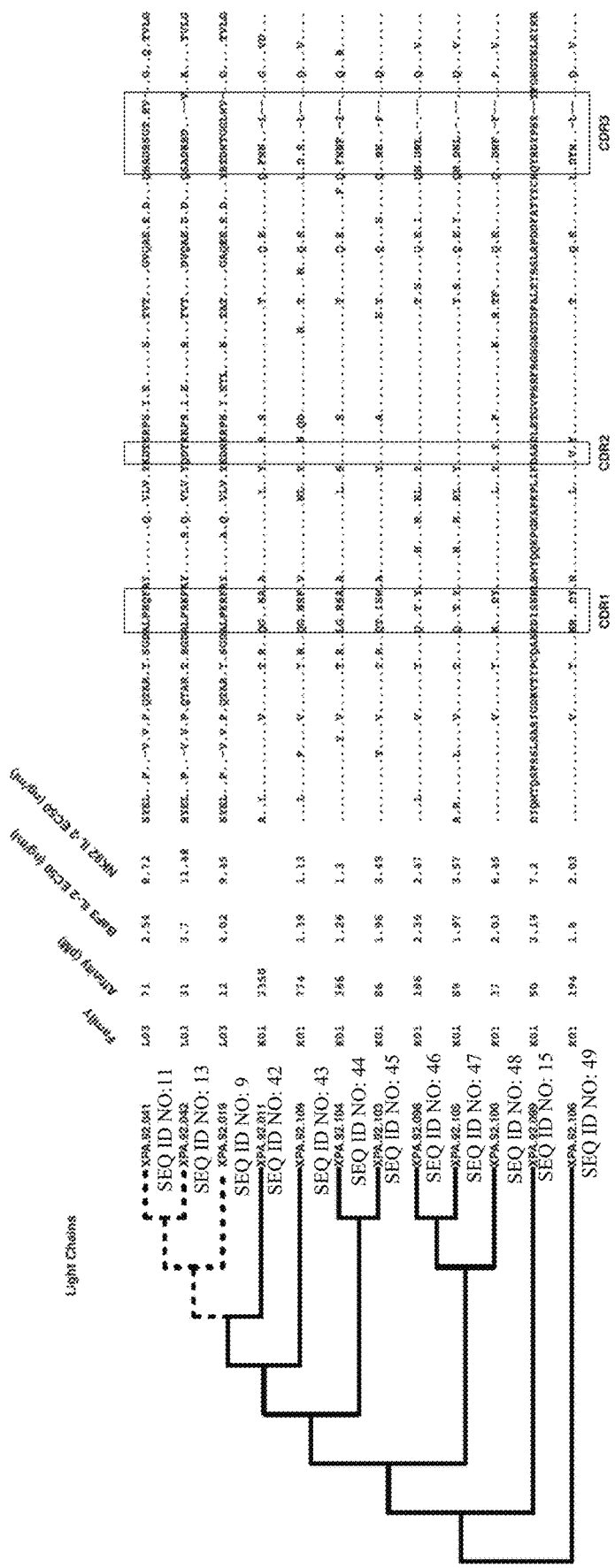

The invention provides materials, methods, and uses relating to human antibodies against interleukin-2 (IL-2). In particular, the present disclosure provides methods of use of such antibodies in the treatment of cancer.

The present disclosure provides molecules or agents that interact with IL-2 and modulate IL-2 activity, such as for example signaling through binding partners, IL-2 Rα, IL-2 Rαβγ and IL-2 Rβγ. The present disclosure provides therapeutics for treating cancer, microbial infection, asthma and autoimmune disease. The compositions disclosed herein advantageously have the ability to modulate immune cell activity in tumors, thereby providing, in one aspect, a method to treat cancer by affecting a cell population that directly or indirectly affects growth of the tumor.

Definitions

The terminology used herein is for the purpose of describing particular embodiments only and is not intended to be limiting.

"CHO" as used herein, refers to Chinese hamster ovary cells.

"CHO-K1" as used herein, refers to a subclone of the parental CHO cell line, which was derived from the ovary of an adult Chinese hamster.

"IL-2" as used herein, refers to interleukin-2.

"IL-2 R" as used herein, refers to interleukin-2 receptor. IL-2 R consists of three chains or subunits, IL-2 Rα (also known as CD25), IL-2 Rβ (also known as CD122), and the common gamma chain, γc (also known as CD132). The terms "IL-2Rβ and γc" is used interchangeably with the term "IL-2Rβγ" to refer to the IL-2R lacking the a subunit and comprising the β and γ subunits.

"$T_{reg}$" or "$T_{regs}$" as used herein, refer to regulatory T cells.

The term "antibody" is used in the broadest sense and includes fully assembled antibodies, tetrameric antibodies, monoclonal antibodies, polyclonal antibodies, multispecific antibodies (e.g., bispecific antibodies), antibody fragments that can bind an antigen (e.g., Fab', F'(ab)2, Fv, single chain antibodies, diabodies, Fcabs), and recombinant peptides comprising the forgoing as long as they exhibit the desired biological activity. An "immunoglobulin" or "tetrameric antibody" is a tetrameric glycoprotein that consists of two heavy chains and two light chains, each comprising a variable region and a constant region. Antigen-binding portions may be produced by recombinant DNA techniques or by enzymatic or chemical cleavage of intact antibodies. Antibody fragments or antigen-binding portions include, inter alia, Fab, Fab', F(ab')2, Fv, domain antibody (dAb), complementarity determining region (CDR) fragments, CDR-grafted antibodies, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), an antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, such as one, two, three, four, five or six CDR sequences, as long as the antibody retains the desired biological activity.

An "immunoglobulin" or "native antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa (κ) and lambda (λ) light chains. Heavy chains are classified as mu (μ), delta (Δ), gamma (γ), alpha (α), and epsilon (ε), and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology*, Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

"Heavy chain variable region" as used herein refers to the region of the antibody molecule comprising at least one complementarity determining region (CDR) of said antibody heavy chain variable domain. The heavy chain variable region may contain one, two, or three CDRs of said antibody heavy chain.

"Light chain variable region" as used herein refers to the region of an antibody molecule, comprising at least one complementarity determining region (CDR) of said antibody light chain variable domain. The light chain variable region may contain one, two, or three CDRs of said antibody light chain, which may be either a kappa or lambda light chain depending on the antibody.

"Monoclonal antibody" refers to an antibody obtained from a population of substantially homogeneous antibodies, i.e., the individual antibodies comprising the population are identical except for possible naturally occurring mutations that may be present in minor amounts.

"Antibody variant" as used herein refers to an antibody polypeptide sequence that contains at least one amino acid substitution, deletion, or insertion in the variable region of the reference antibody variable region domains. Variants may be substantially homologous or substantially identical to the unmodified antibody.

A "chimeric antibody," as used herein, refers to an antibody containing sequence derived from two different antibodies (see, e.g., U.S. Pat. No. 4,816,567) which typically originate from different species. Most typically, chimeric antibodies comprise human and rodent antibody fragments, generally human constant and mouse variable regions.

A "neutralizing antibody" is an antibody molecule which is able to eliminate or significantly reduce a biological function of a target antigen to which it binds. Accordingly, a "neutralizing" anti-target antibody is capable of eliminating or significantly reducing a biological function, such as enzyme activity, ligand binding, or intracellular signaling.

An "isolated" antibody is one that has been identified and separated and recovered from a component of its natural environment. Contaminant components of its natural environment are materials that would interfere with diagnostic or therapeutic uses for the antibody, and may include enzymes, hormones, and other proteinaceous or non-proteinaceous solutes. In various embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, an antibody that "specifically binds" is "target specific", is "specific for" target or is "immunoreactive" with the target antigen refers to an antibody or antibody substance that binds the target antigen with greater affinity than with similar antigens. In one aspect of the disclosure, the target-binding polypeptides, or fragments, variants, or derivatives thereof, will bind with a greater affinity to human target as compared to its binding affinity to target of other, i.e., non-human, species, but binding polypeptides that recognize and bind orthologs of the target are within the scope provided.

For example, a polypeptide that is an antibody or fragment thereof "specific for" its cognate antigen indicates that the variable regions of the antibodies recognize and bind the polypeptide of interest with a detectable preference (i.e., able to distinguish the polypeptide of interest from other known polypeptides of the same family, by virtue of measurable differences in binding affinity, despite the possible existence of localized sequence identity, homology, or similarity between family members). It will be understood that specific antibodies may also interact with other proteins (for example, S. aureus protein A or other antibodies in ELISA techniques) through interactions with sequences outside the variable region of the antibodies, and in particular, in the constant region of the molecule. Screening assays to determine binding specificity of an antibody for use in the methods of the present disclosure are well known and routinely practiced in the art. For a comprehensive discussion of such assays, see Harlow et al., (Eds), Antibodies A Laboratory Manual; Cold Spring Harbor Laboratory; Cold Spring Harbor, NY (1988), Chapter 6. Antibodies for use in the methods can be produced using any method known in the art.

The term "epitope" refers to that portion of any molecule capable of being recognized by and bound by a selective binding agent such as an antibody at one or more of the antigen binding regions. Epitopes usually consist of chemically active surface groupings of molecules, such as, amino acids or carbohydrate side chains, and have specific three-dimensional structural characteristics as well as specific charge characteristics. Epitopes as used herein may be contiguous or non-contiguous. Moreover, epitopes may be mimetic (mimotopes) in that they comprise a three dimensional structure that is identical to the epitope used to generate the antibody, yet comprise none or only some of the amino acid residues found in the target that were used to stimulate the antibody immune response. As used herein, a mimotope is not considered a different antigen from the epitope bound by the selective binding agent; the selective binding agent recognizes the same three-dimensional structure of the epitope and mimotope.

The term "derivative" when used in connection with antibody substances and polypeptides of the present disclosure refers to polypeptides chemically modified by such techniques as ubiquitination, conjugation to therapeutic or diagnostic agents, labeling (e.g., with radionuclides or various enzymes), covalent polymer attachment such as PEGylation (derivatization with polyethylene glycol) and insertion or substitution by chemical synthesis of amino acids such as ornithine, which do not normally occur in human proteins. Derivatives retain the binding properties of underivatized molecules of the disclosure.

The term "therapeutically effective amount" is used herein to indicate the amount of target-specific composition of the disclosure that is effective to ameliorate or lessen symptoms or signs of disease to be treated.

The terms "treat", "treated", "treating" and "treatment", as used with respect to methods herein refer to eliminating, reducing, suppressing or ameliorating, either temporarily or permanently, either partially or completely, a clinical symptom, manifestation or progression of an event, disease or condition. Such treating need not be absolute to be useful.

The present methods provides for use of target-specific antibodies, which may comprise those exemplary sequences set out herein, fragments, variants and derivatives thereof, pharmaceutical formulations including target-specific antibodies recited herein. Depending on the amino acid sequence of the constant domain of their heavy chains, immunoglobulins can be assigned to different classes, IgA, IgD, IgE, IgG and IgM, which may be further divided into subclasses or isotypes, e.g. IgG1, IgG2, IgG3, IgG4, IgA1 and IgA2. The subunit structures and three-dimensional configurations of different classes of immunoglobulins are well known. Different isotypes have different effector functions; for example, IgG1 and IgG3 isotypes have ADCC activity. An antibody disclosed herein, if it comprises a constant domain, may be of any of these subclasses or isotypes.

The present disclosure provides a target-specific antibody, which may comprise those exemplary sequences set out in, FIGS. 12A-12E fragments, variants and derivatives thereof, pharmaceutical formulations including a target-specific antibody recited above, methods of preparing the pharmaceutical formulations, and methods of treating patients with the pharmaceutical formulations and compounds. The antibodies described herein and used in the present methods may exhibit binding affinity to one or more IL-2 antigens of a $K_D$ of less than or equal to about $2 \times 10^{-9}$ M, or about $1 \times 10^{-10}$ M, or less than or equal to about $10^{-10}$ M, $10^{-11}$ M, 10-12 M, or $10^{-13}$ M or less, or from $10^{-10}$ to $10^{-13}$ M. Such affinities may be readily determined using conventional techniques, such as by equilibrium dialysis; by using surface plasmon resonance (SPR) technology (e.g., the BIAcore 2000 instrument, using general procedures outlined by the manufacturer); by radioimmunoassay using $^{125}$I labeled target antigen; or by another method set forth in the examples below or known to the skilled artisan. The affinity data may be analyzed, for example, by the method of Scatchard et al., (Ann NY, Acad. Sci., 51:660, 1949).

A KinExA kinetic exclusion assay is also useful to measure the affinity of an antibody for its antigen. KinExA technology measures binding events in the solution phase, rather than binding events between a solution phase and a solid phase. In addition, while many methods for measuring binding events require at least one reactant be modified through immobilization or labeling, the KinExA method does not require modification of molecules under study. The KinExA method is believed to allow a wider range of binding constants to be measured than other methods currently available. Additional description about KinExA devices and operation for antibody characterization is available from the manufacturer (Sapidyne Instruments, Inc., Boise, ID) and can be found in the published literature, for example U.S. Pat. No. 6,664,114 and Darling et al., "Kinetic Exclusion Assay Technology: Characterization of Molecular Interactions" Assay and Drug Development Technologies, 2:647-657 (2004).

Interleukin 2 (IL-2)

Interleukin-2 (IL-2) is a 15 kDa peptide that is a member of the four-α helix bundle family of cytokines (Wang et al., Annual review of immunology 27, 29-60 (2009)). Originally identified in 1976 as a T cell growth factor, it has been described by a variety of names, including T-cell growth factor (TCGF), lymphocyte-conditioned medium (LCM) factor, T-cell mitogenic factor (TMF), killer helper factor (KHF), and T-cell replacing factor (TRF)(Lotze M T, Interleukin-2, In Human Cytokines: Handbook for basic and clinical research, pp 81-96(1992); Smith et al., Cytokine Reference, pp 113-125 (2001)). IL-2 is produced primarily by activated CD4+ T-cells, secondarily by activated CD8+ T cells, and to a lesser extent by activated dendritic cells (DCs), natural killer (NK) cells, and natural killer T (NKT) cells. IL-2 is rapidly and transiently produced upon engaging the TCR and costimulatory molecules such as CD28 on naive T cells. The transient nature of IL-2 secretion depends on transcriptional induction by TCR signals and stabilization of IL-2 mRNA by costimulatory signals, followed by transcriptional silencing of the IL-2 gene and rapid degradation of IL-2 mRNA. A classical auto-regulatory feedback loop has recently been described in which IL-2 inhibits its own production (Malek T R, *Annual review of immunology* 26, 453-479 (2008)).

Originally considered primarily an immune stimulatory factor, later studies revealed a role in immune tolerance as well (Malek T R, *Annual review of immunology* 26, 453-479 (2008)). It is now widely accepted that IL-2 has a complex role, contributing to immune activation, specific memory and maintenance of immune tolerance (Waldmann T, *Arthritis research* 4 (3) S161-167 (2002); Bachmann and Oxenius, *EMBO reports* 8, 1142-1148 (2007)). The particular effect of IL-2 stimulation depends on biological context, including for example such factors as presence of helper T-cells, co-stimulation through CD28 signaling, and suppression by regulatory T-cells. Part of this biological context is mediated through differential expression of the three IL-2 receptor chains on different cell types and under different conditions such as acute antigen stimulation or chronic infection. In addition, IL-2 and its receptors are regulated by both positive and negative feedback mechanisms (Boyman and Sprent, *Nat Rev Immunol* 12, 180-190 (2012)).

IL-2 Muteins

IL-2 variants (muteins) may have improved therapeutic effects compared to wild-type IL-2. IL-2 muteins with decreased binding affinity to IL-2 Rβ, such as BAY 50-4798 (containing an N88R mutation of IL-2) and Selectikine (harboring a D20T mutation of IL-2) have been generated (Shanafelt et al, *Nat. Biotechnol.* 19: 1197-1202 (2000); Laurent et al, J. Transl. Med. 11,5 (2013). However, when tested in clinical trials, these IL-2 muteins did not show decreased toxicity in patients. IL-2 muteins with decreased affinity to IL-2 Rα (such as 'no-α mutein' GA501, and GA504 have been generated (Carmenate et al, J. Immunol. 190: 6230-38 (2013); Klein et al, Cancer Res. 73, 486 (2013)). Agonistic IL-2 muteins H9 and D10 (also known as IL-2 superkines) associate with IL-2 Rβ with 200-fold increased affinity and efficiently bound dimeric IL-2Rs without the need for IL-2 Rα; such binding resulted in increased STAT5 phosphorylation and cell proliferation in vitro and in vivo (Levin et al, Nature 484: 529-33 (2012)). An H9 mutant, H9-RETR, was engineered by introducing four mutations into H9 (L18R, Q22E, Q126T, and S130R) and retained IL-2 Rβ binding but demonstrated significantly decreased affinity to γc (Mitra et al, Immunity 42: 815-25). IL-2 muteins are also described in WO2014/100014, WO2015164815, WO205/118016, WO2016/030350, U.S. Pat. Nos. 8,759,486, and 9,266,938.

Interleukin 2 Receptors (IL-2 R)

The receptor for IL-2 consists of three chains, IL-2 Ra (also known as CD25), IL-2 Rβ (also known as CD122), and the common gamma chain, γc (also known as CD132). The three receptor chains are expressed separately and differently on various cell types. IL-2 signals through interactions between IL-2 Rβ and γc that activate cellular pathways such as the Jak/Stat, PI3K-AKT, and MAPK pathways. Higher sensitivity to IL-2 is conferred through interaction with IL-2 Rα, which can independently bind IL-2 and promote association with the other two chains to form a high affinity trimeric receptor complex (Malek T R, *Annual review of immunology* 26, 453-479 (2008)). IL-2 Rα, also called the Tac antigen, is specific for IL-2, while IL-2 Rβ is utilized by both IL-2 and IL-15, and is sometimes referred to as the common β chain. IL-2 Rγ, also known as the common γ chain, is shared by a number of cytokines, including IL-2, IL-4, IL-7, IL-9, IL-15 and IL-21 (Malek T R, *Annual review of immunology* 26, 453-479 (2008); Smith K A, *Cytokine Reference, pp* 1459-1469 (2001); Boyman and Sprent *Nat Rev Immunol* 12, 180-190 (2012)).

IL-2 as a Therapeutic

A recombinant, modified version of IL-2 (aldesleukin) was approved by the US FDA for treatment of metastatic renal cell carcinoma (RCC) in 1992, and metastatic melanoma (MM) in 1998. It has been shown to be efficacious in improving survival in a subset of patients, leading to durable, complete, and apparently curative regressions in a small percentage of patients (Dutcher et al., *Journal for Immunotherapy of Cancer* 2(26) (2014); Rosenberg S A, J Immunol 192, 5451-5458 (2014)). At the same time, the majority of patients experience severe side effects, often including vascular leak syndrome (VLS), pulmonary edema, hypotension, renal damage, CNS impairment, and cardiac effects. Although most side effects may be reversible, the need for management of the treatment requires hospitalization at expert immunotherapy centers; this, along with strict eligibility requirements for acceptance into treatment, limits utilization of aldesleukin (Dutcher et al., *Journal for Immunotherapy of Cancer* 2(26) (2014)). Another shortcoming of aldesleukin treatment is the requirement for multiple intravenous doses over 5 days for several weeks, due to rapid renal clearance resulting in short half-life of administered IL-2.

Recent advances in the understanding of the multiple roles of IL-2 and their underlying mechanisms and interplay has helped to explain the seemingly paradoxical effects of IL-2 activities. For example regulatory T-cells express high levels of IL-2 Rα (CD25), making them sensitive to low levels of IL-2. Thus treatment with low concentration IL-2 is more likely to stimulate the suppressive pathways, rather than effector T-cells, which express little IL-2 Rα before activation. In addition to providing immune suppression, the regulatory T-cells may also provide a sink for IL-2, further reducing the probability that effector T-cells will be activated. Together, these effects may contribute to reduced response rates and may explain the requirement for high-doses of IL-2 treatment to achieve anti-tumor responses (Boyman and Sprent, Nature reviews. Immunology 12, 180-190 (2012)). Finally, researchers have reported expression of IL-2 receptors on pulmonary endothelial cells, which may lead direct effects of IL-2 on these cell types. It has been proposed that the high doses of IL-2 required for therapeutic benefit are able to activate the low levels of IL-2 receptors on endothelial cells, which could contribute to the damage that results in VLS, pulmonary edema, and hypotension (Boyman and Sprent, Nature review: Immunology 12, 180-190 (2012); Rafi-Janajreh et al., *J Immunol* 163, 1619-1627 (1999); Krieg et al., PNAS 107, 11906-11911 (2010); Downie et al., *American journal of respiratory cell and molecular biology* 7, 58-65 (1992)).

Multiple approaches have been suggested and tested as potential improvements in IL-2 based immunotherapies for oncology, including 1) engineering of IL-2 to either reduce (Shanafelt et al., *Nature biotechnology* 18, 1197-1202 (2000)) or increase (Levin et al., *Nature* 484, 529-533 (2012)) its interaction with IL-2 Rβγ, or to reduce its interaction with IL-2 Rα (Charych et al., *Clin Cancer Res* 22, 680-690 (2016), U.S. Pat. No. 9,266,938); 2) increasing half-life with IL-2 fusions or conjugation (WO 2012/065086; WO 2013/177187; WO 2015/118016); 3) enhancing IL-2 treatment using anti-receptor antibodies (WO 2008/003473); 4) conjugating IL-2 to an antibody that targets cancer antigens (WO 2016/030350; Sujomoto et al., *Anticancer Res.* 34(1), 89-97 (2014)); 5) fusing IL-2 with IL-2 Rα (WO 2016/022671); and 6) use of anti-IL-2 antibodies that modulate IL-2 activity (Boyman et al., *Science* 311, 1924-1927 (2006); Letourneau et al., *PNAS* 107, 2171-2176 (2010); Spangler et al., *Immunity* 42, 815-825 (2015); Tomala and Kovar, *Oncoimmunology* 5 (2016)) (US Patent Publication Nos. 20100310501 and 20130142755; WO 2007/095643; WO 2014/108748; WO 2015/109212; WO 2016005950). While multiple reports of anti-IL-2 antibodies have been published that modulate IL-2 interaction with IL-2 receptors, these have described mouse anti-human IL-2 or anti-murine IL-2 to show proof of the concept of this promising approach (Krieg et al., *PNAS* 107, 11906-11911 (2010); Boyman et al., *Science* 311, 1924-1927 (2006); Letourneau et al., *PNAS* 107, 2171-2176 (2010)) (US Patent Publication No. 20130142755). Ideally, therapeutic antibodies are human in origin, while antibodies humanized from murine or other species may also be acceptable. Use of surrogate antibodies introduces the risk of subtle differences in binding properties that may not completely recapitulate the activity of the ultimate therapeutic candidates. Multiple studies have highlighted the functional consequences of differences in epitopes of these antibodies (Su et al., *Science translational medicine* 7, 311 (2015); Rojas et al., *Immunobiology* 218, 105-113 (2013); Garcia-Martinez et al., *International immunology* 24, 427-446 (2012)).

Antibodies

As stated above, an "immunoglobulin" or "native antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Chothia et al., *J. Mol. Biol.* 196:901-917, 1987).

Immunoglobulin variable domains exhibit the same general structure of relatively conserved framework regions (FR) joined by three hypervariable regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk, *J. Mol. Biol.* 196:901-917, 1987; Chothia et al., *Nature* 342:878-883, 1989.

The hypervariable region of an antibody refers to the CDR amino acid residues of an antibody which are responsible for antigen-binding. The hypervariable region comprises amino acid residues from a CDR [e.g., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)] and/or those residues from a hypervariable loop (e.g., residues 26-32 (L1), 50-52 (L2) and 91-96 (L3) in the light chain variable domain and 26-32 (H1), 53-55 (H2) and 96-101 (H3) in the heavy chain variable domain as described by [Chothia et al., *J. Mol. Biol.* 196:901-917 (1987)]. CDRs have also been identified and numbered according to ImMunoGenTics (IMGT) numbering (Lefranc, M.-P., The Immunologist, 7, 132-136 (1999); Lefranc, M.-P. et al., *Dev. Comp. Immunol.*, 27, 55-77 (2003), which describes the CDR locations in the light and heavy chain variable domains as follows: CDR1, approximately residues 27 to 38; CDR2, approximately residues 56 to 65; and, CDR3, approximately residues 105 to 116 (germline) or residues 105 to 117 (rearranged). In one embodiment, it is contemplated that the CDRs are located at approximately residues 26-31 (L1), 49-51 (L2) and 88-98 (L3) in the light chain variable domain and approximately residues 26-33 (H1), 51-58 (H2) and 97-110 (H3) in the heavy chain variable domain of an antibody heavy or light chain of approximately similar length to those disclosed herein. However, one of skill in the art understands that the actual location of the CDR residues may vary from the projected residues described above when the sequence of the particular antibody is identified.

Framework or FR residues are those variable domain residues other than the hypervariable region residues.

Monoclonal antibody refers to an antibody obtained from a population of substantially homogeneous antibodies in which all antibodies in the mixture have a single amino acid sequence, derived from a single clone. Monoclonal antibodies are generally highly specific, and are directed against a single antigenic site, or epitope. In contrast, polyclonal antibody preparations typically include a mixture of antibodies with diverse amino acid sequences, directed against the same or different determinants (epitopes). In addition to their specificity, monoclonal antibodies are advantageous in that they are synthesized in the homogeneous culture, uncontaminated by other immunoglobulins with different specificities and characteristics.

As described below, antibodies, including monoclonal, human, humanized, and other antibodies described herein, contemplated herein are typically generated recombinantly or through other methods of manipulating the genetic code in vitro or in vivo, and are therefore not necessarily reflective of a particular antibody that is found in nature.

Monoclonal antibodies may be made by the hybridoma method first described by Kohler et al. (*Nature*, 256:495-7, 1975) (Harlow & Lane; Antibodies: A Laboratory Manual, Cold Spring Harbor Laboratory Press: Cold Spring Harbor, N.Y. (1988); Goding, *Monoclonal Antibodies: Principles and Practice*, pp. 59-103 (Academic Press, 1986), or may be made by recombinant DNA methods (see, e.g., U.S. Pat. No. 4,816,567). The monoclonal antibodies may also be isolated from phage antibody libraries using the techniques described in, for example, Clackson et al., (*Nature* 352:624-628, 1991) and Marks et al., (*J. Mol. Biol.* 222:581-597,1991). Additional methods for producing monoclonal antibodies are well-known to a person of ordinary skill in the art.

Monoclonal antibodies, such as those produced by the above methods, are suitably separated from culture medium, ascites fluid, or serum by conventional immunoglobulin purification procedures such as, for example, protein A-Sepharose, hydrophobic interaction chromatography (HIC), ion exchange chromatography, hydroxyapatite chromatography, gel electrophoresis, dialysis, and/or affinity chromatography.

IL-2 Antibodies

The present disclosure encompasses use of amino acid molecules encoding target specific antibodies. Fully human anti-human IL-2 antibodies were generated from phage display libraries. The IL-2 antibodies, described herein, differentially modulate interaction of human IL-2 with different IL-2 receptor chains. Specifically, the goal was to identify antibodies capable of preventing or reducing interaction of IL-2 with IL-2 Rα, while remaining permissive to IL-2 Rβ and γc binding and signaling. To achieve this, a novel screening approach was conceived using cells engineered to express different combinations of human IL-2 receptor chains to identify anti-ligand antibodies that would be predicted to possess differential IL-2-modulating properties. Using a flow-cytometry based screen, antibodies were stratified based on their effects on IL-2 restriction or permissiveness on binding the engineered cell lines. Antibodies of interest were also complexed with IL-2 and tested in functional assays using IL-2 dependent cell lines that either express all three receptor chains or only IL-2 Rβ and γc. In vivo testing verified that antibodies with different patterns of activity on these cell lines mediate differential effects on T-cell subsets in mice. Surprisingly, antibodies that resulted in the strongest difference in preferentially stimulating CD8+ over CD4+ T-cells in vivo possessed a hybrid pattern of receptor binding permissiveness, e.g., the antibodies that do not completely block IL-2 Rα binding resulted in a greater CD8+/CD4+ ratio of T cells after in vivo treatment than those antibodies that completely blocked IL-2 Rα binding. Also unexpected was the finding that the antibodies that gave the greatest shift in CD8+/CD4+ T cells had a small degree of inhibition of signaling in IL-2 Rβγ cells. Testing complexes of hIL-2 with these antibodies in oncology models, both alone and in combination with other immune modulating antibodies, further validated their potential as immunotherapeutic agents.

In some embodiments, the amino acid sequence of the human anti-target antibody comprises one or more CDRs of the amino acid sequence of the mature (i.e., missing signal sequence) light chain variable region (VL) of antibodies XPA.92.019, XPA.92.041, XPA.92.042 or XPA.92.099 set out in FIGS. 12A-12E or SEQ ID NOs: 9, 11, 13, or 15 or variants thereof, including humanized antibodies or any other variants described herein. In some embodiments, the VL comprises the amino acid sequence from the beginning of the CDR1 to the end of the CDR3 of the light chain of any one of the foregoing antibodies.

In one embodiment, the target specific antibody comprises a light chain CDR1, CDR2 or CDR3 (LCDR1, LCDR2, LCDR3), each of which are independently selected from the CDR1, CDR2 and CDR3 regions of an antibody having a light chain variable region comprising the amino acid sequence of the VL region set out in SEQ ID NOs: 9, 11, 13, or 15, a nucleic acid encoding the VL region set out in SEQ ID NOs: 9, 11, 13, or 15, or encoded by a nucleic acid molecule encoding the VL region set out in SEQ ID NOs: 10, 12, 14, or 16.

In some embodiments, the amino acid sequence of the human anti-target antibody comprises one or more CDRs of the amino acid sequence of the mature (i.e., missing signal sequence) heavy chain variable region (VH) of antibodies XPA.92.019, XPA.92.041, XPA.92.042 or XPA.92.099 set out in FIGS. 12A-12E or SEQ ID NOs: 1, 3, 5, or 7, or variants thereof, including humanized antibodies or any other variants described herein. In some embodiments, the VH comprises the amino acid sequence from the beginning of the CDR1 to the end of the CDR3 of the heavy chain of any one of the foregoing antibodies.

In one embodiment, the target specific antibody comprises a heavy chain CDR1, CDR2 or CDR3 (HCDR1, HCDR2, HCDR3), each of which are independently selected from the CDR1, CDR2 and CDR3 regions of an antibody having a heavy chain variable region comprising the amino acid sequence of the VH region set out in SEQ ID NOs: 1, 3, 5, or 7, a nucleic acid encoding the VH region set out in SEQ ID NOs: 1, 3, 5, or 7, or encoded by a nucleic acid molecule encoding the VH region set out in SEQ ID NOs: 2, 4, 6, or 8.

A polypeptide of the target specific antibody may comprise the CDR1, CDR2 and CDR3 regions of an antibody comprising the amino acid sequence of the VH region selected from the group consisting of XPA.92.019, XPA.92.041, XPA.92.042 or XPA.92.099.

In another embodiment, the antibody comprises a mature light chain variable region as disclosed above and a mature heavy chain variable region as disclosed above, optionally paired as set forth in FIGS. 12A-12E.

In exemplary embodiments, the disclosure contemplates: a monoclonal antibody that retains any one, two, three, four, five, or six of HCDR1, HCDR2, HCDR3, LCDR1, LCDR2, or LCDR3 of any one of SEQ ID NOs: 17, 18, and 20-41, respectively, optionally including one or two mutations in any of such CDR(s), e.g., a conservative or non-conservative substitution, and optionally paired as set forth in FIG. 12; a monoclonal antibody that retains all of HCDR1, HCDR2, HCDR3, or the heavy chain variable region of any one of SEQ ID NOs: 17, 18, 20-28 and 41, optionally including one or two mutations in any of such CDR(s), optionally further comprising any suitable heavy chain constant region, e.g., lgG1, lgG2, lgG3, lgG4, IgM, IgA1, IgA2, or lgE, a human sequence thereof, or a hybrid thereof; a monoclonal antibody that retains all of LCDR1, LCDR2, LCDR3, or the light chain variable region of any one SEQ ID NOs: 29-40, optionally including one or two mutations in any of such CDR(s), optionally further comprising any suitable light chain constant region, e.g., a kappa or lambda light chain constant region, a human sequence thereof, or a hybrid thereof.

In some embodiments, the antibody comprises all three light chain CDRs, all three heavy chain CDRs, or all six CDRs of the light and heavy chain, paired as set forth in FIGS. 12A-12E. In some exemplary embodiments, two light chain CDRs from an antibody may be combined with a third light chain CDR from a different antibody. Alternatively, a LCDR1 from one antibody can be combined with a LCDR2 from a different antibody and a LCDR3 from yet another antibody, particularly where the CDRs are highly homologous. Similarly, two heavy chain CDRs from an antibody may be combined with a third heavy chain CDR from a different antibody; or a HCDR1 from one antibody can be combined with a HCDR2 from a different antibody and a HCDR3 from yet another antibody, particularly where the CDRs are highly homologous.

In some embodiments, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the heavy chain variable region set out in SEQ ID NOs: 1, 3, 5, or 7 and/or an amino acid sequence an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the light chain variable region set out in SEQ ID NOs: 9, 11, 13, or 15, the antibody further comprising at least one, two, three, four, five or all of HCDR1, HCDR2, HCDR3, LCDR1, LCDR2 or LCDR3. In some embodiments, the amino acid sequence with percentage identity to the light chain variable region may comprise one, two or three of the light chain CDRs. In other embodiments, the amino acid sequence with percentage identity to the heavy chain variable region may comprise one, two, or three of the heavy chain CDRs.

In another embodiment, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to all three HCDRs in the heavy chain variable region of an antibody sequence in FIG. 12 or the CDRs set out in SEQ ID NOs: 17, 18, 20-28 and 41.

In a related embodiment, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the all three LCDRs in the light chain variable region of an antibody sequence in FIGS. 12A-12E or the CDRs set out in SEQ ID NOs: 29-40.

In a further embodiment, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the all six CDRs in the heavy chain and light chain variable regions of an antibody sequence in FIG. 12 or the CDRs set out in SEQ ID NOs: 17, 18 and 20-41.

It is contemplated that the antibodies of the disclosure may have one, or two or more amino acid substitutions in the CDR regions of the antibody, e.g., non-conservative or conservative substitutions.

In a related embodiment, the residues of the framework are altered. The heavy chain framework regions which can be altered lie within regions designated H-FR1, H-FR2, H-FR3 and H-FR4, which surround the heavy chain CDR residues, and the residues of the light chain framework regions which can be altered lie within the regions designated L-FR1, L-FR2, L-FR3 and L-FR4, which surround the light chain CDR residues. An amino acid within the framework region may be replaced, for example, with any suitable amino acid identified in a human framework or human consensus framework.

Heavy and light chain amino acid sequences of XPA.92.019 are set out in SEQ ID NOs: 1 and 9 respectively. Heavy and light chain amino acid sequences of XPA.92.041 are set out in SEQ ID NOs: 3 and 11 respectively. Heavy and light chain amino acid sequences of XPA.92.042 are set out in SEQ ID NOs: 5 and 13, respectively and heavy and light chain amino acid sequences of XPA.92.099 are set out in SEQ ID NOs: 7 and 15, respectively.

In various embodiments, when the antibody is complexed with IL-2 and injected into a mammalian host the complex leads to expansion of one or more of CD8+ T cells, NK cells, NK T cells, CD4+ T cells, tumor-reactive CD8+ T cells or tumor-reactive CD4+ T Cells.

In various embodiments, an antibody described herein induces a conformational change in IL-2 that affects receptor subunit usage or biological activity.

It is further contemplated that antibodies of the present disclosure may be used as smaller antigen binding fragments of the antibody that are well-known in the art and described herein.

Antibody Fragments

Antibody fragments comprise a portion of an intact full length antibody, preferably an antigen binding or variable region of the intact antibody. Examples of antibody fragments include Fab, Fab', F(ab')2, Fcab, and Fv fragments; diabodies; linear antibodies; single-chain antibody molecules (e.g., scFv); multispecific antibody fragments such as bispecfic, trispecific, etc. antibodies (e.g., diabodies, triabodies, tetrabodies); minibody; chelating recombinant antibody; tribodies or bibodies; intrabodies; nanobodies; small modular immunopharmaceuticals (SMIP), binding-domain immunoglobulin fusion proteins; camelized antibodies; VHH containing antibodies; and other polypeptides formed from antibody fragments. See for example Holliger & Hudson, 2005 *Nat. Biotech.* 23:1126-36; Eyer & Hruska, *Veterinarni Medicina* 57:439-513, 2012.

Papain digestion of antibodies produces two identical antigen-binding fragments, called "Fab" fragments, monovalent fragments consisting of the VL, VH, CL and CH1 domains each with a single antigen-binding site, and a residual "Fc" fragment, whose name reflects its ability to crystallize readily. Pepsin treatment yields a F(ab')2 fragment, a bivalent fragment comprising two Fab fragments linked by a disulfide bridge at the hinge region. "Single-chain Fv" or "scFv" antibody fragments comprise the VH and VL domains of antibody joined by a linker peptide, wherein these domains are present in a single polypeptide chain. Preferably, the Fv polypeptide further comprises a polypeptide linker between the VH and VL domains that enables the Fv to form the desired structure for antigen binding, resulting in a single-chain antibody (scFv), in which a VL and VH region are paired to form a monovalent molecule via a synthetic linker that enables them to be made as a single protein chain (Bird et al., Science 242:423-426, 1988, and Huston et al., *PNAS* 85:5879-5883, 1988). For a review of scFv see Pluckthun, in The Pharmacology of Monoclonal Antibodies, vol. 1 13, Rosenburg and Moore eds., Springer-Verlag, New York, pp. 269-315 (1994). An Fd fragment consists of the VH and CH1 domains.

Additional antibody fragments include a domain antibody (dAb) fragment (Ward et al., *Nature* 341:544-546, 1989) which consists of a VH domain. Diabodies are bivalent antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., *PNAS* 90:6444-6448, 1993, and Poljak et al., Structure 2:1121-1123, 1994). Diabodies can be bispecific or monospecific.

Functional heavy-chain antibodies devoid of light chains are naturally occurring in nurse sharks (Greenberg et al., *Nature* 374:168-73, 1995), wobbegong sharks (Nuttall et al., *Mol Immunol.* 38:313-26, 2001) and Camelidae (Hamers-Casterman et al., *Nature* 363:446-8, 1993; Nguyen et al., *J. Mol. Biol.* 275:413, 1998), such as camels, dromedaries, alpacas and llamas. The antigen-binding site is reduced to a single domain, the VHH domain, in these animals. These antibodies form antigen-binding regions using only heavy chain variable region, i.e., these functional antibodies are homodimers of heavy chains only having the structure H2L2 (referred to as "heavy-chain antibodies" or "HCAbs"). Camelid VHH reportedly recombines with IgG2 and IgG3 constant regions that contain hinge, CH2, and CH3 domains and lack a CH1 domain (Hamers-Casterman et al., supra). For example, llama IgG1 is a conventional (H2L2) antibody isotype in which VH recombines with a constant region that contains hinge, CH1, CH2 and CH3 domains, whereas the llama IgG2 and IgG3 are heavy chain-only isotypes that lack CH1 domains and that contain no light chains. Camelid VHH domains have been found to bind to antigen with high affinity (Desmyter et al., *J. Biol. Chem.* 276:26285-90, 2001) and possess high stability in solution (Ewert et al., *Biochem-* istry 41:3628-36, 2002). Classical VH-only fragments are difficult to produce in soluble form, but improvements in solubility and specific binding can be obtained when framework residues are altered to be more VHH-like. (See, e.g., Reichman, et al., *J Immunol Methods* 1999, 231:25-38). Methods for generating antibodies having camelid heavy chains are described in, for example, in U.S. Patent Publication Nos. 20050136049 and 20050037421.

The variable domain of an antibody heavy-chain, a fully functional antigen-binding fragment with a molecular mass of only 15 kDa, is referred to as a nanobody (Cortez-Retamozo et al., Cancer Research 64:2853-57, 2004). A nanobody library may be generated from an immunized dromedary as described in Conrath et al., (*Antimicrob Agents Chemother* 45:2807-12, 2001) or using recombinant methods as described in Revets et al., *Expert Opin. Biol. Ther.* 5(1):111-24 (2005).

Production of bispecific Fab-scFv ("bibody") and trispecific Fab-(scFv)(2) ("tribody") are described in Schoonjans et al. (J Immunol. 165:7050-57, 2000) and Willems et al. (J Chromatogr B Analyt Technol Biomed Life Sci. 786:161-76, 2003). For bibodies or tribodies, a scFv molecule is fused to one or both of the VL-CL (L) and VH-CH1 (Fd) chains, e.g., to produce a tribody two scFvs are fused to C-term of Fab while in a bibody one scFv is fused to C-term of Fab. Additional Fab-based bispecific formats are described in Wu et al., mAbs 7: 470-482, 2015.

A "minibody" consisting of scFv fused to CH3 via a peptide linker (hingeless) or via an IgG hinge has been described in Olafsen, et al., *Protein Eng Des Sel.* 17(4):315-23, 2004.

Intrabodies are single chain antibodies which demonstrate intracellular expression and can manipulate intracellular protein function (Biocca, et al., *EMBO J.* 9:101-108, 1990; Colby et al., *PNAS.* 101:17616-21, 2004). Intrabodies, which comprise cell signal sequences which retain the antibody construct in intracellular regions, may be produced as described in Mhashilkar et al., (*EMBO J* 14:1542-51, 1995) and Wheeler et al., (*FASEB J.* 17:1733-5. 2003). Transbodies are cell-permeable antibodies in which a protein transduction domain (PTD) is fused with single chain variable fragment (scFv) antibodies (Heng et al., *Med Hypotheses.* 64:1105-8, 2005).

Further contemplated are antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO 03/041600, U.S. Patent Publication No. 20030133939 and US Patent Publication No. 20030118592.

One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

Thus, a variety of compositions comprising one, two, and/or three CDRs (e.g., a single CDR alone or in tandem, 2, 3, or other multiple repeats of the CDRs, or combinations of 2 or 3 CDRs alone or in tandem repeats; optionally, with a spacer amino acid sequence between the CDRs or repeats) of a heavy chain variable region or a light chain variable region of an antibody may be generated by techniques known in the art.

Chimeric and Humanized Antibodies

Because chimeric or humanized antibodies are less immunogenic in humans than the parental non-human (e.g., mouse) monoclonal antibodies, they can be used for the treatment of humans with far less risk of anaphylaxis Chimeric monoclonal antibodies, in which the variable Ig domains of a non-human (e.g., mouse) monoclonal antibody are fused to human constant Ig domains, can be generated using standard procedures known in the art (See Morrison et al., *PNAS* 81, 6841-6855 (1984); and, Boulianne et al., *Nature* 312, 643-646, (1984)).

Humanized antibodies may be achieved by a variety of methods including, for example: (1) grafting the non-human complementarity determining regions (CDRs) onto a human framework and constant region (a process referred to in the art as humanizing through "CDR grafting"), (2) transplanting the entire non-human variable domains, but "cloaking" them with a human-like surface by replacement of surface residues (a process referred to in the art as "veneering"), or, alternatively, (3) substituting human amino acids at positions determined to be unlikely to adversely affect either antigen binding or protein folding, but likely to reduce immunogenicity in a human environment (e.g., HUMAN ENGINEERING™). In the present disclosure, humanized antibodies will include "CDR-grafted," "humanized," "veneered" and "HUMAN ENGINEERED™" antibodies. These methods are disclosed in, e.g., Jones et al., *Nature* 321:522 525 (1986); Morrison et al., Proc. Natl. Acad. Sci., U.S.A., 81:6851-6855 (1984); Morrison and Oi, *Adv. Immunol.*, 44:65-92 (1988); Verhoeyer et al., *Science* 239:1534-1536 (1988); Padlan, *Molec. Immun.* 28:489-498 (1991); Padlan, *Molec. Immunol.* 31:169-217 (1994); Studnicka et al. U.S. Pat. No. 5,766,886; Studnicka et al., (*Protein Engineering* 7:805-814, 1994; Co et al., *J. Immunol.* 152, 2968-2976 (1994); Riechmann, et al., *Nature* 332:323-27 (1988); and Kettleborough et al., *Protein Eng.* 4:773-783 (1991) each of which is incorporated herein by reference. CDR grafting techniques are known in the field, see for example, Riechmann, et al. *Nature* 332:323-27 (1988). Additional antibody humanization methods are reviewed by Safdan et al., *Biotech. Gen. Eng. Rev.* 29: 175-86, 2013.

Human Antibodies from Transgenic Animals

Human antibodies to target protein can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/00906 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 and U.S. Pat. No. 6,091, 001 disclose the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. See also, U.S. Pat. Nos. 6,114,598, 6,657,103 and 6,833,268; Green L L, *Curr Drug Discovery*

Technol., 11(1), 74-84, 2014; Lee et al., *Nature Biotechnology*, 32:356-363, 2014; Lee and Owen, *Methods Mol Biol.*, 901:137-48, 2012).

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL-6, IL-8, TNFα, human CD4, L selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. Patent Publication No. 20030194404; and U.S. Patent Publication No. 20030031667.

Additional transgenic animals useful to make monoclonal antibodies include the Medarex HuMAb-MOUSE®, described in U.S. Pat. No. 5,770,429 and Fishwild, et al. (*Nat. Biotechnol.* 14:845-851 (1996)), which contains gene sequences from unrearranged human antibody genes that code for the heavy and light chains of human antibodies. Immunization of a HuMAb-MOUSE® enables the production of fully human monoclonal antibodies to the target protein.

Also, Ishida et al. (*Cloning Stem Cells.* 4:91-102 (2002)) describes the TransChromo Mouse (TCMOUSE™) which comprises megabase-sized segments of human DNA and which incorporates the entire human immunoglobulin (hIg) loci. The TCMOUSE™ has a fully diverse repertoire of hIgs, including all the subclasses of IgGs (IgG1-G4). Immunization of the TCMOUSE™ with various human antigens produces antibody responses comprising human antibodies.

See also Jakobovits et al., *PNAS*, 90:2551 (1993); Jakobovits et al., *Nature,* 362:255-258 (1993); Bruggermann et al., *Year in Immunol.,* 7:33 (1993); and U.S. Pat. Nos. 5,591,669, 5,589,369, 5,545,807; and U.S Patent Publication No. 20020199213. U.S. Patent Publication No. 20030092125 describes methods for biasing the immune response of an animal to the desired epitope. Human antibodies may also be generated by in vitro activated B cells (see U.S. Pat. Nos. 5,567,610 and 5,229,275).

Human Antibodies from Display Technology

The development of technologies for making repertoires of recombinant human antibody genes, and the display of the encoded antibody fragments on the surface of filamentous bacteriophage, has provided a means for making human antibodies directly. Antibodies generated by phage technology are produced as antigen binding fragments-usually scFv or Fab fragments-in bacteria and thus lack effector functions. Effector functions can be introduced by one of two strategies: The fragments can be engineered, for example, into complete antibodies for expression in mammalian cells, or into bispecific antibody fragments with a second binding site capable of triggering an effector function.

By way of example, one method for preparing the library of antibodies for use in phage display techniques comprises the steps of immunizing a non-human animal comprising human immunoglobulin loci with target antigen or an antigenic portion thereof to create an immune response, extracting antibody producing cells from the immunized animal; isolating RNA from the extracted cells, reverse transcribing the RNA to produce cDNA, amplifying the cDNA using a primer, and inserting the cDNA into a phage display vector such that antibodies are expressed on the phage. Recombinant target-specific antibodies of the disclosure may be obtained in this way.

In another example, antibody producing cells can be extracted from non-immunized animals, RNA isolated from the extracted cells and reverse transcribed to produce cDNA, which is amplified using a primer, and inserted into a phage display vector such that antibodies are expressed on the phage. Phage-display processes mimic immune selection through the display of antibody repertoires on the surface of filamentous bacteriophage, and subsequent selection of phage by their binding to an antigen of choice. One such technique is described in WO 99/10494, which describes the isolation of high affinity and functional agonistic antibodies for MPL and msk receptors using such an approach. Antibodies of the disclosure can be isolated by screening of a recombinant combinatorial antibody library, for example a scFv or Fab phage display library, prepared using human VL and VH cDNAs prepared from mRNA derived from human lymphocytes. Methodologies for preparing and screening such libraries are known in the art. See e.g., U.S. Pat. No. 5,969,108. There are commercially available kits for generating phage display libraries (e.g., The Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum. Antibod. Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J. Mol. Biol.* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al., (1991) *Nuc Acid Res* 19:4133-4137; and Barbas et al., (1991) *PNAS* 88:7978-7982, and Omidfar & Daneshpour, *Exp. Op. Drug Disc.* 10:651-669, 2015.

In one embodiment, to isolate human antibodies specific for the target antigen with the desired characteristics, a human VH and VL library is screened to select for antibody fragments having the desired specificity. The antibody libraries used in this method may be scFv libraries prepared and screened as described herein and in the art (McCafferty et al., PCT Publication No. WO 92/01047, McCafferty et al., (*Nature* 348:552-554 (1990)); and Griffiths et al., (*EMBO J* 12:725-734 (1993)). The antibody libraries preferably are screened using target protein as the antigen.

Alternatively, the Fd fragment (VH-CH1) and light chain (VL-CL) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. Through several rounds of antigen binding and re-amplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., *Bio/Technology* 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., *J. Mol. Biol.,* 227:381 (1991); Marks et al., *J. Mol. Biol,* 222:581-597 (1991); U.S. Pat. Nos. 5,565,332 and 5,573,905; Clackson, T., and Wells, J. A., TIBTECH 12, 173-184 (1994)). In particular, in vitro selection and evolution of antibodies derived from phage display libraries has become a powerful tool (See Burton, D. R., and Barbas III, C. F., *Adv. Immunol.* 57, 191-280 (1994); Winter, G., et al., *Annu. Rev. Immunol.* 12, 433-455 (1994); U.S. Patent Publication No. 20020004215 and WO 92/01047; U.S. Patent Publication No. 20030190317; and U.S. Pat. Nos. 6,054,287 and 5,877,293).

Fv fragments are displayed on the surface of phage, by the association of one chain expressed as a phage protein fusion (e.g., with M13 gene III) with the complementary chain expressed as a soluble fragment. It is contemplated that the phage may be a filamentous phage such as one of the class I phages: fd, M13, f1, If1, lke, ZJ/Z, Ff and one of the class II phages Xf, Pf1 and Pf3. The phage may be M13, or fd or a derivative thereof.

Once initial human VL and VH segments are selected, "mix and match" experiments, in which different pairings of selected VL and VH segments are screened for target binding, to select preferred VL/VH pair combinations (See, for example, Kang et al., *PNAS* 88: 11120-11123, (1991)). Additionally, to further improve the quality of the antibody, the VL and VH segments of the preferred VL/VH pair(s) can be randomly mutated, preferably within the any of the CDR1, CDR2 or CDR3 region of VH and/or VL, in a process analogous to the in vivo somatic mutation process responsible for affinity maturation of antibodies during a natural immune response. This in vitro affinity maturation can be accomplished by amplifying VL and VH regions using PCR primers complementary to the VH CDR1, CDR2, and CDR3, or VL CDR1, CDR2, and CDR3, respectively, which primers have been "spiked" with a random mixture of the four nucleotide bases at certain positions such that the resultant PCR products encode VL and VH segments into which random mutations have been introduced into the VH and/or VL CDR3 regions. These randomly mutated VL and VH segments can be rescreened for binding to target antigen.

Following screening and isolation of a target specific antibody from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the disclosure, as described below. To express a recombinant human antibody isolated by screening of a combinatorial library, the DNA encoding the antibody is cloned into a recombinant expression vector and introduced into a mammalian host cell, as described herein.

It is contemplated that the phage display method may be carried out in a mutator strain of bacteria or host cell. A mutator strain is a host cell which has a genetic defect which causes DNA replicated within it to be mutated with respect to its parent DNA. Example mutator strains are NR9046mutD5 and NR9046 mut T1.

It is also contemplated that the phage display method may be carried out using a helper phage. This is a phage which is used to infect cells containing a defective phage genome and which functions to complement the defect. The defective phage genome can be a phagemid or a phage with some function encoding gene sequences removed. Examples of helper phages are M13K07, M13K07 gene III no. 3; and phage displaying or encoding a binding molecule fused to a capsid protein.

Antibodies are also generated via phage display screening methods using the hierarchical dual combinatorial approach as disclosed in WO 92/01047 in which an individual colony containing either an H or L chain clone is used to infect a complete library of clones encoding the other chain (L or H) and the resulting two-chain specific binding member is selected in accordance with phage display techniques such as those described therein. This technique is also disclosed in Marks et al., (*Bio/Technology*, 10:779-783 (1992)).

Methods for display of peptides on the surface of yeast, microbial and mammalian cells have also been used to identify antigen specific antibodies. See, for example, U.S. Pat. Nos. 5,348,867; 5,723,287; 6,699,658; Wittrup, *Curr Op. Biotech.* 12:395-99 (2001); Lee et al., *Trends in Biotech.* 21(1) 45-52 (2003); Surgeeva et al., *Adv. Drug Deliv. Rev.* 58: 1622-54 (2006). Antibody libraries may be attached to yeast proteins, such as agglutinin, effectively mimicking the cell surface display of antibodies by B cells in the immune system.

In addition to phage display methods, antibodies may be isolated using in vitro display methods and microbial cell display, including ribosome display and mRNA display (Amstutz et al., *Curr. Op. Biotech.* 12:400-05 (2001)). Selection of polypeptides using ribosome display is described in Hanes et al., (*PNAS,* 94:4937-4942 (1997)) and U.S. Pat. Nos. 5,643,768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

Amino Acid Sequence Variants

Modified polypeptide compositions comprising one, two, three, four, five, and/or six CDRs of an antibody may be generated, wherein a CDR is altered to provide increased specificity or affinity to the target molecule. Sites within antibody CDRs are typically modified in series, e.g., by substituting first with conservative choices (e.g., hydrophobic amino acid substituted for a non-identical hydrophobic amino acid) and then with more dissimilar choices (e.g., hydrophobic amino acid substituted for a charged amino acid), and then deletions or insertions may be made at the target site. For example, using the conserved framework sequences surrounding the CDRs, PCR primers complementary to these consensus sequences are generated to amplify the antigen-specific CDR sequence located between the primer regions. Techniques for cloning and expressing nucleotide and polypeptide sequences are well-established in the art [see e.g. Sambrook et al., Molecular Cloning: A Laboratory Manual, 2nd Edition, Cold Spring Harbor, N.Y. (1989)]. The amplified CDR sequences are ligated into an appropriate plasmid. The plasmid comprising one, two, three, four, five and/or six cloned CDRs optionally contains additional polypeptide encoding regions linked to the CDR.

Modifications may be made by conservative or non-conservative amino acid substitutions described in greater detail below. "Insertions" or "deletions" are preferably in the range of about 1 to 20 amino acids, more preferably 1 to 10 amino acids. The variation may be introduced by systematically making substitutions of amino acids in an antibody polypeptide molecule using recombinant DNA techniques and assaying the resulting recombinant variants for activity. Nucleic acid alterations can be made at sites that differ in the nucleic acids from different species (variable positions) or in highly conserved regions (constant regions). Methods for altering antibody sequences and expressing antibody polypeptide compositions useful in the disclosure are described in the art. See e.g., U.S. Pat. No. 8,569,462. Another type of variant is an amino acid substitution variant. These variants have at least one amino acid residue in the antibody molecule removed and a different residue inserted in its place. Substitutional mutagenesis within any of the hypervariable or CDR regions or framework regions is contemplated. Conservative substitutions involve replacing an amino acid with another member of its class. Non-conservative substitutions involve replacing a member of one of these classes with a member of another class.

Conservative amino acid substitutions are made on the basis of similarity in polarity, charge, solubility, hydrophobicity, hydrophilicity, and/or the amphipathic nature of the residues involved. For example, nonpolar (hydrophobic) amino acids include alanine (Ala, A), leucine (Leu, L), isoleucine (Ile, I), valine (Val, V), proline (Pro, P), phenylalanine (Phe, F), tryptophan (Trp, W), and methionine (Met, M); polar neutral amino acids include glycine (Gly, G), serine (Ser, S), threonine (Thr, T), cysteine (Cys, C), tyrosine (Tyr, Y), asparagine (Asn, N), and glutamine (Gln, Q); positively charged (basic) amino acids include arginine (Arg, R), lysine (Lys, K), and histidine (His, H); and negatively charged (acidic) amino acids include aspartic acid (Asp, D) and glutamic acid (Glu, E).

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Altered Glycosylation

Antibody variants can also be produced that have a modified glycosylation pattern relative to the parent antibody, for example, deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to an antibody by altering the amino acid sequence such that it contains one or more of these tripeptide sequences. O-linked glycosylation refers to the attachment of one of the sugars N-acelylgalactosamine, galactose, or xylose to a hydroxyamino acid, most commonly serine or threonine, although 5-hydroxyproline or 5-hydroxylysine may also be used. O-linked glycosylation sites may be added to an antibody by inserting or substituting one or more serine or threonine residues to the sequence of the original antibody.

Fc glycans influence the binding of IgG to Fc receptors and C1q, and are therefore important for IgG effector functions. Antibody variants with modified Fc glycans and altered effector function may be produced. For example, antibodies with modified terminal sugars such as sialic acids, core fucose, bisecting N-acetylglucosamine, and mannose residues may have altered binding to the FcγRIIIa receptor and altered ADCC activity. In a further example, antibodies with modified terminal galactose residues may have altered binding to C1q and altered CDC activity (Raju, Curr. Opin. Immunol. 20:471-78, 2008).

Also contemplated for use in the methods are antibody molecules with absent or reduced fucosylation that exhibit improved ADCC activity. A variety of ways are known in the art to accomplish this. See for example, Yamane-Ohnuki et al., Biotechnol Bioeng. 87:614-22 (2004); Rothman et al., Mol Immunol. 26:1113-23 (1989); Shields et al., J Biol Chem. 277:26733-40 (2002); Shinkawa et al., J Biol Chem. 278:3466-73 (2003); Umana et al., Nat Biotechnol. 17:176-80 (1999); Ferrara et al., Biotechnol Bioeng. 93:851-61 (2006)). Glycosylation of antibodies and methods are reviewed in Niewa and Satoh, J. Pharmaceutical Sciences 104:930-41, (2015).

Variants with Altered Effector Function

Other modifications of the antibodies for use in the methods are contemplated. In one aspect, it may be desirable to modify an antibody used herein with respect to effector function, for example, to enhance the effectiveness of the antibody in treating cancer. One method for modifying effector function teaches that cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., (J. Exp Med. 176:1191-1195 (1992)) and Shopes, B (J. Immunol. 148:2918-2922 (1992)). Homodimeric antibodies with enhanced anti-tumor activity may also be prepared using heterobifunctional cross-linkers as described in Wolff et al., (Cancer Research 53:2560-2565 (1993)). Alternatively, an antibody can be engineered which has dual Fc regions and may thereby have enhanced complement lysis and ADCC capabilities. See Stevenson et al., (Anti-Cancer Drug Design 3:219-230 (1989)).

In certain embodiments of the present disclosure, it may be desirable to use an antibody fragment, rather than an intact antibody, to increase therapeutic efficacy, for example. In this case, it may be desirable to modify the antibody fragment in order to increase its serum half-life, for example, adding molecules such as PEG or other water soluble polymers, including polysaccharide polymers, to antibody fragments to increase the half-life.

As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. The salvage receptor binding epitope preferably constitutes a region wherein any one or more amino acid residues from one or two loops of an Fc domain are transferred to an analogous position of the antibody fragment. In one embodiment, three or more residues from one or two loops of the Fc domain are transferred. In another embodiment, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the CL region or VL region, or both, of the antibody fragment.

Antibodies of the present disclosure may comprise a human Fc portion, a human consensus Fc portion, or a variant thereof that retains the ability to interact with the Fc salvage receptor [see, e.g., Sarmay et al., *Molec. Immunol.* 29:633-9 (1992)].

Shields et al. reported that IgG1 residues involved in binding to all human Fc receptors are located in the CH2 domain proximal to the hinge and fall into two categories as follows: 1) positions that may interact directly with all FcR include Leu234-Pro238, Ala327, and Pro329 (and possibly Asp265); 2) positions that influence carbohydrate nature or position include Asp265 and Asn297. The additional IgG1 residues that affected binding to Fc receptor II are as follows: (largest effect) Arg255, Thr256, Glu258, Ser267, Asp270, Glu272, Asp280, Arg292, Ser298, and (less effect) His268, Asn276, His285, Asn286, Lys290, Gln295, Arg301, Thr307, Leu309, Asn315, Lys322, Lys326, Pro331, Ser337, Ala339, Ala378, and Lys414. A327Q, A327S, P329A, D265A and D270A reduced binding. Additional IgG1 residues that reduced binding to Fc receptor IIIA are known in the art. See also Presta et al., (*Biochem. Soc. Trans.* 30:487-490, 2001) and U.S. Pat. Nos. 6,194,551, 6,737,056 5,624,821, and U.S. Patent Publication No. 20040132101, which are incorporated herein by reference in its entirety.

Covalent Modifications

Antibodies comprising covalent modifications are also contemplated for use in the methods. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Other modifications include histidlyl, lysinyl arginyl, tyrosyl, glutaminyl and asparaginyl hydroxylation of proline and lysine. Methods for making such modifications are disclosed in U.S. Pat. No. 8,926,976, incorporated herein by reference, and in the art.

Carboxyl side groups (aspartyl or glutamyl) are selectively modified by reaction with carbodiimides (R-N.dbd.C.dbd.N-R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 and in Aplin and Wriston, (CRC *Crit. Rev. Biochem.*, pp. 259-306 (1981)).

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin, et al., (Arch. Biochem. Biophys. 259: 52 (1987)) and by Edge et al., (Anal. Biochem. 118: 131 (1981)). Enzymatic cleavage of carbohydrate moieties on antibodies can be achieved by the use of a variety of endo- and exo-glycosidases as described by Thotakura et al., (*Meth. Enzymol.* 138: 350 (1987)).

Another type of covalent modification of the antibody comprises linking the antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art.

Derivatives

As stated above, derivative, when used in connection with antibody substances and polypeptides, refers to polypeptides chemically modified by such techniques as ubiquitination, conjugation to therapeutic or diagnostic agents, labeling (e.g., with radionuclides or various enzymes), covalent polymer attachment such as PEGylation (derivatization with polyethylene glycol) and insertion or substitution by chemical synthesis of amino acids such as ornithine. Derivatives of the antibodies disclosed herein are also useful as therapeutic agents and may be used in the methods herein.

The conjugated moiety can be incorporated in or attached to an antibody substance either covalently, or through ionic, van der Waals or hydrogen bonds, e.g., incorporation of radioactive nucleotides, or biotinylated nucleotides that are recognized by streptavadin.

The antibody may be covalently attached to IL-2, or variants thereof, by a flexible linker e.g. $(Gly_4Ser)_3$. See for example, Tomala et al., *ACS Chemical Biology* 8, 871-876 (2013).

Polyethylene glycol (PEG) may be attached to the antibody substances to provide a longer half-life in vivo. The PEG group may be of any convenient molecular weight and may be linear or branched. The average molecular weight of the PEG will preferably range from about 2 kiloDalton ("kDa") to about 100 kDa, more preferably from about 5 kDa to about 50 kDa, most preferably from about 5 kDa to about 10 kDa. The PEG groups will generally be attached to the antibody substances of the disclosure via acylation or reductive alkylation through a natural or engineered reactive group on the PEG moiety (e.g., an aldehyde, amino, thiol, or ester group) to a reactive group on the antibody substance (e.g., an aldehyde, amino, or ester group). Addition of PEG moieties to antibody substances can be carried out using techniques well-known in the art. See, e.g., International Publication No. WO 96/11953 and U.S. Pat. No. 4,179,337.

Ligation of the antibody substance with PEG usually takes place in aqueous phase and can be easily monitored by reverse phase analytical HPLC. The PEGylated substances are purified by preparative HPLC and characterized by analytical HPLC, amino acid analysis and laser desorption mass spectrometry.

Antibody Conjugates

An antibody may be administered in its "naked" or unconjugated form, or may be conjugated directly to other therapeutic or diagnostic agents, or may be conjugated indirectly to carrier polymers comprising such other therapeutic or diagnostic agents.

Antibodies can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are well known in the art; for example, see (Sternberger, L. A. et al., *J. Histochem. Cytochem.* 18:315 (1970); Bayer, E. A. et al., *Meth. Enzym.* 62:308 (1979); Engval, E. et al., *Immunol.* 109:129 (1972); Goding, J. W. *J. Immunol. Meth.* 13:215 (1976)).

Conjugation of antibody moieties is described in U.S. Pat. No. 6,306,393. General techniques are also described in Shih et al., *Int. J. Cancer* 41:832-839 (1988); Shih et al., *Int. J. Cancer* 46:1101-1106 (1990); and Shih et al., U.S. Pat. No. 5,057,313. This general method involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer may be, for example, an aminodextran or polypeptide of at least 50 amino acid residues. Various techniques for conjugating a drug or other agent to the carrier polymer are known in the art. A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and conjugate. Examples of agents to which the antibody can be conjugated include any of the cytotoxic or chemotherapeutic agents described herein.

Alternatively, conjugated antibodies can be prepared by directly conjugating an antibody component with a therapeutic agent. The general procedure is analogous to the indirect method of conjugation except that a therapeutic agent is directly attached to an oxidized antibody component. For example, a carbohydrate moiety of an antibody can be attached to polyethyleneglycol to extend half-life.

Alternatively, a therapeutic agent can be attached at the hinge region of a reduced antibody component via disulfide bond formation, or using a heterobifunctional cross-linker, such as N-succinyl 3-(2-pyridyldithio)proprionate (SPDP). Yu et al., *Int. J. Cancer* 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering and Clinical Application, Ritter et al. (eds.), pages 60-84 (Cambridge University Press 1995). A variety of bifunctional protein coupling agents are known in the art, such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Recombinant Production of Antibodies

DNA encoding an antibody described herein may be isolated and sequenced using conventional procedures (e.g., by using oligonucleotide probes that are capable of binding specifically to genes encoding the heavy and light chains of the antibodies). Usually this requires cloning the DNA or, preferably, mRNA (i.e., cDNA) encoding the antibodies. Cloning and sequencing is carried out using standard techniques, such as for example polymerase chain reaction (PCR), (see e.g., Sambrook et al. (1989) Molecular Cloning: A Laboratory Guide, Vols 1-3, Cold Spring Harbor Press; Ausubel, et al. (Eds.), Protocols in Molecular Biology, John Wiley & Sons (1994)), which are incorporated herein by reference).

Sequencing is carried out using standard techniques (see e.g., Sambrook et al. (1989) Molecular Cloning: A Laboratory Guide, Vols 1-3, Cold Spring Harbor Press, and Sanger, F. et al. (1977) *PNAS* 74:5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Once isolated, the DNA may be placed into expression vectors, which are then transfected into host cells such as *E. coli* cells, simian COS cells, human embryonic kidney 293 cells (e.g., 293E cells), Chinese hamster ovary (CHO) cells, or myeloma cells that do not otherwise produce immunoglobulin protein, to obtain the synthesis of monoclonal antibodies in the recombinant host cells. Recombinant production of antibodies is well known in the art.

For recombinant production of the antibodies, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more selective marker genes, an enhancer element, a promoter, and a transcription termination sequence, which are known and described in the art.

In various embodiments, the nucleotide sequences set out in SEQ ID NOs: 2, 4, 6, 8, 10, 12, 14, or 16 are useful for expressing the antibodies herein or fragments thereof.

In some embodiments, different nucleic acid molecules encode a heavy chain variable region and a light chain variable region of a target specific antibody. In other embodiments, the same nucleic acid molecule encodes a heavy chain and a light chain variable regions of a target specific antibody. In one embodiment, the nucleic acid encodes a target specific antibody of the present disclosure, as well as any of the polypeptides encoded by the nucleic acids described herein.

In one aspect, a nucleic acid molecule of the present disclosure comprises a nucleotide sequence that encodes the VL amino acid sequence of antibodies XPA.92.019, XPA.92.041, XPA.92.042 and XPA.92.099 set out in SEQ ID NOs: 9, 11, 13, or 15, or a portion thereof. In a related aspect, the VL amino acid sequence is a consensus sequence. In some embodiments, the nucleic acid encodes the amino acid sequence of the light chain CDRs of said antibody. In some embodiments, said portion is a contiguous portion comprising CDR1-CDR3. In one embodiment, said portion comprises at least one, two or three of a light chain CDR1, CDR2, or CDR3 region, optionally with a different human or human consensus framework, and optionally with 1, or up to 2, or up to 3 mutations in the collective 3 CDRs.

In one embodiment the present disclosure provides antigen-binding compounds, including functional fragments, having a variable region amino acid sequence set forth in any one of SEQ ID NOs: 1, 3, 5, 7, 9, 11, 13, or 15. In a related embodiment, an aforementioned antigen binding compound is selected from the group consisting of a fully assembled tetrameric antibody, a monoclonal antibody a humanized antibody; a human antibody; a chimeric antibody; a multispecific antibody, an antibody fragment, Fab, F(ab')2; Fv; scFv or single-chain antibody fragment; a diabody; triabody, tetrabody, minibody, linear antibody; chelating recombinant antibody, a tribody or bibody, an intrabody, a nanobody, a small modular immunopharmaceutical (SMIP), a binding-domain immunoglobulin fusion protein, a camelized antibody, a VHH containing antibody, or a variant or derivative of any one of these antibodies, that comprise one or more CDR sequences of the disclosure and exhibit the desired biological activity, or a mixture of two or more antibodies. The antigen binding compounds of the present disclosure preferably retain binding affinity of $10^{-10}$, $10^{-11}$, $10^{-12}$, $10^{-13}$ M or less for IL-2, as measured by surface plasmon resonance.

In one aspect, the antibodies of the present disclosure comprise a heavy chain variable region or light chain variable region as set out in amino acid sequences SEQ ID NOs: 1, 3, 5, or 7 and SEQ ID NOs: 9, 11, 13, or 15, respectively, as paired in FIG. 12. It is further contemplated that the antibodies may comprise all or part of the antibodies set out in the above amino acid sequences. In one embodiment, the antibodies comprise at least one of CDR1, CDR2, or CDR3 of the heavy chain of SEQ ID NOs: 17, 18, 20-28 and 41, or at least one of CDR1, CDR2 or CDR3 of the light chain of SEQ ID NOs: 29-40, as paired in FIG. 12.

In one embodiment, the heavy chain comprises an amino acid sequence identified as a heavy chain CDR3 sequence. Such a "heavy chain CDR3 sequence" (HCDR3) includes an amino acid sequence identified as a heavy chain CDR3 sequence set out in FIG. 12 and SEQ ID NOs: 41, 22, 25, or 28. Alternatively, the HCDR3 sequence comprises an amino acid sequence that contains one or more amino acid changes (e.g., substitution, insertion or deletion) compared to any HCDR3 amino acid sequence identified in FIG. 12. Preferable substitutions include a substitution to an amino acid at the corresponding position within another HCDR3 of FIG. 12. Alternatively, the HCDR3 sequence may comprise a consensus amino acid sequence of the HCDR3 as determined from the sequences set out herein.

The heavy chain comprising a HCDR3 sequence described above may further comprise a "heavy chain CDR1 sequence" (HCDR1), which includes any of the amino acid sequences identified as an HCDR1 in SEQ ID NOs: 17, 20, 23, or 26, or FIGS. 12A-12E, amino acid sequences that contain one or more amino acid changes compared to any HCDR1 identified in SEQ ID NOs: 17, 20, 23, or 26, or FIGS. 12A-12E, preferably a substitution to an amino acid at the corresponding position within another HCDR1 of FIGS. 12A-12E, or a consensus sequence of the HCDR1 described herein.

Alternatively, the heavy chain comprising a HCDR3 sequence described above may further comprise a "heavy chain CDR2 sequence" (HCDR2), which includes any of the amino acid sequences identified as an HCDR2 in SEQ ID NOs: 18, 21, 24, or 27, or FIGS. 12A-12E, amino acid sequences that contain one or more amino acid changes compared to any HCDR2 identified in SEQ ID NOs: 18, 21, 24, or 27, or FIGS. 12A-12E, preferably a substitution to an amino acid at the corresponding position within another HCDR2 of FIGS. 12A-12E, or a consensus sequence of the HCDR2 described herein.

The heavy chain comprising a heavy chain CDR3 sequence described above may also comprise both (a) a heavy chain CDR1 sequence described above and (b) a heavy chain CDR2 sequence of the invention described above.

One aspect of the present disclosure provides an antibody that binds target antigen comprising a heavy chain that comprises any one, two, and/or three of the heavy chain CDR sequences described below.

Any of the heavy chain CDR sequences described above may also include amino acids added to either end of the CDRs. Preparation of variants and derivatives of antibodies and antigen-binding compounds of the present invention, including affinity maturation or preparation of variants or derivatives containing amino acid analogs, is described in further detail herein. Exemplary variants include those containing a conservative or non-conservative substitution of a corresponding amino acid within the amino acid sequence, or a replacement of an amino acid with a corresponding amino acid of a different human antibody sequence.

Antibodies comprising any one of the heavy chains described above may further comprise a light chain, preferably a light chain that binds to target antigen, and most preferably a light chain comprising light chain CDR sequences described below.

Another aspect of the present disclosure provides an antibody that binds target antigen comprising a light chain that comprises any one, two, and/or three of the light chain CDR sequences described below.

Preferably the light chain comprises an amino acid sequence identified as a light chain CDR3 sequence. Such a "light chain CDR3 sequence" (LCDR3) includes an amino acid sequence identified as a light chain CDR3 sequence in FIGS. 12A-12E and within SEQ ID NOs: 31, 34, 37, or 40. Alternatively, the light chain CDR3 sequence comprises an amino acid sequence that contains one or more amino acid changes (e.g., a substitution, insertion or deletion) compared to any light chain CDR3 amino acid sequence identified in FIGS. 12A-12E. Preferable substitutions include a substitution to an amino acid at the corresponding position within another light chain CDR3 of FIGS. 12A-12E.

The light chain comprising a light chain CDR3 sequence described above may further comprise a "light chain CDR1 sequence", which includes any of the amino acid sequences identified as a light chain CDR1 in SEQ ID NOs: 29, 32, 35, or 38, or FIGS. 12A-12E, amino acid sequences that contain one or more amino acid changes compared to any light chain CDR1 identified in SEQ ID NOs: 29, 32, 35, or 38, or FIGS. 12A-12E, preferably a substitution to an amino acid at the corresponding position within another light chain CDR1 of FIGS. 12A-12E.

Alternatively, the light chain comprising a light chain CDR3 sequence described above may further comprise a "light chain CDR2 sequence", which includes any of the amino acid sequences identified as a light chain CDR2 in SEQ ID NOs: 30, 33, 36, or 39, or FIGS. 12A-12E, amino acid sequences that contain one or more amino acid changes compared to any light chain CDR2 identified in FIGS. 12A-12E, preferably a substitution to an amino acid at the corresponding position within another light chain CDR2 of SEQ ID NOs: 30, 33, 36, or 39, or FIGS. 12A-12E.

In a related aspect, the present disclosure contemplates a purified polypeptide comprising at least one HCDR of SEQ ID NOs: 17, 18, 20-28 and 4147-28, or LCDR of SEQ ID NOs: 29-40, wherein the framework regions of the heavy chain variable region and the framework regions of the light chain variable region comprise framework regions from a human antibody. In another embodiment, the framework regions of the heavy chain variable region and the framework regions of the light chain variable region are chemically altered by amino acid substitution to be more homologous to a different human antibody sequence. For example, within each heavy chain framework region (H-FR1-4) it is contemplated that at least one, at least two, at least three, at least four, at least five, or at least six native framework region residues of the heavy chain variable region have been altered by amino acid substitution, and wherein within each light chain framework region (L-FR1-4), at least one, at least two, at least three, at least four, at least five or at least six native framework residues of the light chain variable region have been altered by amino acid substitution.

The light chain comprising a light chain CDR3 sequence described above may also comprise both (a) a light chain CDR1 sequence described above and (b) a light chain CDR2 sequence described above.

Antibodies comprising any one of the light chain variable regions described above may further comprise a heavy chain variable region, optionally paired as described in FIGS. 12A-12E, preferably a heavy chain variable region that binds to target antigen, and most preferably a heavy chain variable region comprising heavy chain CDR sequences described above.

In yet another embodiment, the antibody comprises a heavy chain variable region selected from the group consisting of SEQ ID NOs: 1, 3, 5, and 7, and a light chain variable region selected from the group consisting of SEQ ID NOs: 9, 11, 13, and 15.

In a related aspect, the nucleic acid molecule comprises a nucleotide sequence that encodes the light chain amino acid sequence of any one of SEQ ID NOs: 9, 11, 13 or 15 or a portion thereof. In one embodiment, the nucleic acid molecule comprises the light chain nucleotide sequence of any one of SEQ ID NOs: 10, 12, 14 or 16, or a portion thereof. Nucleic acid molecules of the disclosure further include all nucleic acid sequences, including the sequences in SEQ ID NOs: 2, 4, 6, 8, 10, 12, 14 or 16, and nucleic acid sequences comprises degenerate codons based on the diversity of the genetic code, encoding an amino acid sequence of the heavy and light chain variable regions of an antibody described herein or any HCDRs or LCDRs described herein, and as set out in SEQ ID NOs: 17, 18, 20-28 and 41 and 29-40, as well as nucleic acids that hybridize under highly stringent conditions, such as those described herein, to a nucleic acid sequence encoding an amino acid sequence of the heavy and light chain variable regions of an antibody described herein or any HCDRs or LCDRs described herein, and as set out in SEQ ID NOs: 17, 18, 20-28 and 41 and 29-40.

In some embodiments, the nucleic acid molecule encodes a VL amino acid sequence that is at least 60, 65, 70, 75, 80, 85, 90, 91, 92, 93, 94, 95, 96 97, 98 or 99% identical to a VL amino acid sequence set out in SEQ ID NOs: 9, 11, 13 or 15. Nucleic acid molecules of the disclosure include nucleic acids that hybridize under highly stringent conditions, such as those described herein, to a nucleic acid sequence encoding the light chain variable region amino acid sequence of SEQ ID NOs: 9, 11, 13 or 15, or that has the light chain variable region nucleic acid sequence of SEQ ID NOs: 10, 12, 14 or 16.

It is further contemplated that a nucleic acid molecule of the disclosure comprises a nucleotide sequence that encodes the VH amino acid sequence of any one of antibodies XPA.92.019, XPA.92.041, XPA.92.042 and XPA.92.099, or a portion thereof. In some embodiments, the nucleic acid encodes the amino acid sequence of the heavy chain CDRs of said antibody. In some embodiments, said portion is a contiguous portion comprising heavy chain CDR1-CDR3. In one embodiment, said portion comprises at least one, two or three of a heavy chain CDR1, CDR2, or CDR3 region, optionally with a different human or human consensus framework, and optionally with 1, or up to 2, or up to 3 mutations in the collective 3 CDRs.

In a related aspect, the nucleic acid molecule comprises a nucleotide sequence that encodes the heavy chain amino acid sequence of one of heavy chain of SEQ ID NOs: 1, 3, 5 or 7, or a portion thereof. In one embodiment, the nucleic acid molecule comprises the heavy chain nucleotide sequence of SEQ ID NOs: 2, 4, 6 or 8, or a portion thereof.

In some embodiments, the nucleic acid molecule encodes a VH amino acid sequence that is at least 70%, 75%, 80%, 85%, 90%, 95%, 96%, 97%, 98% or 99% identical to a VH amino acid sequence set out in SEQ ID NOs: 1, 3, 5, or 7. In a related aspect, the VH amino acid sequence is a consensus sequence. Nucleic acid molecules of the disclosure further include nucleic acids that hybridize under highly stringent conditions, such as those described herein, to a nucleic acid sequence encoding the heavy chain variable region amino acid sequence of SEQ ID NOs: 1, 3, 5, or 7, or that has the heavy chain variable region nucleic acid sequence of any one of SEQ ID NOs: 2, 4, 6 or 8.

It is further contemplated that the nucleic acids of the disclosure may encode a full-length light chain or heavy chain of an antibody selected from XPA.92.019, XPA.92.041, XPA.92.042 and XPA.92.099 wherein a full-length light chain or full-length heavy chain comprises a light chain constant region or a heavy chain constant region, respectively, light chain constant regions optionally include unmodified or modified kappa or lambda regions, and heavy constant regions include unmodified or modified constant regions of any of the classes, such as IgG1, IgG2, IgG3, IgG4, IgM, IgA, IgD, or IgE.

In one aspect, the full length variable light chain antibody comprises the sequences set out in SEQ ID NOs: 9, 11, 13 or 15. It is further contemplated that the nucleotide encoding the full-length light chain encodes the sequences set out in SEQ ID NOs: 9, 11, 13 or 15 and comprises the nucleotides sequence set forth in SEQ ID NOs: 10, 12, 14 or 16.

In one aspect, the full length variable heavy chain antibody comprises the sequences in any one of SEQ ID NOs: 1, 3, 5 or 7. It is further contemplated that the nucleotide encoding the full-length heavy chain encodes the sequences heavy chain of SEQ ID NOs: 1, 3, 5 or 7, and comprises the nucleotides sequence set forth in any one of SEQ ID NOs: 2, 4, 6 or 8.

In further embodiments, the disclosure provides an antibody that binds IL-2 comprising a light chain variable region and/or a heavy chain variable region, wherein (a) the light chain variable region comprises at least a CDR1 selected from SEQ ID NOs: 29, 32, 35, or 38 or sequences at least 80% identical thereto, a CDR2 selected from SEQ ID NOs: 30, 33, 36, or 39 or sequences at least 80% identical thereto, and/or a CDR3 selected from SEQ ID NOs: 31, 34, 37, or 40 or sequences at least 80% identical thereto; and/or wherein (b) the heavy chain variable region comprises at least a CDR1 selected from SEQ ID NOs: 17, 20, 23, or 26, or sequences at least 80% identical thereto, a CDR2 selected from SEQ ID NOs: 18, 21, 24, or 27, or sequences at least 80% identical thereto, and/or a CDR3 selected from SEQ ID NOs: 41, 22, 25, or 28, or sequences at least 80% identical thereto.

In a related embodiment, the light chain variable region comprises at least a CDR1 selected from SEQ ID NO: 29, 32, 35, or 38 or sequences at least 90% identical thereto, a CDR2 selected from SEQ ID NO: 30, 33, 36, or 39 or sequences at least 90% identical thereto, and a CDR3 selected from SEQ ID NO: 31, 34, 37, or 40 or sequences at least 90% identical thereto; and/or the heavy chain variable region comprises at least a CDR1 selected from SEQ ID NO: 17, 20, 23, or 26, or sequences at least 90% identical thereto, a CDR2 selected from SEQ ID NO: 18, 21, 24, or 27, or sequences at least 90% identical thereto, and a CDR3 selected from SEQ ID NO: 41, 22, 25, or 28, or sequences at least 90% identical thereto.

In exemplary embodiments, an antibody of the disclosure comprises a human kappa (κ) or a human lambda (λ) light chain or an amino acid sequence derived therefrom, or a human heavy chain or a sequence derived therefrom, or both heavy and light chains together in a single chain, dimeric, tetrameric or other form.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), K. wickeramii (ATCC 24,178), *K. waltii* (ATCC 56,500), *K. drosophilarum* (ATCC 36,906), *K. thermotolerans*, and *K. marxianus*; *yarrowia* (EP 402,226); *Pichia* pastors (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium,* and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells.

Plant cell cultures of cotton, corn, potato, soybean, petunia, tomato, tobacco, lemna, and other plant cells can also be utilized as hosts.

Examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., *PNAS* 77:4216 (1980)); monkey kidney CV1 line transformed by SV40 (COS-7, ATCC CRL 1651); human embryonic kidney line (293 or 293 cells subcloned for growth in suspension culture, (Graham et al., J. Gen Virol. 36:59, 1977); baby hamster kidney cells (BHK, ATCC CCL 10); mouse sertoli cells (TM4, Mather, (Biol. Reprod. 23:243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y Acad. Sci. 383:44-68 (1982)); MRC 5 cells; FS4 cells; and a human hepatoma line (Hep G2).

Host cells are transformed or transfected with the above-described expression or cloning vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies that bind target.

When using recombinant techniques, the antibody can be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration. Better et al. (*Science* 240:1041-43, 1988; ICSU Short Reports 10:105 (1990); and *PNAS* 90:457-461 (1993) describe a procedure for isolating antibodies which are secreted to the periplasmic space of *E. coli*. See also, (Carter et al., *Bio/Technology* 10:163-167 (1992).

Alternatively, the antibody can be synthesized in a cell-free system using prokaryotic or eukaryotic in vitro translation (see Stech and Kubick, *Antibodies* 4:12-33, 2015).

The antibody composition can be purified using, for example, hydroxylapatite chromatography cation or avian exchange chromatography, and affinity chromatography, with affinity chromatography being a well-known purification technique. The suitability of protein A as an affinity ligand depends on the species and isotype of any immunoglobulin Fc domain that is present in the antibody. Protein A can be used to purify antibodies that are based on human $\gamma 1$, $\gamma 2$, or $\gamma 4$ heavy chains (Lindmark et al., *J. Immunol. Meth.* 62:1-13, 1983). Protein G is recommended for all mouse isotypes and for human $\gamma 3$ (Guss et al., *EMBO J.* 5:15671575 (1986)). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the antibody comprises a CH 3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE® chromatography on an anion or cation exchange resin (such as a polyaspartic acid column), chromatofocusing, SDS-PAGE, and ammonium sulfate precipitation are also available depending on the antibody to be recovered.

In one embodiment, the IL-2 antibodies can be produced alone or co-expressed with IL-2 using methods as described for IL-15/IL-15R complexes in Bergmaschi et al., *JBC* 283(7), 4189-4199 (2007) and Gaston et al., *PLoS One.* 27; 8(11):e81768 (2013), which are incorporated by reference in their entirety. For example, IL-2 and IL-2 antibody could be coexpressed on plasmids in the same cell type, either on a single plasmid or multiple plasmids, and allowed to complex during the recombinant expression phase of production. Alternatively, IL-2 and IL-2 antibodies are expressed in different cells and then complexed together in a separate step.

Screening Methods

Effective therapeutics depend on identifying efficacious agents devoid of significant toxicity. Antibodies may be screened for binding affinity by methods known in the art. For example, gel-shift assays, Western blots, radiolabeled competition assay, co-fractionation by chromatography, co-precipitation, cross linking, ELISA, surface plasmon resonance, KinExA and the like may be used, which are described in, for example, Current Protocols in Molecular Biology (1999) John Wiley & Sons, NY, which is incorporated herein by reference in its entirety.

Methods for assessing the biological activity and modulation of IL-2 activity (e.g., by IL-2 antibodies) are known in the art. For example, neutralization can be measured by neutralization assays and expressed as an inhibitory concentration leading to 50% maximal (IC50) value. The IC50 value can be calculated for a given molecule by determining the concentration of molecule needed to elicit half inhibition of the maximum biological response of a second molecule or cell activity. The lower the IC50, the greater the potency of the molecule to inhibit the desired protein activity.

IL-2 Antibody Screening by Flow Cytometry

IL-2 antibody binding to human IL-2 receptors R$\alpha$ or R$\beta$ and $\gamma$c can be assessed by flow cytometry screening of cells naturally comprising or engineered to express human IL-2 receptors IL-2 R$\alpha$, IL-2 R$\beta$ or R$\beta$ and $\gamma$c using methods known in the art.

IL-2 Antibody Modulation of IL-2-Induced Proliferation

Evaluation of IL-2 antibody modulation of IL-2-induced proliferation of cells expressing different IL-2 receptor complexes (IL-2 R $\alpha\beta\gamma$ or IL-2 R$\beta\gamma$), including the effects on cell proliferation of antibodies which primarily block IL-2 R$\alpha$ interaction using a luminescent cell viability assay. For example, activity can be measured by proliferation assays and expressed as an EC50 (Effective Concentration leading to 50% maximal) value. The EC50 value can be calculated for a given molecule by determining the concentration of molecule needed to elicit half of the maximum biological response. The lower the EC50, the greater the potency of the molecule to elicit the desired activity.

IL-2-Induced STAT5 Phosphorylation

Modulation of IL-2 activity by IL-2 antibodies can be assessed by measurement of IL-2-induced activation of downstream transcription factor Signal Transducer and Activator of Transcription 5 (STAT5) in cells expressing different IL-2 receptor complexes (IL-2 R $\alpha\beta\gamma$ or IL-2 R$\beta\gamma$). Various doses of IL-2 and anti-IL-2 antibodies may be pre-complexed before adding to cells expressing different IL-2 receptor complexes. Phosphorylated (activated, pSTAT5) and total levels of STAT5 are measured by immunoassay, and the percent phosphorylated STAT5 is calculated. EC50 and IC50 values can be calculated as described above.

Other methods of assessing IL-2 activity known in the art can be used to analyze the biological effects of the antibodies herein. IL-2 can be administered to mice or other mammals, and its activity can be analyzed by measuring frequency or activity of immune cells such as effector, helper, or regulatory T cells, NK cells, or dendritic cells.

The activity of IL-2 can also be measured by monitoring upregulation of granzyme B or increased ability to secrete Interferon gamma in IL-2 responsive cells. IL-2 activity can also be measured by KI67 detection in IL-2 responsive cells. In mice, BRDU can be injected into the animals, and incorporation of BRDU in to IL-2 responsive cells are measured. In mice, the frequency of CD8+ or CD4+ T cells that become CD44hi or CD25hi is a measure of IL-2 activity. Methods for conducting these assays are known in the art.

Combination Therapy

An IL-2 antibody of the present disclosure may be administered with a second agent and the combination may be useful to treat a disease or disorder as described herein. In the case of the use of antibodies to IL-2, if more than one IL-2 antibody is effective at binding to respective target antigen, it is contemplated that two or more antibodies to different epitopes of the target antigen may be mixed such that the combination of antibodies provides still further improved efficacy against a condition or disorder to be treated. Compositions comprising one or more antibodies of the invention may be administered to persons or mammals suffering from, or predisposed to suffer from, a condition or disorder associated with IL-2 or the IL-2 R.

Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

Alternatively, the second agent may be other therapeutic agents, such as cytokines, growth factors, inhibitors and antibodies to other target antigens.

It is contemplated the therapeutic agents of the present disclosure may be given simultaneously, in the same formulation. It is further contemplated that the agents are administered in a separate formulation and administered concurrently, with concurrently referring to agents given within 30 minutes of each other. It is further contemplated that a second agent may be given simultaneously.

In another aspect, an antibody to IL-2 is administered prior to administration of the other composition. Prior administration refers to administration of an antibody within the range of one week prior to treatment with the other agent, up to 30 minutes before administration of the other agent. It is further contemplated that an agent is administered subsequent to administration of another composition or agent. Subsequent administration is meant to describe administration from 30 minutes after antibody treatment up to one week after antibody administration, e.g., 30 minutes, 1 hour 2 hours, 4 hours, 1 day, 2 days, etc. It is further contemplated that a second agent maybe administered in this manner prior, or subsequent to, administration of the IL-2 antibody.

It is further contemplated that other adjunct therapies may be administered, where appropriate. For example, the patient may also be administered surgical therapy, chemotherapy, a cytotoxic agent, photodynamic therapy, immune-modulating or radiation therapy where appropriate.

It is further contemplated that when the antibodies herein are administered in combination with a second agent, such as for example, wherein the second agent is a cytokine or growth factor, or a chemotherapeutic agent, the administration also includes use of a radiotherapeutic agent or radiation therapy. The radiation therapy administered in combination with an antibody composition is administered as determined by the treating physician, and at doses typically given to patients being treated for cancer.

A cytotoxic agent refers to a substance that inhibits or prevents the function of cells and/or causes destruction of cells. The term is intended to include radioactive isotopes (e.g., I131, I125, Y90 and Re186), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see e.g., U.S. Patent Publications 2003/0028071 and 2003/0032995 which are incorporated by reference herein). Such agents may be conjugated, coupled, linked or associated with an antibody according to the disclosure.

In one embodiment the second agent is a checkpoint inhibitor (e.g., an anti-PDL-1 antibody, an anti-CTLA-4 antibody, a PD-1 inhibitor, or a PDL-1 inhibitor PD-1). In other embodiments the IL-2 antibodies of the present invention may be combined with chimeric antigen receptor T-cells/tumor-infiltrating lymphocytes (CART/TIL) therapy or agent. In other embodiments the IL-2 antibodies of the present invention may be combined with vaccine therapy. In still another embodiment, the IL-2 antibodies of the present disclosure may be combined with other antibodies or agents targeting tumor-specific antigens.

Chimeric antigen receptors (CARs) are produced by expansion of CD4+ or CD8+ T cells transduced with a receptor complex consisting of a (scFv) extracellular domain of a tumor specific antibody, linked through hinge and transmembrane domains of either CD4+ or CD8+ to a cytoplasmic signaling region (Haji-Fatahaliha et al., *Artificial Cells, Nanomedicine, and Biotechnology* 44:1339-1349 (2016). Some CARs have been engineered to express costimulatory signaling domains (e.g, CD28, OX40, or 41BB), which can confer greater cytotoxic activity to these cells.

Tumor infiltrating lymphocytes (TILs) are typically CD4+ or CD8+ T cells isolated from fresh tumor samples or from the blood, expanded with IL-2 and then infused intravenously back into patients that provided the sample. Optionally, expansion of tumor antigen specific CD4+ or CD8+ T cells is carried out using APCs loaded with one or more tumor antigens. After cell infusion, patients are often given IL-2 (either a high or low dose) to maintain the activity of the TILs (Nayar et al., *OncoImmunology* 4(4), e1002720 (2015)). In another method, T cells are transduced with receptors specific for selected tumor antigens. This method involves taking peripheral blood mononuclear cells (PBMCs) and then transducing the T cells with TCRs specific for selected tumor antigens and expanding these cells.

In some embodiments, the IL-2 antibodies are administered in combination with IL-2 or IL-2 variants. In various embodiments, the antibodies can be complexed with IL-2 prior to administration or the IL-2 and IL-2 antibodies can be administered in combination as described herein (Garcia-Martinez and Leon, *Intl. Immunol.* 24: 427-446 (2012); Spangler et al., *Immunity*, 42: 815-825; Arenas-Ramirez et al., *Trends in Imunol.* 36: 763-777). It is contemplated that when the antibodies are administered in combination with IL-2, the amount of IL-2 is less than the therapeutic dose used, e.g., lower than 700,000 international units (I.U)/kg (0.04 mg/kg). In some embodiments, the IL-2 is administered at a dose of about 300,000 to 6000,000 I.U/kg, about 250,000 to 500,000 I.U./kg, about 100,000 to 250,000 I.U./kg, about 10,000 to 100,000 I.U./kg, or about 1,000 to 10,000 I.U./kg. or about 500 to 5,000 I.U./kg In various embodiments, the ratio of IL-2 to IL-2 antibody in the complex is 1:1, based on a molar ratio. In various embodiments, the ratio of IL-2 to IL-2 antibody in the complex is not 1:1, e.g., the ratio is about 5:1, 4:1, 3:1, 2:1, 1:2, 1:3, 1:4, 1:5, 1:6, 1:7, 1:8, 1:9, 1:10 or greater, based on molar ratio. In various embodiments, the IL-2-specific antibody is XPA.92.019 described herein.

In various embodiments, when the IL-2 and IL-2 antibody are pre-mixed prior to administration, the agents could be administered together twice weekly. In various embodiments, the IL-2 is administered at a dose of 0.1 to 10 mg/kg with a dose of antibody as described herein. In various embodiments, the IL-2 antibody is administered intravenously.

If adding IL-2 dosing relevant to IL-2 antibody, it is contemplated that the IL-2 is administered sequentially, for example on the same day, and in certain embodiments, the IL-2 antibody is administered prior to administration of the IL-2. In various embodiments, the IL-2 antibody is administered weekly, with weekly or multi-times per week administration of IL-2 following administration of the antibody.

In various embodiments, the IL-2 antibody is administered 1 time per week and IL-2 therapy (e.g., Proleukin) is administered on the known prescribing schedule, but at a lower IL-2 dose.

It is further contemplated that the combination of the antibodies herein and IL-2 increases the Therapeutic Index (TI) of IL-2 as an anti-tumor medication. In various embodiments, the TI of IL-2 is increased by at least 2, 3, 4, 5, 6, 7, 8, 9, 10-fold or more when administered in combination with an anti-IL-2 antibody of the disclosure.

It is contemplated that IL-2 can be administered on the same schedule as the antibody administration or if the IL-2 is administered separately from the antibody, may be administered as set out for other IL-2 therapeutics such as PROLEUKIN®, or at a reduced dose compared to previously used therapeutic doses. The currently recommended PROLEUKIN® (aldesleukin) treatment regimen is administered by a 15 minute intravenous infusion every 8 hours. The following schedule has been used to treat adult patients with metastatic renal cell carcinoma (metastatic RCC) or metastatic melanoma. Each course of treatment consists of two 5-day treatment cycles separated by a rest period. 600,000 International Units/kg (0.037 mg/kg) dose administered every 8 hours by a 15-minute intravenous infusion for a maximum of 14 doses. Following 9 days of rest, the schedule is repeated for another 14 doses, for a maximum of 28 doses per course, as tolerated. This schedule may be modified as necessary by a treating physician. It is contemplated that when IL-2 is administered with an antibody that the dosing is reduced compared to standard doses of IL-2. Additional dosing regimens are also set out below in the Detailed Description.

Chemotherapeutic and other agents contemplated but not limited for use with the antibodies of the present disclosure include, but are not limited to those listed in Table 1.

TABLE 1

| Chemotherapeutic and other agents |
|---|
| Alkylating agents |
| Nitrogen mustards |
| mechlorethamine<br>cyclophosphamide<br>ifosfamide<br>melphalan<br>chlorambucil |
| Nitrosoureas |
| carmustine (BCNU)<br>lomustine (CCNU)<br>semustine (methyl-CCNU) |
| Ethylenimine/Methyl-melamine |
| thriethylenemelamine (TEM)<br>triethylene thiophosphoramide<br>(thiotepa)<br>hexamethylmelamine<br>(HMM, altretamine) |

TABLE 1-continued

| Chemotherapeutic and other agents |
|---|
| Alkyl sulfonates |
| busulfan |
| Triazines |
| dacarbazine (DTIC) |
| Antimetabolites |
| Folic Acid analogs |
| methotrexate<br>Trimetrexate<br>Pemetrexed<br>(Multi-targeted antifolate) |
| Pyrimidine analogs |
| 5-fluorouracil<br>fluorodeoxyuridine<br>gemcitabine<br>cytosine arabinoside<br>(AraC, cytarabine)<br>5-azacytidine<br>2,2'-difluorodeoxy-cytidine |
| Purine analogs |
| 6-mercaptopurine<br>6-thioguanine<br>azathioprine<br>2'-deoxycoformycin<br>(pentostatin)<br>erythrohydroxynonyl-adenine (EHNA)<br>fludarabine phosphate<br>2-chlorodeoxyadenosine<br>(cladribine, 2-CdA) |
| Type I Topoisomerase Inhibitors |
| camptothecin<br>topotecan<br>irinotecan |
| Biological response modifiers |
| G-CSF<br>GM-CSF |
| Differentiation Agents |
| retinoic acid derivatives |
| Hormones and antagonists |
| Adrenocorticosteroids/antagonists |
| prednisone and equivalents<br>dexamethasone<br>ainoglutethimide |
| Progestins |
| hydroxyprogesterone caproate<br>medroxyprogesterone acetate<br>megestrol acetate |
| Estrogens |
| diethylstilbestrol<br>ethynyl estradiol/equivalents |
| Antiestrogen |
| tamoxifen |
| Androgens |
| testosterone propionate<br>fluoxymesterone/equivalents |
| Antiandrogens |
| flutamide<br>gonadotropin-releasing<br>hormone analogs<br>leuprolide |

TABLE 1-continued

| Chemotherapeutic and other agents |
|---|
| Nonsteroidal antiandrogens |
| flutamide |
| Natural products |
| Antimitotic drugs |
| Taxanes |
| paclitaxel |
| Vinca alkaloids |
| vinblastine (VLB) |
| vincristine |
| vinorelbine |
| Taxotere ® (docetaxel) |
| estramustine |
| estramustine phosphate |
| Epipodophylotoxins |
| etoposide |
| teniposide |
| Antibiotics |
| actimomycin D |
| daunomycin (rubido-mycin) |
| doxorubicin (adria-mycin) |
| mitoxantroneidarubicin |
| bleomycin |
| splicamycin (mithramycin) |
| mitomycinC |
| dactinomycin |
| aphidicolin |
| Enzymes |
| L-asparaginase |
| L-arginase |
| Radiosensitizers |
| metronidazole |
| misonidazole |
| desmethylmisonidazole |
| pimonidazole |
| etanidazole |
| nimorazole |
| RSU 1069 |
| EO9 |
| RB 6145 |
| SR4233 |
| nicotinamide |
| 5-bromodeozyuridine |
| 5-iododeoxyuridine |
| bromodeoxycytidine |
| Miscellaneous agents |
| Platinium coordination complexes |
| cisplatin |
| Carboplatin |
| oxaliplatin |
| Anthracenedione |
| mitoxantrone |
| Substituted urea |
| hydroxyurea |
| Methylhydrazine derivatives |
| N-methylhydrazine (MIH) |
| procarbazine |
| Adrenocortical suppressant |
| mitotane (o,p'- DDD) |
| ainoglutethimide |
| Cytokines |
| interferon (α, β, γ) |
| interleukin-2 |
| Photosensitizers |
| hematoporphyrin derivatives |
| Photofrin ® |
| benzoporphyrin derivatives |
| Npe6 |
| tin etioporphyrin (SnET2) |
| pheoboride-a |
| bacteriochlorophyll-a |
| naphthalocyanines |
| phthalocyanines |
| zinc phthalocyanines |
| Radiation |
| X-ray |
| ultraviolet light |
| gamma radiation |
| visible light |
| infrared radiation |
| microwave radiation |

Treatment of Disorders

In another embodiment, any of the types of antibodies described herein may be used in the methods. In exemplary embodiments, the target specific antibody is a human, chimeric or humanized antibody. In another exemplary embodiment, the target is human and the patient is a human patient. Alternatively, the patient may be a mammal that expresses a target protein with which the target specific antibody cross-reacts. The antibody may be administered to a non-human mammal expressing a target protein with which the antibody cross-reacts (e.g., a primate) for veterinary purposes or as an animal model of human disease.

In one embodiment, the disclosure provides a method for treating a disease, condition or disorder described herein comprising the step of administering to a subject in need thereof a therapeutically effective amount of an IL-2 antibody or a pharmaceutical composition contemplated herein.

In another embodiment, the disclosure provides a method for treating a disease, condition or disorder associated with increased IL-2 or IL-2 R expression comprising the step of administering to a subject in need thereof a therapeutically effective amount of an antibody or a pharmaceutical composition contemplated herein.

In another embodiment, the disclosure provides a method for treating a disease, condition or disorder selected from the group consisting of cancer, microbial infection, asthma and autoimmune disease.

In one embodiment, the disclosure provides a method for treating cancer or preventing the recurrence of cancer comprising administering to a subject in need thereof a therapeutically effective amount of a IL-2 antibody or a pharmaceutical composition as contemplated herein.

In various embodiments, the disclosure provides a method for ameliorating one more side effect s of IL-2-based therapy comprising administering to a subject in need thereof a therapeutically effective amount of an antibody or a pharmaceutical composition contemplated herein. Examples of such side effects include vascular leak syndrome and pulmonary edema, renal damage, CNS impairment, and cardiac effects (and such symptoms as hypotension, diarrhea, oliguria, chills, vomiting, dyspnea, rash, bilirubinemia, thrombocytopenia, nausea, confusion, creatinine increase, respiratory disorder, coma, acidosis, apnea, acute kidney failure, coagulation disorders, dyspnea, fever, heart arrest, myocardial infarction, psychosis, sepsis, SGOT increase, stupor, supraventricular tachycardia, and death).

Also provided is a method of reducing an effective IL-2 dose in a subject receiving IL-2 therapy comprising administering to a subject in need thereof a therapeutically effective amount of an antibody or a pharmaceutical composition contemplated herein. It is contemplated that administration of an IL-2 antibody described herein can decrease the dose of IL-2 in a subject required to ameliorate one or more symptoms of the disease or disorder being treated (compared to the dose required in the absence of IL-2 antibody treatment), effectively increasing the therapeutic window of IL-2 treatment.

Exemplary conditions or disorders that can be treated with antibodies (or formulations described herein) of the present disclosure include cancers, such as a cancer selected from the group consisting of esophageal cancer, pancreatic cancer, metastatic pancreatic cancer, metastatic adenocarcinoma of the pancreas, bladder cancer, stomach cancer, fibrotic cancer, glioma, malignant glioma, diffuse intrinsic pontine glioma, recurrent childhood brain neoplasm renal cell carcinoma, clear-cell metastatic renal cell carcinoma, kidney cancer, prostate cancer, metastatic castration resistant prostate cancer, stage IV prostate cancer, metastatic melanoma, melanoma, malignant melanoma, recurrent melanoma of the skin, melanoma brain metastases, stage IIIA skin melanoma; stage IIIB skin melanoma, stage IIIC skin melanoma; stage IV skin melanoma, malignant melanoma of head and neck, lung cancer, non-small cell lung cancer (NSCLC), squamous cell non-small cell lung cancer, breast cancer, recurrent metastatic breast cancer, hepatocellular carcinoma, hodgkin's lymphoma, follicular lymphoma, non-hodgkin's lymphoma, advanced B-cell NHL, HL including diffuse large B-cell lymphoma (DLBCL), multiple myeloma, chronic myeloid leukemia, chronic lymphocytic leukemia, richter's syndrome; waldenstrom macroglobulinemia, adult glioblastoma; adult gliosarcoma, recurrent glioblastoma, recurrent childhood rhabdomyosarcoma, recurrent ewing sarcoma/peripheral primitive neuroectodermal tumor, recurrent neuroblastoma; recurrent osteo sarcoma, colorectal cancer, nasopharyngeal nonkeratinizing carcinoma; recurrent nasopharyngeal undifferentiated carcinoma, cervical adenocarcinoma; cervical adenosquamous carcinoma; cervical squamous cell carcinoma; recurrent cervical carcinoma; stage IVA cervical cancer; stage IVB cervical cancer, anal canal squamous cell carcinoma; metastatic anal canal carcinoma; recurrent anal canal carcinoma, recurrent head and neck cancer; head and neck squamous cell carcinoma (HNSCC), ovarian carcinoma, colon cancer, gastric cancer, advanced GI cancer, gastric adenocarcinoma; gastroesophageal junction adenocarcinoma, bone neoplasms, soft tissue sarcoma; bone sarcoma, thymic carcinoma, urothelial carcinoma, recurrent merkel cell carcinoma; stage III merkel cell carcinoma; stage IV merkel cell carcinoma, myelodysplastic syndrome and recurrent mycosis fungoides and Sezary syndrome. In a related aspect, the disclosure provides a method for treating cancer comprising administering to a subject in need thereof a therapeutically effective amount of the antibodies or pharmaceutical compositions contemplated herein.

In certain embodiments, the cancer is selected from the group consisting of melanoma, renal cell carcinoma, lymphoma, leukemia, sarcoma, breast cancer, lung cancer, bladder cancer, colon cancer, gastric cancer, non-small cell lung carcinoma (NSCLC), bladder cancer, head and neck cancer, skin cancer, and squamous cell carcinoma (SCC).

In various embodiments, provided herein is a method of treating a disease, e.g., cancer, comprising administering an IL-2 antibody in combination with IL-2, optionally also in combination with a checkpoint inhibitor or other adjunctive oncology therapy, whereby efficacy against a non-IL-2 responsive tumor type is now made sensitive to growth and/or metastasis inhibition.

In related aspects the cancer is metastatic. In a related aspect, the metastasis includes metastasis to the bone or skeletal tissues, liver, lung, kidney or pancreas. It is contemplated that the methods herein reduce tumor size or tumor burden in the subject, and/or reduce metastasis in the subject.

In various embodiments, the methods reduce the tumor size by 10%, 20%, 30% or more. In various embodiments, the methods reduce tumor size by 10%, 15%, 20%, 25%, 30%, 35%, 40%, 45%, 50%, 55%, 60%, 65%, 70%, 75%, 80%, 85%, 90%, 95% or 100%.

In various embodiments, the methods reduce the ability of the tumor to grow and lead to stable disease as defined by standard methodologies in the field including RECIST (Response Evaluation Criteria In Solid Tumors) and irRC (immune response criteria).

In one embodiment, treatment of cancer in an animal in need of said treatment, comprises administering to the animal an effective amount of an antibody specific for IL-2 or a composition comprising an antibody described herein, optionally in combination with IL-2.

The conditions treatable by methods of the present disclosure preferably occur in mammals. Mammals include, for example, humans and other primates, as well as pet or companion animals such as dogs and cats, laboratory animals such as rats, mice and rabbits, and farm animals such as horses, pigs, sheep, and cattle.

Formulation of Pharmaceutical Compositions

To administer antibodies of the present disclosure to human or test animals, it is preferable to formulate the antibodies in a composition comprising one or more pharmaceutically acceptable carriers. The phrase "pharmaceutically or pharmacologically acceptable" refer to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like.

In addition, compounds may form solvates with water or common organic solvents. Such solvates are contemplated as well.

The antibody is administered by any suitable means, including parenteral, subcutaneous, intraperitoneal, intratumoral, intrapulmonary, and intranasal, and, if desired for local treatment, intralesional administration. Parenteral infusions include intravenous, intraarterial, intraperitoneal, intramuscular, intradermal or subcutaneous administration. In addition, the antibodies may be suitably administered by pulse infusion, particularly with declining doses of the antibody. Preferably the dosing is given by injections, most preferably intravenous, intra muscular or subcutaneous injections, depending in part on whether the administration is brief or chronic. Other administration methods are contemplated, including topical, particularly transdermal, transmucosal, rectal, oral or local administration e.g. through a catheter placed close to the desired site.

Pharmaceutical compositions of the present disclosure containing the antibodies described herein as an active ingredient may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present disclosure.

Formulation of the pharmaceutical composition will vary according to the route of administration selected (e.g., solution, emulsion). An appropriate composition comprising the antibody to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

A variety of aqueous carriers, e.g., sterile phosphate buffered saline solutions, bacteriostatic water, water, buffered water, 0.4% saline, 0.3% glycine, and the like, and may include other proteins for enhanced stability, such as albumin, lipoprotein, globulin, etc., subjected to mild chemical modifications or the like.

Therapeutic formulations of the antibodies are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16$^{th}$ edition, Osol, A. Ed. (1980).

The formulations to be used for in vivo administration must be sterile. This is readily accomplished by filtration through sterile filtration membranes.

Aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate.

The antibodies described herein can be lyophilized for storage and reconstituted in a suitable carrier prior to use. This technique has been shown to be effective with conventional immunoglobulins. Any suitable lyophilization and reconstitution techniques can be employed. It will be appreciated by those skilled in the art that lyophilization and reconstitution can lead to varying degrees of antibody activity loss and that use levels may have to be adjusted to compensate.

The IL-2 antibodies described herein can be prepared and administered as a co-formulation with one or more additional antibodies. In one aspect, at least two of the antibodies recognize and bind different antigens. In another aspect, at least two of the plurality of antibodies can specifically recognize and bind different epitopes of the same antigen.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above.

The concentration of antibody in these formulations can vary widely, for example from less than about 0.5%, usually at or at least about 1% to as much as 15 or 20% by weight and will be selected primarily based on fluid volumes, viscosities, etc., in accordance with the particular mode of administration selected. Thus, a typical pharmaceutical composition for parenteral injection could be made up to contain 1 ml sterile buffered water, and 50 mg of antibody. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, Remington's Pharmaceutical Science, 15th ed., Mack Publishing Company, Easton, Pa. (1980). An effective dosage of antibody is within the range of 0.01 mg to 1000 mg per kg of body weight per administration.

The pharmaceutical compositions may be in the form of a sterile injectable aqueous, oleaginous suspension, dispersions or sterile powders for the extemporaneous preparation of sterile injectable solutions or dispersions. The suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. The carrier can be a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In all cases the form must be sterile and must be fluid to the extent that easy syringability exists. The proper fluidity can be maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms can be brought about by various antibacterial and antifungal agents, for example, parabens, chlorobutanol, phenol, sorbic acid, thimerosal, and the like. In many cases, it will be desirable to include isotonic agents, for example, sugars or sodium chloride. Prolonged absorption of the injectable compositions can be brought about by the use in the compositions of agents delaying absorption, for example, aluminum monostearate and gelatin.

Compositions useful for administration may be formulated with uptake or absorption enhancers to increase their efficacy. Such enhancers include for example, salicylate, glycocholate/linoleate, glycholate, aprotinin, bacitracin, SDS, caprate and the like. See, e.g., Fix (*J. Pharm. Sci.*, 85:1282-1285 (1996)) and Oliyai and Stella (*Ann. Rev. Pharmacol. Toxicol.*, 32:521-544 (1993)).

Antibody compositions are contemplated for use to modulate target activity, including binding of the target to its cognate receptor or ligand, target-mediated signaling, and the like. In particular, the compositions exhibit inhibitory properties at concentrations that are substantially free of side effects, and are therefore useful for extended treatment protocols. For example, co-administration of an antibody composition with one or more other agents, e.g. IL-2, PD-1 inhibitors, PD-L1 inhibitors, CTLA-4 inhibitors, can achieve beneficial inhibition of a condition or disorder being treated, while effectively reducing the toxic side effects in the patient.

In addition, the properties of hydrophilicity and hydrophobicity of the compositions contemplated for use in the present disclosure are well balanced, thereby enhancing their utility for both in vitro and especially in vivo uses, while other compositions lacking such balance are of substantially less utility. Specifically, compositions contemplated for use in the disclosure have an appropriate degree of solubility in aqueous media which permits absorption and bioavailability in the body, while also having a degree of solubility in lipids which permits the compounds to traverse the cell membrane to a putative site of action. Thus, antibody compositions contemplated are maximally effective when they can be delivered to the site of target antigen activity.

Administration and Dosing

In one aspect, methods of the present disclosure include a step of administering a pharmaceutical composition comprising an antibody described herein. In certain embodiments, the pharmaceutical composition is a sterile composition.

Methods of the present disclosure are performed using any medically-accepted means for introducing therapeutics directly or indirectly into a mammalian subject, including but not limited to injections, oral ingestion, intranasal, topical, transdermal, parenteral, inhalation spray, vaginal, or rectal administration. The term parenteral as used herein includes subcutaneous, intravenous, intramuscular, and intracisternal injections, as well as catheter or infusion techniques. Administration by intradermal, intratumoral, intramammary, intraperitoneal, intrathecal, retrobulbar, intrapulmonary injection and or surgical implantation at a particular site is contemplated as well.

In one embodiment, administration is performed at the site of a cancer or affected tissue needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations of the disclosure implanted near or at site of the cancer.

Therapeutic compositions may also be delivered to the patient at multiple sites. The multiple administrations may be rendered simultaneously or may be administered over a period of time. In certain cases it is beneficial to provide a continuous flow of the therapeutic composition. Additional therapy may be administered on a period basis, for example, once per week, once every 2 weeks, twice per month, once monthly, once every two months, or once every three months, or at a longer interval.

The amounts of antibody composition in a given dosage may vary according to the size of the individual to whom the therapy is being administered as well as the characteristics of the disorder being treated. In exemplary treatments, it may be necessary to administer about 1 mg/day, 5 mg/day, 10 mg/day, 20 mg/day, 50 mg/day, 75 mg/day, 100 mg/day, 150 mg/day, 200 mg/day, 250 mg/day, 500 mg/day or 1000 mg/day. These concentrations may be administered as a single dosage form or as multiple doses. Standard dose-response studies, first in animal models and then in clinical testing, reveals optimal dosages for particular disease states and patient populations.

Also contemplated in the present disclosure, the amounts of IL-2 antibodies in a given dosage may vary according to the size of the individual to whom the therapy is being administered as well as the characteristics of the disorder being treated. The antibody compositions can be administered in a dose range of 0.1 to 15 mg, twice weekly as an intravenous infusion over 30-60 minutes every 1, 2 or 4 weeks until disease progression or unacceptable toxicity. In various embodiments, the antibody compositions can be administered subcutaneously or intramuscularly, in a dose range of 0.3-30 mg/kg twice weekly or every 1, 2 or 4 weeks. In various embodiments, the dose can be 1, 2, 3, 4, 5, 6, 7, 8, 9, or 30 mg/kg. In various embodiments, the antibody compositions can be administered intravenously in a dose range of 0.3 to 3 mg/kg twice weekly or every 1, 2 or 4 weeks. Alternatively, the antibody compositions can be administered subcutaneously or intramuscularly in a dose range of 0.5-5 mg/kg twice weekly or every 1, 2 or 4 weeks.

In various embodiments, when IL-2 is given in combination with IL-2 antibodies, the dose of IL-2 administered is in the range of about 0.05 mg/kg to 1 mg/kg, or about 0.05 to 0.5 mg/kg. In various embodiments, the IL-2 when given in combination with IL-2 antibodies is in a dose of about 0.05 mg/kg, 0.1 mg/kg, 0.15 mg/kg, 0.2 mg/kg, 0.25 mg/kg, 0.3 mg/kg, 0.4 mg/kg, 0.5 mg/kg, 0.6 mg/kg, 0.75 mg/kg, or 1.0 mg/kg, or when given as a weight amount administered in a dose of about 1.0 μg-50 μg, or about 1.0 μg, 3.0 μg, 5.0 μg, 7.5 μg, 10 μg, 12.5 μg, 15 μg, 20 μg, 25 μg, 30 μg, 35 μg, 40 μg, or 50 μg. Anti-IL2 mAb dosing range may be 0.05 to 5 mg/kg. In various embodiments, the IL-2 antibody is administered at a dose of about 0.05 mg/kg, 0.25 mg/kg, 0.5 mg/kg, 0.75 mg/kg, 1.0 mg/kg, 1.25 mg/kg, 1.5 mg/kg, 2.0 mg/kg, 2.5 mg/kg, 3.0 mg/kg, 3.5 mg/kg, 4.0 mg/kg, 4.5 mg/kg or 5 mg/kg, or when given as a weight amount administered in a dose of about 50 to 1000 mg, or about 30 mg, 50 mg, 100 mg, 125 mg, 150 mg, 200 mg, 250 mg, 300 mg, 350 mg, 400 mg, 450 mg, 500 mg, 600 mg, 650 mg, 700 mg, 750 mg, 800 mg, 850 mg, 900 mg, 950 mg or 1000 mg. For example, a 1:1 molar ratio of mAb:IL2 administered in mice may be dosed as 15 ug:1.5 ug (i.e. 0.75 mg/kg:0.075 mg/kg). An exemplary dose regimen in humans may be approximately 0.1 mg/kg mAb+0.01 mg/kg IL-2 if premixed, or 1-5 mg/kg mAb+0.005 to 0.05 mg/kg IL-2 if given separately.

It will also be apparent that dosing may be modified if additional therapeutics are administered in combination with therapeutics of the disclosure.

Kits

As an additional aspect, the disclosure includes kits which comprise one or more compounds or compositions packaged in a manner which facilitates their use to practice methods of the disclosure. In one embodiment, such a kit includes a compound or composition described herein, packaged in a container such as a sealed bottle or vessel, with a label affixed to the container or included in the package that describes use of the compound or composition in practicing the method. Preferably, the compound or composition is packaged in a unit dosage form. The kit may further include a device suitable for administering the composition according to a specific route of administration or for practicing a screening assay. Preferably, the kit contains a label that describes use of the antibody composition.

Additional aspects and details of the disclosure will be apparent from the following examples, which are intended to be illustrative rather than limiting.

EXAMPLES

Example 1: Panning for High Affinity Antibodies Against IL-2

Recombinant human IL-2 (C125A mutant, Reprokine, Rehovot, Israel) was biotinylated using the EZ-link Micro NHS-PEG4-biotinulation kit (Pierce, Rockford, Ill.) according to the manufacturer's protocol using a 1:10 ratio of IL-2 to biotin reagent.

A single-chain Fv (scFv) phage display library (XOMA, Berkeley, Calif.) was panned with the biotinylated IL-2 using a soluble panning method. Kappa and lambda sublibraries were panned separately. For the first round of phage panning, 50× library equivalents (~7×10$^{12}$ cfu for kappa and ~1×10$^{13}$ for lambda) of the library were blocked for 1 hr at room temperature with rotation by mixing 1:1 with 10% milk/PBS. Binders to streptavidin were deselected from blocked phage by adding blocked phage to streptavidin-coated magnetic DYNABEADS® M-280 (ThermoFisher) and incubating with rotation for 45 minutes. The deselection step was repeated once more. A magnet was used to separate beads from phage. Concurrent with the deselection steps, 200 pmoles of biotinylated IL-2 was allowed to bind streptavidin-coated magnetic DYNABEADS® M-280 by incubating at room temperature with rotation for 45 minutes. Selection was done by adding deselected phage to biotinylated IL-2 bound to magnetic streptavidin beads (100 pmol per sublibrary) and incubating with rotation for 1.5 hours. After selection, unbound phage was washed from the beads 3 times with 0.5% milk/PBS-0.1% TWEEN for 5 minutes each followed by an additional three 5-minute washes with 0.5% milk/PBS. Bound phage was eluted from beads after the wash step by the addition of 100 mM triethylamine and incubating with rotation at room temperature for 30 minutes. Eluted phage was neutralized with the addition of an equal volume of 1 M Tris-HCl, pH 7.4. Eluted and neutralized phage was then collected into a 50 mL Falcon tube (Falcon No 352070) and used to infect log-phase growing TG1+cytFkpA bacterial cells (OD600 ~0.5). Infection was at 37° C. for 30 min without shaking, followed by 30 min additional incubation at 37° C. with shaking at 100 rpm. Cells were plated on 2×YT media supplemented with 100 ug/mL Carbenicillin, 34 μg/mL Chloramphenicol and 2% Glucose (2YTCCmG) agar bioassay plates and incubated overnight at 30° C. to allow for overnight lawn growth.

In preparation for use as input for the next round, 100× of previous round output was rescued by superinfection using M13K07 helper phage. This was done by inoculating 2×YTCm media with cells scraped from previous panning round outputs. OD600 nm was measured for starting culture and adjusted to reflect a starting OD600 nm of ~0.05. Cells were grown at 37° C. with shaking until cells reached log-growing phase of OD600 nm ~0.5. Cells were infected with M13K07 (New England Biolabs, MA) at a multiplicity of infection (MOI)=~20, at 37° C. for 30 min without shaking, followed by an additional 30 min incubation at 37° C. with shaking at 150 rpm. After infection at 37° C., cells were pelleted and transferred to new 2×YT media supplemented with 25 ug/mL Kanamycin, 100 ug/mL Carbenicillin and 2% Arabinose (2YTCKAra). Cultures were grown overnight at 25° C. Phage was separated from cells and debris by centrifugation and resulting supernatant was recovered and used as input for the next panning round. Selection enrichment was monitored by the amount of input used for each panning round and the resulting phage output titer.

For the second and third panning rounds, the same solution phase protocols followed in round one were used with the following exceptions. Phage input amount used in panning rounds two and three was ~1.0×10$^{10}$ cfu. For round two, 25 and 10 pmoles of biotinylated antigen were used in selection, and for round three, 10 pmoles of biotinylated antigen were used. In round two, unbound phage were washed from the beads 5 times with 0.5% milk/PBS-0.1% TWEEN for 5 minutes each followed by an additional five 5-minute washes with 0.5% milk/PBS. In round three panning, beads were washed 5 times with 0. 5% milk/PBS-0.1% TWEEN for 5 minutes then 3 quick washes with 0.5% milk/PBS-0.1% TWEEN, followed by five 5-minute washes and 3 quick washes with 0.5% milk/PBS.

Example 2: Screening for Antibodies in Periplasmic Extracts

Bacterial periplasmic extracts (PPEs) containing secreted antibody fragments for use in screening for IL-2 binders were prepared by standard methods. Individual colonies were picked into 96-well plates filled with 2YTC supplemented with 100 ug/mL Carbenicillin and 0.1% glucose media. Cultures were allowed to grow at 37° C. with shaking until log growing phase was reached (OD600 nm=0.5). Colonies were then induced to produce soluble fragment antibodies by adding 1 mM IPTG final and incubated overnight at 25° C. with shaking. PPEs containing soluble fragment antibodies were prepared from the induced cells using the standard method of adding 1:3 volume ratio of ice-cold PPB solution (Teknova, Hollister, Calif.) and double distilled water (ddH20) with complete EDTA free protease inhibitor cocktail tablets (Roche, Ind.).

ELISA

PPEs were assayed by ELISA as follows. 384-well Streptavidin coated plates (Thermo Fisher Scientific, Rochester, N.Y.) or 384-well MaxiSorp (Thermo Fisher Scientific, Rochester, N.Y.) were coated overnight at 4° C. with biotinylated IL-2 (1 µg/mL in PBS) for streptavidin-coated plates, IL-2 (1 µg/mL in PBS) for MaxiSorp plates or PBS (as controls). PPEs were blocked with 5% BSA/PBS for 1 hr and then added to the coated ELISA plate (20 µl/well) and incubated for 1 hr at room temperature (RT). Bound scFv fragments were detected with murine anti-V5 mAb (Sigma) for 1 hr at RT followed by goat anti-mouse HRβ-conjugated antisera (Thermo Scientific, Rockford, Ill.). Three washes with PBS-0.1% TWEEN-20 (Teknova, Hollister, Calif.) were performed following every stage of the ELISA screens. Color was developed at 450 nm absorbance with 20 µl/well soluble 3.3', 5.5'-tetramethylbenzidine (TMB) substrate (KPL) and stopped with 1 M H2SO4 (20 µl/well).

Samples that measured >3-fold over background in binding to biotinylated rhIL-2 captured by streptavidin, and <3-fold over background in binding to streptavidin alone in primary screening were designated as primary hits. Primary hits were picked and rearrayed onto new plates, and PPEs were prepared and rescreened as above. Samples that again measured >3-fold over background in binding IL-2 and <3-fold in binding on a control plate were designated as secondary hits. Secondary hits were again rearrayed, then PPEs were screened by ELISA on rhIL-2 coated directly onto plates for a tertiary screen.

Reformatting

The DNA sequences of secondary hits were determined, and 13 unique clones that bound in the tertiary screen were reformatted into IgG2 format. The variable heavy (VH) and light (VL) chains of the selected hits were PCR-amplified, cloned into plasmid vectors containing antibody constant region sequences, and transiently transfected into 293E cells using standard methods to generate material for further characterization.

Binding by SPR

For preliminary kinetic binding analysis, IgGs in culture supernatants were injected over immobilized anti-human Fc surfaces on the ProteOn X100 (Biorad), followed by injection of 5 concentrations of rhIL-2 or by running buffer (HBS-EP+ with 1% BSA), using standard methods for kinetic binding analysis. Using the ProteOn analysis software, affinities were estimated to be in the single- to double-digit nM range (Table 2). To determine whether these antibodies compete with IL-2 receptor binding, a second experiment tested whether soluble IL-2 Rβ (R&D Systems) could bind to IL-2 bound by similarly captured IgGs. Three of the antibodies, XPA.92.011, XPA.92.012 and XPA.92.013, clearly allowed binding of IL-2 Rβ, while no such binding could be detected to IL-2 captured by the other 10 antibodies (Table 2).

TABLE 2

IL-2 antibodies binding to recombinant human IL-2 (rhIL-2) and IL-2 Rβ measured by SPR.

| Antibody | rhIL-2 affinity (nM) | Allows Rβ binding |
| --- | --- | --- |
| XPA.92.001 | 4.9 | No |
| XPA.92.002 | 20.2 | No |
| XPA.92.003 | 3.9 | No |
| XPA.92.004 | 98 | No |
| XPA.92.005 | 5.5 | No |
| XPA.92.006 | 3.5 | No |
| XPA.92.007 | 2.1 | No |
| XPA.92.008 | 3.0 | No |
| XPA.92.009 | 3.3 | No |
| XPA.92.010 | 17 | No |
| XPA.92.011 | 2.3 | Yes |
| XPA.92.012 | 27 | Yes |
| XPA.92.013 | 41 | Yes |

Affinity Maturation

Because the affinities of the three IL-2 Rβ-permissive antibodies were low, with rapid kinetics, they were subjected to affinity maturation using light chain shuffling. The VH region from each of the three antibodies was cloned into a library of VLs. This new Fab library was panned against biotinylated IL-2 using a solution phase protocol.

Panning Light Chain Shuffled Library

For the first round of phage panning, ~$1\times10^{11}$ phage from the affinity maturation library was blocked for 1 hr at room temperature with rotation by mixing 1:1 with SuperBlock (ThermoFisher). Binders to streptavidin were deselected from blocked phage by adding blocked phage to streptavidin-coated magnetic DYNABEADS® M-280 and incubating with rotation for 30 minutes. The deselection step was repeated once more. A magnet was used to separate beads from phage. Concurrent to the deselection steps, 10 pmoles of biotinylated IL-2 was allowed to bind streptavidin-coated magnetic DYNABEADS® M-280 by incubating at room temperature with rotation for 1 hour. Selection was done by adding deselected phage to biotinylated IL-2 bound to magnetic streptavidin beads and incubating with rotation for 1.5 hours. After selection, unbound phage was washed from the beads 5 times with 0.5% Superblock PBS-0.1% TWEEN for 5 minutes each followed by an additional three 5-minute washes with 0.5% Superblock PBS. Bound phage was eluted from beads after the wash step by the addition of 100 mM triethylamine and incubating with rotation at room temperature for 30 minutes. Eluted phage was neutralized with the addition of equal volume 1M Tris-HCl, pH 7.4. Eluted neutralized phage was then collected into a 50 mL Falcon tube (Falcon No 352070) and used to infect log growing TG1+cytFkpA bacterial cells (OD600 ~0.5). Infection was at 37° C. for 30 min without shaking, followed by 30 min additional incubation at 37° C. with shaking at 100 rpm. Cells were plated on 2×YT media supplemented with 100 ug/mL Carbenicillin, 34 µg/mL Chloramphenicol and 2% Glucose (2YTCCmG) agar bioassay plates and incubated overnight at 30° C. to allow for overnight lawn growth.

To remove contaminating parental scFv clones, DNA from the round 1 output was digested with NheI-HF (NEB) and BsmI, which both cut scFv phagemids but not Fab phagemids. The resulting DNA was transformed into TG1+ cytFkpA cells and phage was produced as described above.

An additional round of panning was completed using a similar protocol as round 1 with the following changes. A KingFisher instrument was used to do three 30 minute deselections of ~$5\times10^{10}$ phage against streptavidin-coated magnetic DYNABEADS® M-280. 1 pmole of biotinylated IL-2 was coated onto streptavidin-coated magnetic DYNA-BEADS® M-280 to which the deselected phage was added and incubated for 1 hour using the KingFisher for mixing. Finally, unbound phage were washed from the beads 5 times with 0.5% Superblock/PBS-0.1% TWEEN for 5 minutes each followed by an additional five times 5-minute washes with 0.5% Superblock/PBS.

Kinetic Ranking by SPR

Primary screening of affinity matured clones was carried out by SPR using the Biacore 4000 for off-rate ranking. A Biacore CM5 chip was prepared by amine coupling following the manufacturer's instructions and reagents (Biacore), with anti-Fab capture reagent immobilized on spots 1, 2, 4, and 5 of all four flow cells. Four 96-well plates of PPEs were prepared as described above, then diluted 1:1 with Biacore running buffer (HBS-EP+ with 1% BSA) and filtered through 0.2 µm Multiscreen plates (Millipore) by centrifugation. Diluted, filtered PPEs were injected for 3 minutes over spots 1 or 5, followed by 3 minutes injection of buffer or 50 nM IL-2 in high performance mode at 30 µL/min. Dissociation was monitored for 5 minutes. IL-2 injections were double-referenced using spots 2 or 4 and the no IL-2 buffer injection. Data were analyzed using the Biacore 4000 Evaluation software. Thirty-seven samples with >45 RU of Fab captured and an off-rate of <0.01 sec-1 were designated as hits and moved into further screening.

Samples designated as hits were sequenced and re-screened by SPR as described above, except that PPEs were injected for 2 minutes, and IL-2 was injected at 30, 10, 3 and 0 nM. Data were analyzed by fitting both on- and off-rates, from which affinity estimates were calculated to range from 10 nM to 0.06 nM.

Example 3: Additional Screening for IL-2-Modulating Antibodies

CHO-K1 cells were engineered to express human IL-2 receptors for use in novel screening and functional assays of anti-IL-2 antibodies. Stable clones of CHO-K1 cells expressing high, medium or low levels of IL-2 Rα (CHO/Rα), IL-2 Rβ (CHO/Rβ), or IL-2 Rβ and γc (CHO/Rβγ) were selected using Fluorescence Activated Cell Sorting (FACS) methods known in the art. The murine-derived BaF3 cell line was transfected with human IL-2 receptors to confer IL-2 responsiveness, and the resulting cell line was weaned to IL-2 and used for characterization of antibody activity in proliferation assays. Expression levels (number of receptors/cell) were estimated and multiple lines were tested for optimal performance in binding, signaling, or proliferation assays. The following cell line clones were chosen for use in various assays (Table 3).

TABLE 3

Human IL-2 receptor expression levels (receptors/cell).

| Cell line (clone#) | Rα | Rβ | Rγ |
|---|---|---|---|
| CHO/IL-2 Rα (#6) | 2e5 | — | — |
| CHO/IL-2 Rβ (#4-29) | — | 6e5 | — |
| CHO/IL-2 Rβγ (#20-21) | — | 2e5 | 2.5e5 |
| CHO/IL-2 Rβγ (#17) | — | 8e3 | 1e4 |
| BaF3/IL-2 Rβγ (#66) | — | 2e4 | 7e3 |
| NK92 | 4e3 | 5e3 | 6e3 |

— Not transfected with human IL-2 receptor gene

Flow Cytometry Screening of Periplasmic Extracts (PPEs)

In order to identify antibodies with desired properties, PPEs containing soluble antibody fragments were screened on CHO/Rα, CHO/Rβ, CHO/Rβγ, and parental CHO-K1 cells with and without saturating amounts of IL-2. The screen identified clones that 1) do not bind to CHO/Rα or parental cells, and 2) that bind to CHO/Rβ or CHO/Rβγ cells in the presence but not absence of IL-2. Cells were grown in Excel302 and 2 mM L-glutamine (Sigma #14324C-500 mL). On the day of testing, cells were washed, stained and resuspended in FACs buffer (PBS and 5% BSA and 0.1% Sodium Azide). CHO-K1 and CHO/Rβ cells were stained with CFSE (Invitrogen #C34554) or Cell Trace Brilliant Violet (Invitrogen #34557). Stained CHO-K1 and CHO/Rβ were with mixed with unstained CHO/Rβγ cells. To each well in a 96-well V-bottom plate (Costar) containing soluble antibody fragment (PPE), CHOk1, CHOk1-IL-2Rβ and CHO/Rβγ cells and IL-2 were added so that each well contain 50,000 of each cell type plus IL-2 (Reprokine #RK60568) at a final concentration of 100 nM. In another separate 96-well V-bottom plate with wells containing PPE prepared from the same batch, CHO-K1 cells stained with CFSE were mixed with unstained CHO/Rα (50,000 of each cell type per well) and IL-2 at a final concentration of 100 nM. All the samples were allowed to incubate at 4° C. for 1-2 hours, then washed with FACs Buffer. Next, 1 µg/mL mouse anti-c-myc (Roche #11667149001) was added to cells and allowed to incubate for 1 hour at 4° C. After incubation, cells were washed again and anti-mouse heavy chain and light chain antibody (Jackson Immunoresearch #115-136-146) was added to cells at a dilution of 1:1000 and incubated for 30 minutes to 1 hour at 4° C. Samples were analyzed using FACScan flow cytometer. Samples which showed binding at least 2-fold greater on CHO/Rβ or CHO/Rβγ cells compared to parental CHO-K1 cells, and less than 2-fold binding on CHO/Rα cells, were selected for further characterization.

Flow Cytometry Screening of Purified IgGs

After phage-derived antibody fragments were reformatted into full-length human IgGs, the purified antibodies were screened on CHO/Rα, CHO/Rβ, CHO/Rβγ, and parental CHO-K1 cells grown and stained as described above. To characterize the binding potency of the anti-IL-2 antibodies, IgG was serially titrated and added to wells containing cells and a fixed final concentration of IL-2 (Reprokine #RK60568). In another test, IL-2 was serially titrated and added to wells containing cells and a fixed amount of anti-IL-2 antibody to measure the binding efficacy of the antibody. This was allowed to incubate at 4° C. for 1 to 1.5 hours. Bound antibody was detected by the addition of anti-human heavy chain and light chain (Jackson Immuno Research #109-136-088) at 1:1000 and incubating at 4° C. for 30 minutes to 1 hour. Samples were analyzed using BD FACs Canto flow cytometer. Binding of purified antibodies in the presence of increasing concentrations of IL-2 to CHO cells expressing different IL-2 R chains is shown in FIGS. 2A-2D. Titration of selected purified antibodies in the presence of constant [IL-2] is shown in FIGS. 3A-3D. The EC50s of antibodies binding to cells as measured by flow cytometry is shown in Table 4.

TABLE 4

EC$_{50}$ of IL-2/mAb complexes binding to cells expressing
human IL-2 Receptors (concentration of antibody
at which half-maximal binding is observed).

| Antibody | CHO/IL-2 Rβ (#4-29) (nM) | CHO/IL-2 Rβγ (#20-21) (nM) | Ratio Rβ/Rβ + γc |
|---|---|---|---|
| XPA.92.019 | 23 | 1.3 | 18 |
| XPA.92.041 | 22 | 2.5 | 9 |
| XPA.92.042 | 25 | 2.6 | 10 |
| XPA.92.099 | 76 | 2.0 | 38 |

Example 4: IL-2 Induced Cell Proliferation

Background and Approach

In order to evaluate the relative effect of antibodies on cells expressing the high affinity trimeric or lower affinity dimeric IL-2 R complexes, a cell proliferation assay using two cell lines was employed. The human cell line of the NK lineage, NK-92, and the mouse lymphocyte cell line BaF3 transfected with the human IL-2 receptor β and γ chains, both show proliferative activity in response to IL-2. The NK-92 cell line expresses all three chains that are required to form the trimeric high affinity IL-2 receptor complex, Rα, Rβ, and γc, and is dependent on IL-2 for growth. The BaF3 cells are normally dependent on IL-3 for growth, however, once transfected with IL-2 receptors the cells were weaned off of IL-3 and transitioned to IL-2 for growth dependency. The BaF3 clone used for these experiments was transfected with only the IL-2 Rβ and γc chains, and thus signals through the lower affinity dimeric complex of the human IL-2 receptor. Evaluation of the effect of antibody modulation of IL-2 induced proliferation on cells expressing either the high affinity trimeric IL-2 receptor complex (NK-92 cells, IL-2 Rαβγ), or the lower affinity dimeric complex (BaF3 cells, IL-2 Rβγ) was performed. This enabled a comparison of the extent of inhibition of IL-2-induced proliferation mediated by the different receptor complexes, including demonstration of the effects on cell proliferation of antibodies which primarily blocked the IL-2 Rα interaction.

Method

NK-92 cells were maintained in αMEM (Life Technologies) with 12.5% FBS, 12.5% Horse Serum (Hyclone), 0.2 mM inositol, 0.02 mM folic acid (Sigma Aldrich); 0.1 mM 2-mercaptoethanol (Life Technologies), with 15 ng/mL human IL-2 (Reprokine, Valley Cottage N.Y.). BaF3 IL-2 Rβγ cells were maintained in RPM with 10% FBS, 0.4 mg/mL Geneticin (Life Technologies) and 100 ng/mL hIL-2. Cells were centrifuged to pellet, washed in DPBS, and resuspended in complete growth medium without IL-2 overnight. Following overnight IL-2 withdrawal, the cells were washed again and seeded at 25,000 cells/well into opaque flat bottom 96 well plates in the cells respective growth media without IL-2.

IL-2 titrations and antibody dilutions were mixed and incubated for 30 minutes at 37° C. prior to addition to the cells. Following the incubation, these samples were added to the culture plates with the cells to achieve the final concentrations in 100 μL per well, and the plates were placed in a 37° C. incubator for 48 hours. The final antibody concentration in the IL-2 titration assays was 30 μg/mL.

After 48 hours in the incubator, the plates were removed and allowed to equilibrate to room temperature. CellTiter-Glo solution, 100 μL/well (Promega, Madison Wis.), was added to each well. Plates were then placed on a shaker for two minutes to induce cell lysis, incubated an additional 8 minutes at room temperature, and then read on a FlexStation 3 Luminometer with 500 mS integration (Molecular Devices, Sunnyvale Calif.). The luminescence values were analyzed in Prism (GraphPad Software, La Jolla Calif.) using a sigmoidal dose response four parameter fit to determine EC50 values as presented in FIGS. 4A, 4B and 4C. These results show that IL-2 antibodies, XPA.92.019, XPA.92.041, XPA.92.042 and XPA.92.099 have a greater effect on proliferation of cells expressing all three receptors (Rαβγ) than on cells expressing just the βγ complex (Rβγ). The IL-2 antibodies, XPA.92.019, XPA.92.041, XPA.92.042 and XPA.92.099 were also found to inhibit IL-2-induced proliferation in cells expressing IL-2 Rαβγ (NK92 and CTLL-2 cells) and IL-2 Rβγ (BaF3 cells) to a greater extent than the MAB602 control antibody (FIGS. 5A-5C, respectively).

TABLE 5

Proliferation assays: EC$_{50}$ of mAb/IL-2 complex
compared to EC$_{50}$ of unbound IL-2 (fold EC$_{50}$ shift)
in cells expressing human receptors

| Antibody | NK92 (huRαβγ) (Fold EC$_{50}$ shift) | BaF3/IL-2 HuRβγ (Fold EC$_{50}$ shift) | Ratio (huRαβγ/Rβγ) |
|---|---|---|---|
| XPA.92.019 | 33 | 5.2 | 6 |
| XPA.92.041 | 35 | 3.9 | 9 |
| XPA.92.042 | 52 | 5.0 | 10 |
| XPA.92.099 | 22 | 2.4 | 9 |
| For comparison: MAB602 | 15 | 1.2 | 13 |

TABLE 6

Proliferation assays: EC$_{50}$ of mAb/IL-2 complex
compared to EC$_{50}$ of unbound IL-2 (fold EC$_{50}$ shift)
in cells expressing mouse receptors

| Antibody | CTLL-2 (muRαβγ) (Fold EC$_{50}$ shift) |
|---|---|
| XPA.92.019 | 130 |
| XPA.92.041 | 58 |
| XPA.92.042 | 156 |
| XPA.92.099 | 54 |
| For comparison: MAB602 | 18 |

Example 5: SPR Studies

Antibody affinities were measured by SPR using the Biacore 4000 with a standard capture methodology. Briefly, anti-human IgG (Fc specific) from an anti-human antibody capture kit (Biacore) was immobilized onto spots 1, 2, 4, and 5 of all four flow cells of a CM-5 sensor chip by amine coupling according to the manufacturer's instructions. Running buffer was HBS-EP+ with 1% BSA. Antibodies at 2 μg/mL were injected for 2 minutes at a flow rate of 10 μL/min. rhIL-2 was injected in triplicate at 5 concentrations from 0.11 nM-10 nM in 3-fold serial dilutions for 3 minutes, and dissociation was monitored for 10 minutes. Data were analyzed using the Biacore 4000 Evaluation software. Affinities are shown in Table 7.

TABLE 7

Kinetics and affinities of selected antibodies for human IL-2.

| Antibody | $k_a$ (M$^{-1}$s$^{-1}$) | $k_d$ (s$^{-1}$) | $K_D$ (M) |
|---|---|---|---|
| XPA.92.019 | 3.7e6 | 3.4e−5 | 9.5e−12 |
| XPA.92.041 | 5.6e6 | 3.2e−4 | 5.8e−11 |
| XPA.92.042 | 8.9e6 | 2.5e−4 | 2.8e−11 |
| XPA.92.099 | 5.5e6 | 2.4e−4 | 4.4e−11 |
| For comparison: MAB602 | | | 1.2e−10 |

The species cross-reactivity of IL-2 antibodies with human, rabbit, and mouse IL-2 was determined by SPR as described above, except that IL-2 was injected in duplicate at 4 concentrations in 3-fold serial dilutions from 30 nM to 1 nM. The amino acid sequences of IL-2 from other species, compared to the human sequence, is shown in FIG. 6. Sequences of IL-2 from a number of species were retrieved from the PubMed structure database (pig: caa40071; rat: aaa41427; rabbit: np_001156652; human: np_000577; mouse: aab39206). These sequences were imported into vector NTI® (Lifetech) and aligned using the alignx tool. Affinity estimates are summarized in Table 8.

TABLE 8

Species cross-reactivity: Affinities of IL-2 antibodies for IL-2 from mouse, rat or rabbit.

| Antibody | Mouse (M) | Rat (M) | Rabbit (M) |
|---|---|---|---|
| XPA.92.019 | 1e−7 | >1e−6 | 2e−10 |
| XPA.92.041 | 4e−8 | 1e−9 | 5e−10 |
| XPA.92.042 | 1e−8 | 6e−9 | 6e−10 |
| XPA.92.099 | No binding | No binding | 9e−11 |
| For comparison: MAB602 | 1e−8 | Not tested | Not tested |

Example 6: Functional Signaling Assays with Endogenously Expressing Cell Lines The presence of the IL-2 Rα (CD25) increases the affinity of the dimeric IL-2 Receptor (IL-2 Rβγ) for IL-2 cytokine. In humans, many immune cells express only the dimeric receptor, including naïve and memory T cells and CD56dim NK cells. In contrast, the trimeric IL-2 R (IL-2 Rαβγ) is found on regulatory T cells, CD56bright NK cells and is transiently expressed by effector T cells. Cell lines with endogenous levels of IL-2 R expression maintain levels of receptor and signaling components at native ratios and contain signaling pathways that are intact. Activation of transcription factor Signal Transducer and Activator of Transcription 5 (STAT5) is a key early signaling event mediated by IL-2 through the IL-2 receptor. The consequence of STAT5 phosphorylation is increased expression of a variety of genes involved in cellular processes such as proliferation, survival and apoptosis. To assess the ability of anti-IL-2 antibody candidates to impact IL-2 signaling on cell lines with endogenous expression of human IL-2 Rαβγ or IL-2 Rβγ components, phosphorylation of STAT5a and b was measured as described below.

Phosphorylation of STAT5a,b in Human NK-92 Cell Line

To compare the ability of antibody/IL-2 complexes to induce phosphorylation of STAT5 on cells which expressed the trimeric receptor (IL-2 Rαβγ), the NK-92 cell line (ATCC) was utilized. This is an NK cell line which is dependent on IL-2 for growth and which maintains cytotoxic capabilities and characteristic NK cell surface markers. It is uniformly high for expression of CD25 (IL-2 Rα). Cells were washed twice followed by an overnight starvation in RPMI-1640 media (Life Technologies) with 10% FBS (Hyclone) but without IL-2 in a 37° C., 5% CO$_2$ incubator. The following day, cells were seeded at a concentration of 100,000 cells per well in PBS and 0.5% BSA. Various doses of IL-2 and 100 nM of indicated anti-IL-2 antibodies were pre-complexed for 15-30 minutes at 37° C. before addition of 50 µl per well to the plate containing NK-92 cells. Cells were stimulated for 30 minutes at 37° C. followed by addition of 100 µl cold PBS to stop the reaction. The plate was centrifuged at 1500 rpm at 4° C. for 3 minutes. Subsequently, supernatant was removed and 80 µl cold MSD lysis buffer was added to each well. Cells were fully lysed by incubation on a shaking platform for 1 hour at 4° C. Total and phosphorylated STAT5a,b were measured using an MSD Phospho (Tyr694)/Total STAT5a,b Whole Cell Lysate kit (MesoScale Discovery; cat. K15163D-2) as per manufacturer's instructions. The plate was read on a Sector Imager 6000 (MesoScale Discovery). Curves were fit by nonlinear regression using the sigmoidal dose-response equation in Prism version 6.05 (GraphPad).

Figure 7C:
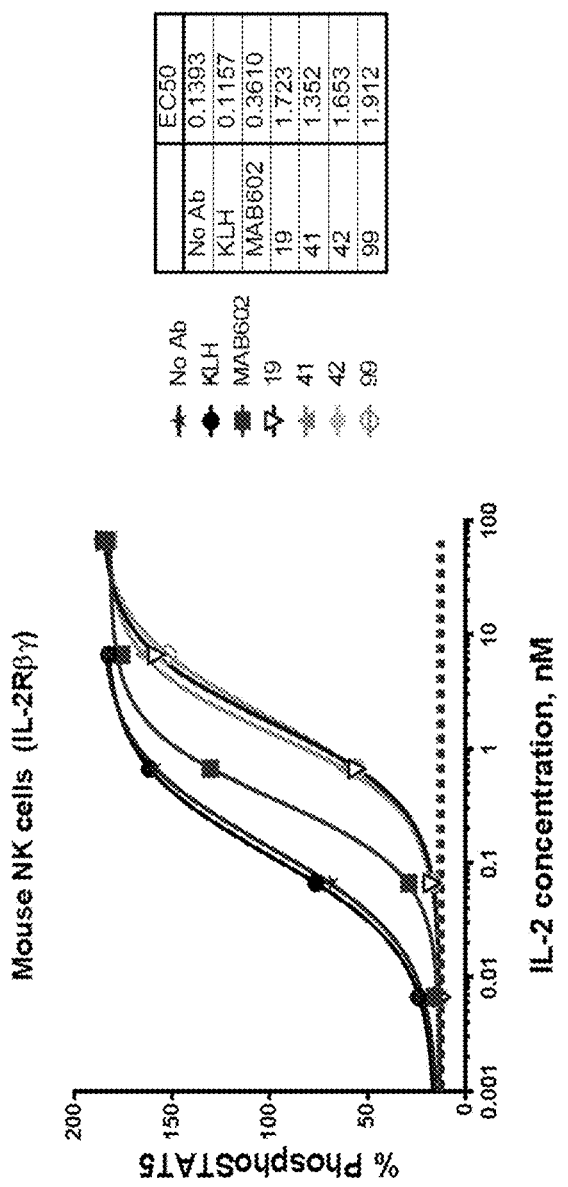

As expected, isotype control (anti-KLH) and no antibody controls were highly sensitive to IL-2 signaling, with an EC50 value of 0.9 and 0.6 pM, respectively (FIG. 7A). Relative to isotype controls, all compounds tested showed increased EC50 of IL-2-induced phosphorylation of STAT5a,b. Reference antibody MAB602 induced a 1,000 fold-shift in EC50 value relative to isotype control (from 0.9 pM to 900 pM). Fold shifts between XPA.92.019, XPA.92.041, XPA.92.042 were similar, with increased EC50 values of 900 pM, 1150 pM and 1700 pM, respectively. XPA.92.099 shifted the EC50 value slightly less in this assay, from 0.9 pM to 463 pM.

Phosphorylation of STAT5a,b in Human Primary NK Cells

In order to examine the ability of antibody/IL-2 complexes to modulate the STAT5 pathway on cells which have the dimeric receptor (IL-2 Rβγ), purified primary NK cells were utilized. An additional CD25+ depletion ensured only cells with the dimeric IL-2 R were present. Peripheral Blood Mononuclear Cells (PBMCs) from various donors were isolated using density gradient centrifugation. Briefly, diluted whole blood was layered above Ficoll (Sigma) solution in a 50 ml conical. The layers were centrifuged at room temperature for 30 minutes at 400 xg without the brake. The cell band was collected, washed, and frozen into aliquots. To isolate NK cells for PhosphoSTAT5 analysis, a vial of PBMCs was thawed and NK cells were isolated using the MACS NK cell isolation kit, human (Miltenyi Biotech; cat: 130-092-657) as per manufacturer's instructions. Purified NK cells were allowed to rest overnight in RPMI-1640 media (Life Technologies) with 10% FBS (Hyclone) but without IL-2 in a 37° C., 5% CO$_2$ incubator. The following day, CD25+NK cells were removed from the NK cell populations using magnetic bead separation. Briefly, cells were resuspended in MACS buffer (PBS (Life Technologies) and 1% bovine serum albumin (Sigma) and incubated with biotin anti-human CD25 (ebioscience) antibody (1 µl antibody for every 50 µl cell solution). After a 10 minute incubation at room temperature, cells were washed and resuspended in 40 µl MagniSort Streptavidin positive selection beads (ebioscience). After an additional incubation for 10 minutes at room temperature, the volume was brought to 2.5 mL and separation was done with an EasySep Magnet (STEMCELL Technologies) by incubating for 5 minutes at room temperature. Unbound cells were transferred to a clean tube and incubated for an additional 5 minutes at room temperature to ensure complete depletion of all CD25+ cells.

To complete the PhosphoSTAT5a,b assay, NK cells were seeded at a concentration of 100,000 cells per well in PBS and 0.5% BSA. Various doses of IL-2 and 100 nM of indicated anti-IL-2 antibodies were pre-complexed for 15-30 minutes at 37° C. before addition of 50 µl per well to the plate containing NK cells. Cells were stimulated for 30 minutes at 37° C. followed by addition of 100 µl cold PBS to stop the reaction. The plate was centrifuged at 1500 rpm at 4° C. for 3 minutes. Subsequently, supernatant was removed and 80 µl cold MSD lysis buffer was added to each well. Cells were fully lysed by incubation on a shaking platform for 1 hour at 4° C. Total and phosphorylated STAT5a,b were measured using an MSD Phospho (Tyr694)/Total STAT5a,b Whole Cell Lysate kit (MesoScale Discovery; cat. K15163D-2) as per manufacturer's instructions. Plate was read on a Sector Imager 6000 (MesoScale Discovery). Curves were fit by nonlinear regression using the sigmoidal dose-response equation in Prism version 6.05 (GraphPad).

Consistent with existing literature, the dimeric receptor was less sensitive to IL-2 cytokine, as seen by higher EC50 values in no antibody and Isotype control (anti-KLH) samples (133 and 127 pM, respectively) as compared to NK-92 cells (FIG. 7B). Relative to isotype controls, all compounds tested showed increased EC50 values of IL-2-induced phosphorylation of STAT5a,b. Reference antibody MAB602 induced a 10-fold shift in EC50 value relative to isotype control (from 128 pM to 1302 pM). Fold shifts of XPA.92.019, XPA.92.041, XPA.92.042 were similar, with EC50 values of 5041 pM, 4520 pM and 5124 pM, respectively. XPA.92.099 shifted the EC50 value slightly less than the other XPA.92 antibodies in this assay, with an EC50 value of 3054 pM. The fold shifts in EC50 for cells expressing human IL-2 receptors are summarized in Table 9.

TABLE 9 pSTAT5a, b Assays: $EC_{50}$ of mAb/IL-2 complex compared to $EC_{50}$ of unbound IL-2 (fold shift) in cells endogenously expressing human receptors.

| Antibody | NK92 (huRαβγ) (Fold $EC_{50}$ shift) | Human Primary NK cells (huRβγ) (Fold $EC_{50}$ shift) | Ratio of $EC_{50}$s (Rαβγ/Rβγ) |
|---|---|---|---|
| XPA.92.019 | 966 | 40 | 24 |
| XPA.92.041 | 1233 | 35 | 35 |
| XPA.92.042 | 1855 | 41 | 45 |
| XPA.92.099 | 495 | 24 | 21 |
| For comparison: MAB602 | 959 | 10 | 96 |

Phosphorylation of STAT5a,b in Mouse Primary NK Cells

NK cells in mice differ from their human counterparts in that they exclusively express the dimeric IL-2 receptor. In order to measure the ability of IL-2/antibody complexes to impact signaling in mice, spleens from 3 female BALB/C mice were obtained and a single cell suspension was generated by pushing organs through a 40 µM cell strainer (Falcon) using the back of a 1 mL syringe (Becton Dickinson). Splenocytes were washed then resuspended in RBC lysis buffer (Sigma) and allowed to incubate at room temperature for 5 minutes. Cells were then washed in RPMI-1640 (Life technologies) and 10% FBS (Hyclone). NK cells were sorted using the MACS mouse NK isolation kit II (Miltenyi) according to manufacturer instructions. Cells were washed, counted, and 100,000 cells were seeded in each well in PBS and 0.5% BSA buffer. Various doses of IL-2 and 100 nM of indicated anti-IL-2 antibodies were pre-complexed for 15-30 minutes at 37° C. before addition of 50 µl per well to the plate containing NK cells. Cells were stimulated for 30 minutes at 37° C. followed by addition of 100 µl cold PBS to stop the reaction. The plate was centrifuged at 1500 rpm at 4° C. for 3 minutes. Subsequently, supernatant was removed and cells were 80 µl cold MSD lysis buffer was added to each well. Cells were fully lysed by incubation on a shaking platform for 1 hour at 4° C. Total and phosphorylated STAT5a,b were measured using an MSD Phospho (Tyr694)/Total STAT5a,b Whole Cell Lysate kit (MesoScale Discovery; cat. K15163D-2) as per manufacturer's instructions. Plate was read on a Sector Imager 6000 (MesoScale Discovery). Curves were fit by nonlinear regression using the sigmoidal dose-response equation in Prism version 6.05 (GraphPad).

EC50 values for no antibody and isotype controls were very similar to those seen in human primary NK cells (FIG. 7C) (139 pM and 116 pM, respectively). Relative to isotype controls, all compounds tested showed increased EC50 values of IL-2-induced phosphorylation of STAT5a,b. Reference antibody MAB602 induced a 3-fold shift in EC50 value relative to isotype control (from 116 pM to 361 pM). Fold shifts of XPA.92.019, XPA.92.041, XPA.92.042 and XPA.92.099 were each about 10-15 fold, with EC50 values of 1723 pM, 1352 pM, 1663 pM and 1912, respectively. The fold shifts in EC50 for cells expressing mouse IL-2 receptors are summarized in Table 10.

TABLE 10 pSTAT5a, b Assays: $EC_{50}$ of mAb/IL-2 complex compared to $EC_{50}$ of unbound IL-2 (fold shift) in cells endogenously expressing murine receptors.

| Antibody | CTLL-2 (muRαβγ) (Fold $EC_{50}$ shift) | Mouse Primary NK cells (muβγ) (Fold $EC_{50}$ shift) | Ratio of $EC_{50}$s (Rαβγ/Rβγ) |
|---|---|---|---|
| XPA.92.019 | 523 | 15 | 35 |
| XPA.92.041 | 404 | 12 | 34 |
| XPA.92.042 | 793 | 14 | 57 |
| XPA.92.099 | 293 | 17 | 17 |
| For comparison: MAB602 | 227 | 3 | 76 |

Example 7: Analysis of Lymphocyte Subsets after In Vivo Administration of IL-2/Antibody Complexes Normal C57BL/6 mice were injected intraperitoneally with vehicle control or 1 µg hIL-2 (FIG. 8A-D), or 1.5 µg hIL-2 (FIGS. 8F and 8G) pre-incubated with a five-fold excess of either isotype control antibody or anti-IL-2 mAb as indicated on days 0, 2, and 4. On day 6, spleens were harvested using standard techniques and stained for flow cytometry subsets as follows. Spleens were isolated and dissociated to generate a single cell suspension. Red blood cells were lysed using RBC Lysis buffer (Gibco, Thermofisher). Cells were washed twice in FACS buffer (PBS and 2% FBS and sodium azide (0.1%) and plated in 96-well V-bottom plate ($1\times10^6$ cells/well). Cells were stained with a cocktail of the following fluorescently labeled antibodies in FACS buffer: CD4 (GK1.5), CD8 (53-6.7), CD25 (PC61.5), CD44 (IM7), CD122 (TM-(31), IFNγ (XMG1.2), and NK1.1 (PK136), Granzyme B (GB12) which were purchased from Biolegend, Ebioscience, BD Biosciences or Life Technologies). Samples were incubated in the staining cocktail for 20-60 minutes on ice, washed twice and read on a BD LSRII or BD Accuri. For the analysis of granzyme B staining, samples stained with surface markers and washed were fixed and permeabilized with cytofix/cytoperm buffer (BD Biosciences) per manufacturer's instructions and subsequently stained with anti-granzyme B antibody for 20-60 minutes on ice. Samples were washed twice and read on a BD LSRII or BD Accuri. Data was analyzed using FlowJo software (Treestar) or CFlow (BD Biosciences). For analysis of lymphocyte subsets, sorting was gated on lymphocytes, then lineage markers as follows: CD8+vs CD4 expression/% CD44hi of CD8+ cells; % CD25hi and CD44hi of CD4+ cells; and the percentage of cells positive for CD8, CD4, or NK1.1. FIGS. 8A-8D shows a summary of relevant T cell subsets, and FIG. 8E shows the ratios of CD8+/CD4+ T cells calculated from the data in FIGS. 8A and 8B. FIG. 8F shows frequency of NK1.1+ cells of total lymphocytes. FIG. 8G shows the production of Granzyme B by NK cells in mice after contact with the IL-2/anti-IL-2 antibodies.

These results show that the anti-IL-2 antibodies have an effect on the CD8/CD4 ratio in vivo as well as on NK cell levels and activity.

Example 8: Treatment with Antibody/IL-2 Complexes in Subcutaneous Lung Cancer Mouse Model Alone and in Combination with Checkpoint Inhibitors To demonstrate the effect of anti-IL-2 antibodies in tumor xenograft animal models, C57/BL6 mice were inoculated subcutaneously with Lewis lung carcinoma LLC-A9F1 (LLC) cells ($2.5 \times 10^5$ cells) and tumors were allowed to grow without treatment for 10 days to become established (treatment began on day 11). Outliers were removed before randomization for treatment. Treatment of six groups of mice bearing LLC tumors each were treated as follows: (1) vehicle only control, n=10 mice; (2) IL-2 complexed with anti-IL-2 XPA.92.099 monoclonal antibody (IL-2/mAb) (administered every 48 hours via IP injection, 1 µg IL-2 and 5 µg mAb), n=5 mice; (3) anti-PD-1 mAb alone (RMP1-14 clone, from Bioxcel, 200 µg given 2× per week), n=10 mice; (4) IL-2/mAb (XPA.92.099) and anti-PD-1 mAb combination, n=5 mice; (5) anti-CTLA-4 mAb alone (UC10-4F10-11, from Bioxcel, 200 µg given 2× per week), n=10 mice; or (6) IL-2/mAb (XPA.92.099) and anti-CTLA-4 mAb combination, n=5 mice. Tumor measurements (length and width) were performed blinded, and area was described in mm². FIG. 9 shows graphs of tumor area over time for individual mice treated as described above. While the numbers of mice treated were too low to achieve significance, the combined effect of IL-2/anti-IL-2 complex with either anti-PD-1 or anti-CTLA-4 have the potential to reduce tumor growth and induce complete responses to a greater extent than controls or single agent treatments (FIG. 9).

Figures 10A, 10B:
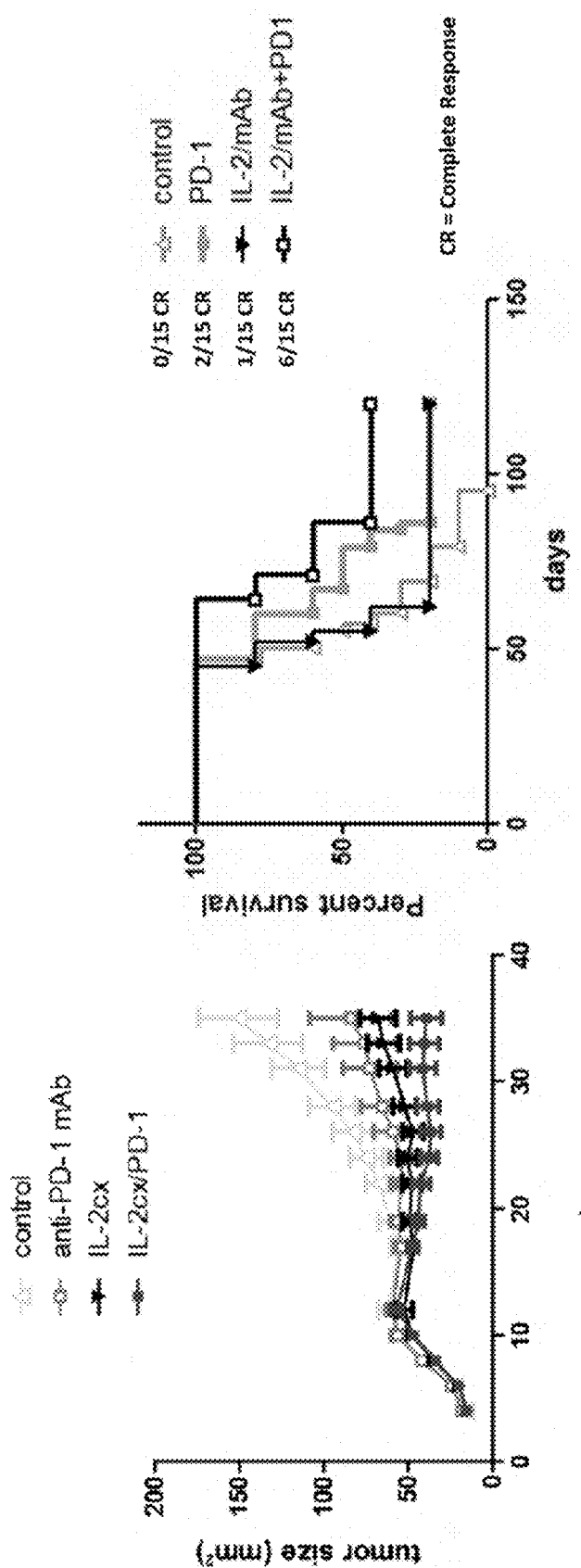
FIGS. 10A-10B show the mean tumor size (FIG. 10A) and later percentage survival (FIG. 10B) of subcutaneous LLC xenograft mice treated with IL-2/anti-IL-2 antibody complex (IL-2cx) and anti-PD-1 antibody mono- and combination therapy. Error bars represent +/−standard error of the mean (SEM), n=15 mice per arm.

To further evaluate the anti-tumor effect of anti-IL-2 antibodies, an experiment with greater numbers of mice (n=15/group) was carried out. Mice were inoculated with LLC tumor cells as described above. Once tumors were established and the mice were randomized, four groups of 15 mice each were treated as follows: (1) vehicle only control (PBS); (2) anti-PD-1 mAb (RMP1-14 clone) given 2× per week, 200 µg subcutaneously (sc); (3) IL-2/mAb complexes (clone 99, every 48 hours, IP injection, 2 µg IL-2+10 µg mAb); (4) combination of IL-2/mAb99+anti-PD-1 mAb as described in groups (2) and (3). Tumors measurements (length and width) were performed blinded, and area was described in mm². FIG. 10A shows a graph of average tumor volume over time for each treatment group as described above. Error bars represent standard error of the mean (SEM). While IL-2/anti-IL-2 complex and anti-PD-1 monotherapies significantly reduced tumor growth compared to control-treated mice, the combined effect of IL-2/anti-IL-2 complex with either anti-PD-1 was significantly greater than that of either reagent alone. FIG. 10B shows a survival plot from the same experiment. No mice in the control group had a complete response (no tumor detectable), while such a complete response was achieved by one mouse in the IL-2/mAb99 alone group, two in the anti-PD-1 alone group, and 6 in the combination treatment group.

Figure 11B:
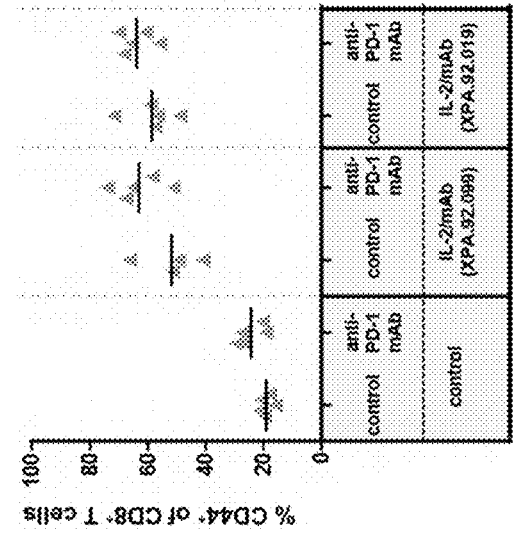
FIGS. 11A-11F show graphical representations of the percentage of T cell subsets (Percentage of CD8+, FIG. 11A; CD44+ of CD8+, FIG. 11B; CD4+, FIG. 11C; CD25+ of CD4+, FIG. 11D; IFNγ+ of CD8+, FIG. 11E; the ratio of CD8+/CD4+, FIG. 11F) from a subcutaneous LLC xenograft mouse model treated with IL-2/anti-IL-2 antibody complexes (using XPA.92.019 or XPA.92.099 IL-2 antibodies) alone or combined with an anti-PD-1 antibody.
Figure 11A:
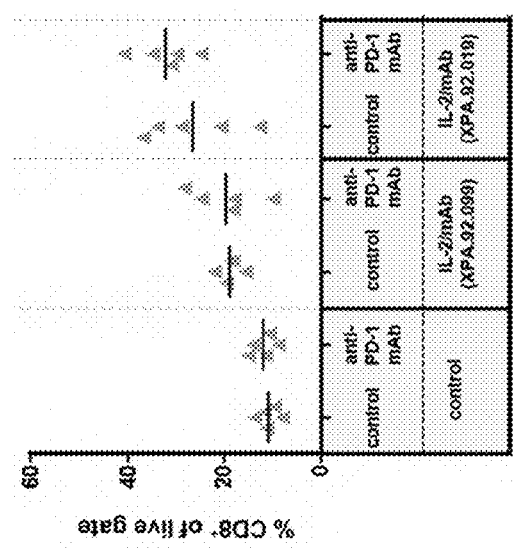
Figure 11C:
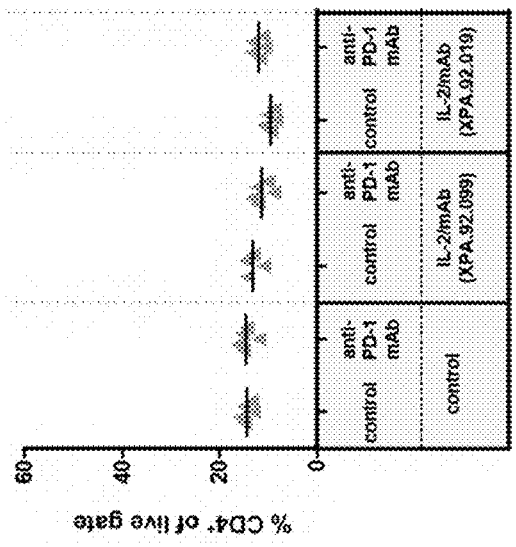
Figure 11E:
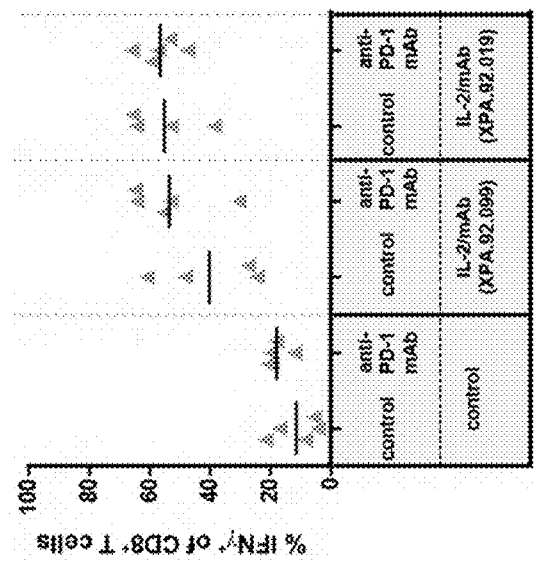
Figure 11D:
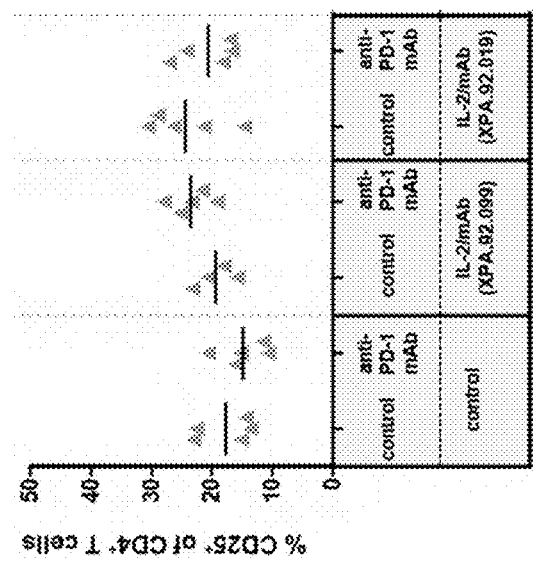
Figure 11F:
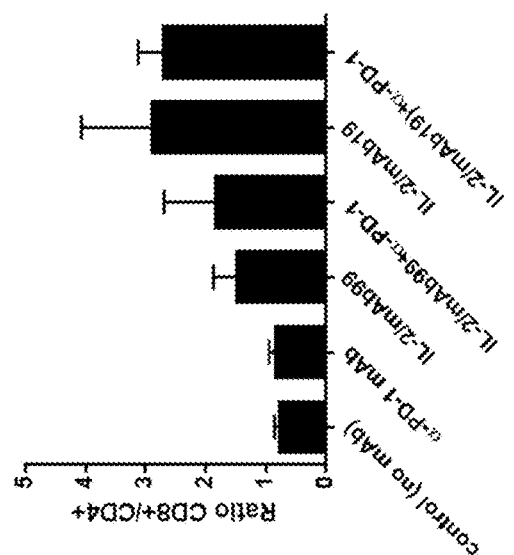

Example 9: The Effect of IL-2/Antibody Complexes on Immune Cells in C57BL/6Mice Bearing Subcutaneous LLC Tumors To evaluate the effects of antibody/IL-2 complexes on immune cells in vivo during tumor challenge, mice were injected with $1 \times 10^6$ LLC tumors as described above. Twenty-one days after tumor injection, mice with established tumors were randomized into groups of 5 and treated as follows: (1) control (no Ab or IL-2); (2) anti-PD-1 mAb (RMP1-14 clone), 200 µg given subcutaneously twice per week; (3) IL-2/mAb99 complexes (2 µg IL-2+10 µg mAb), by IP injection every 2 days; (4) combination of IL-2/mAb99+anti-PD-1 mAb as described in groups (2) and (3); (5) IL-2/mAb19 complexes (2 µg IL-2+10 µg mAb, by IP injection on days 1, 3, 5, 9, 13, and 17); (6) combination of IL-2/mAb19+anti-PD-1 mAb as described in groups (2) and (5). On day 19 after the initiation of treatment the mice were sacrificed and the immune cells were analyzed as follows. Splenocytes were isolated and analyzed as described above for expression of cell surface markers. To assay the ability of CD8+ T cells to produce interferon gamma (IFNγ), splenocytes were stimulated with PMA (Phorbol 12-Myristate 13-Acetate, 50 ng/mL) and ionomycin (1 µM) for 10-12 hours in (RPMI and 10% FBS) and brefledin A (Goglistop, BD Biosciences). Cells were then stained for extracellular CD8, fixed and permeabilized (Cytofix/Cytoperm, BDBiosciences), then stained intracellularly for IFNγ. Samples were read on BD LSRII or BD Accuri analyzed using FlowJo software (Treestar) or CFlow (BD Biosciences). For analysis of CD8+ T cell responses, cells were gated on lymphocytes and CD8+ T cells, and the percentage of cells positive for IFNγ were assessed. The graphs in FIG. 11 show that treatment with IL-2/mAb complexes led to an increase in the frequency of CD8+ T cells (FIG. 11A), and in the proportion of CD8+ T cells that are activated (% CD44hi, FIG. 11B), while no increase was seen in the frequency of CD4+ T cells (FIG. 11C) or percent of CD4+ cells that are CD25hi ($T_{regs}$) (% CD25hi, FIG. 11D). FIG. 11 further shows that the IL-2/mAb treatment led to an increase in the frequencies of CD8+ T cells that were able to produce IFNγ upon stimulation with PMA/I (FIG. 11E), as well as in the ratio of CD8+/CD4+ T cells (FIG. 11F).

Example 10: The Effect of IL-2/Antibody Complexes on Human Immune Cells

In addition to T and NK cells, other immune and non-immune cell types express functional IL-2 receptors. These include B cells, monocytes, granulocytes and, in some reports, endothelial cells. Many of these cell types express IL-2Rα constitutively or can express it in response to certain cytokines or stimulatory factors. Experiments were performed to examine how treatment with IL-2/mAb complexes impacts activation in cells expressing trimeric IL-2 receptors (IL-2Rαβγ). PBMCs contain significant percentages of various immune cell subsets and thus provide a useful tool to assess the impact of anti-IL-2 antibodies on key cell populations. Cells that are reported to express functional trimeric IL-2Rαβγ include: CD56$^{bright}$ NK cells, activated CD8 T cells, T$_{regs}$, monocytes and B cells. As a read-out of activation, expression levels of the CD69 marker, which is induced by IL-2 signaling in T and NK cells, was analyzed. In addition, frequency of T$_{regs}$ in the CD4 T cell population after IL-2/mAb complex treatment was determined.

PBMCs from various donors were isolated using density gradient centrifugation. Diluted whole blood was layered above Ficoll (Sigma) solution in a 50 mL conical tube. The layers were centrifuged at room temperature for 30 minutes at 400×g without the brake. The cell band was collected, washed, and frozen into aliquots. Aliquots were thawed into complete RPMI medium (RPMI 1640 (Life Technologies)+ 10% FBS (Hyclone)+2 mM L-glutamine). After two washes, cells were counted and plated at 1×10$^6$ PBMC/well in 96-well round bottom plate in 50 µl volume. Various doses of recombinant human IL-2 (Reprokine, Israel) and 200 nM of indicated anti-IL-2 antibodies were pre-complexed for 30 minutes at 37° C. before addition of 50 µl per well to the plate containing cells. Plates were subsequently incubated for 20-24 hours at 37° C. Once the incubation was complete, supernatants were removed and cells were washed twice in FACS buffer (PBS (Life Technologies), 0.5% BSA (Sigma) and 0.1% sodium azide (Teknova)). Samples were Fc-blocked with human TruStain FcX for 10 minutes at room temperature (BioLegend) and divided into two wells each. One set was stained with the following cocktail of fluorescently labeled antibodies (Biolegend): CD69 (FN50), CD4 (OKT4), CD8a (SK1), CD127 (A019D5), CD25 (M-A251), CD3 (HIT3a). The second set was stained with the following cocktail of fluorescently labeled antibodies (Biolegend): CD3 (HIT3a), CD56 (HCD56), CD19 (HIB19), CD69 (FN50), CD14 (M5E2). Samples were incubated at 4° C. for 60 minutes in the dark. They were washed twice with FACS buffer and fixed with 50 µl BD Cytofix (Becton Dickenson) for 20 minutes at 4° C. in the dark. Samples were washed twice with FACS buffer, and read on a BD FACSCanto II. Data were analyzed with FlowJo Software (Treestar) and GraphPad Prism (version 7) using a 3-parameter fit.

NK cells were identified by gating on lymphocytes followed by CD3- and CD56+ populations. Of this CD56+ population, the brightest ~10% represent the CD56$^{bright}$ NK cells. In CD56$^{bright}$ NK cells, a dose-dependent effect of IL-2 treatment on CD69 expression was observed with an EC50 value of 7.6 nM (FIG. 13A) or 9.5 nM (FIG. 13B) for donors 603 or 625, respectively. The reference antibody MAB602 induced a 5-10 fold right-shift in EC50 value (FIG. 13C). Treatment with XPA.92.019, XPA.92.042 or XPA.92.099 also showed a similar increase in the EC50 value as was seen with MAB602 (FIG. 13C). This suggests that these anti-IL-2 antibodies decrease sensitivity to IL-2-induced activation on CD56$^{bright}$ NK cells expressing IL-2Rαβγ.

In order to analyze induction of CD69 in the T$_{reg}$ population, lymphocytes that expressed the following profile were analyzed: CD3+CD4+CD25+CD127-. As with the CD56$^{bright}$ NK cells, a dose-dependent effect of IL-2 treatment was observed with an EC50 value of 28 nM (FIG. 14A) or 22 nM (FIG. 14B) for donors 603 or 625, respectively. The reference antibody, MAB602, induced a 5-10 fold right-shift in EC50 value (FIG. 14C). Treatment with XPA.92.042 or XPA.92.099 also showed a similar increase in EC50 value to MAB602, while XPA.92.019 induced a higher shift of 10-15 fold (FIG. 14C).

Figure 15A:
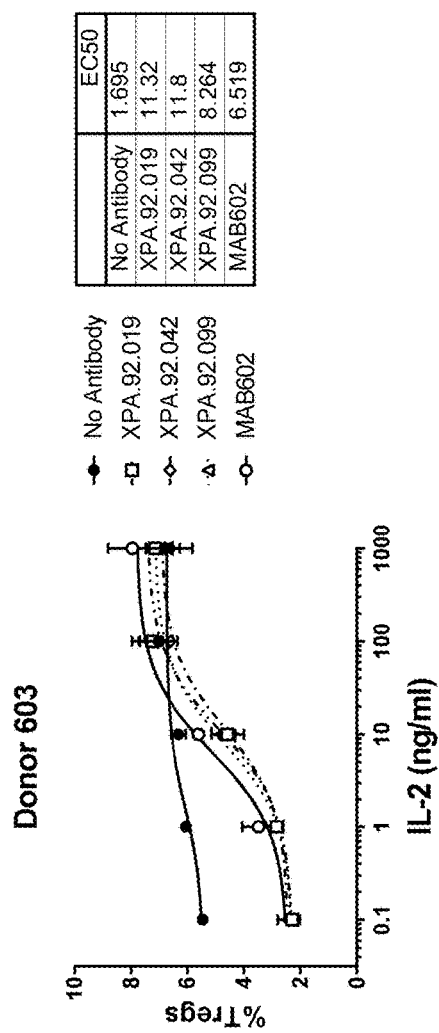
FIGS. 15A and 15B show the $T_{reg}$ homeostasis for human PBMCs treated with various doses of IL-2 pre-complexed with a fixed 200 nM concentration of indicated antibodies for 24 hours. Samples were stained for $T_{reg}$ markers and analyzed by flow cytometry gated on lymphocytes/CD3+/CD4+/CD25+CD127-. Frequencies of $T_{regs}$ of total CD4+ population are shown for donor 603 (FIG. 15A) and donor 625 (FIG. 15B).
Figure 15B:
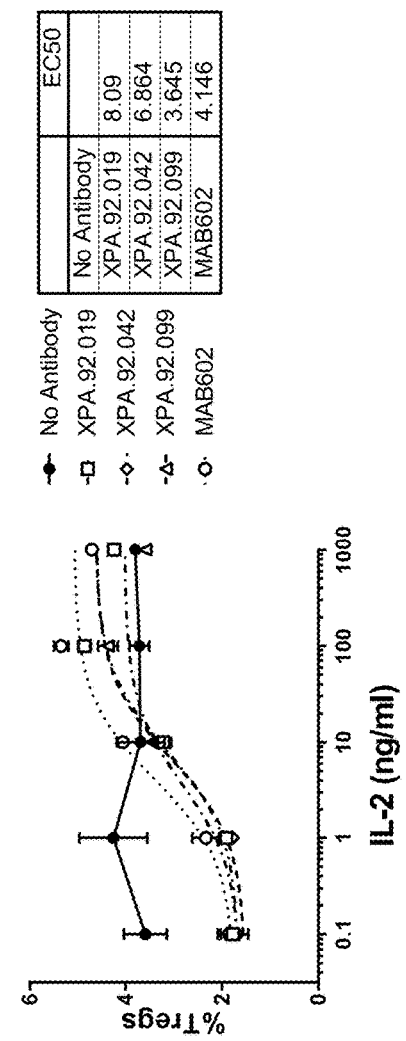

Signaling provided by IL-2 is important for Treg growth and homeostasis. As shown in FIG. 15A and FIG. 15B, for the concentrations of IL-2 used in this assay, the percentages of T$_{regs}$ remained relatively unchanged for the no antibody controls. However, the addition of pre-complexed IL-2/anti-IL-2 antibodies decreased the frequency of T$_{regs}$ in a dose-dependent manner for donors 603 (FIG. 15A) and 625 (FIG. 15B). At high concentrations of IL-2, the frequency of Treg cells was similar or slightly higher than samples without antibody treatment. However, at IL-2 concentrations below 10 ng/mL, significantly fewer T$_{regs}$ were identified after 24 hours of stimulation with all antibodies tested. This suggests that XPA.92.019, XPA.92.042 and XPA.92.099 antibodies inhibit the IL-2 signal required for T$_{reg}$ homeostasis.

Example 11: The Effect of IL-2/Antibody Complexes on Immune Cells in a Murine Colon Carcinoma Model In order to determine if the anti-IL-2 antibody/IL-2 complex was effective in treating colon carcinoma, mice were subcutaneously implanted with CT26 cells and subsequently administered antibody/IL-2 treatment.

Tumor cells. CT26 murine colon tumor cells were originally purchased from ATCC. The tumor cells were thawed from one frozen vial and placed in in vitro culture using the appropriate completed RPMI culture medium with 10% heat-inactivated FBS.

Animals. Female Balb/c mice of 7-8 weeks of age purchased from Jackson Laboratories were used. The mice were acclimated for 4 days and housed at an animal facility as four mice in each of 18 cages with food and water provided ad libitum, and acclimated for 4 days prior to initiation of the study. The mice were weighed prior to implant of tumor cells (Day 0), once a week until tumors were measurable by calipers, the day prior to treatment initiation, and twice a week during tumor growth and treatment.

Treatments. IL-2 was obtained from Reprokine (Israel) and anti-IL-2 antibody was prepared at XOMA. The stock solution of IL-2 made in sterile water was diluted appropriately to the dosing solutions to deliver 50 µg, 100 µg, 150 µg, and 1.5 µg in the volume of 200 µl to each mouse of the corresponding groups. IL-2 and antibody combinations were formulated together in the dosing solution the day of administration.

In vivo efficacy studies: The CT26 cell cultures were expanded for about one week until a sufficient number of cells were ready to be implanted in mice. The day of implant, the cells were harvested from cultures at the exponential phase growth after a brief treatment with warm trypsin/EDTA solution followed by addition of serum-containing medium and two washes in sterile, 1×PBS. The cell suspension was kept on ice until and during the time of implant to preserve cell viability and ability to adhere. After the last centrifugation, the cells were counted and resuspended appropriately to the final concentration of 7.5×10$^6$/ml in sterile, 1×PBS. The viability was determined by using a 0.4% trypan blue solution and was found to be 94.5%. The tumor cells (0.75×10$^6$) were implanted subcutaneously in the left flank of anesthetized mice in a volume of 100 ul. The mice were carefully monitored and the clinical observations were recorded daily. The mice were weighed daily after treatment administration and tumor growth was determined twice a week by caliper measurement of length (L) and width (W); the tumor size is calculated with the formula (L×W$^2$)/2). The tumors became caliperable 6 days after implant of cells and reached the size of ~100 mm$^3$ when they were randomized into treatment groups using a computer-generated randomization template that ensure similar tumor average and standard deviation between the groups. After the randomization, the mice received test articles by the intraperitoneal route.

Figure 16:
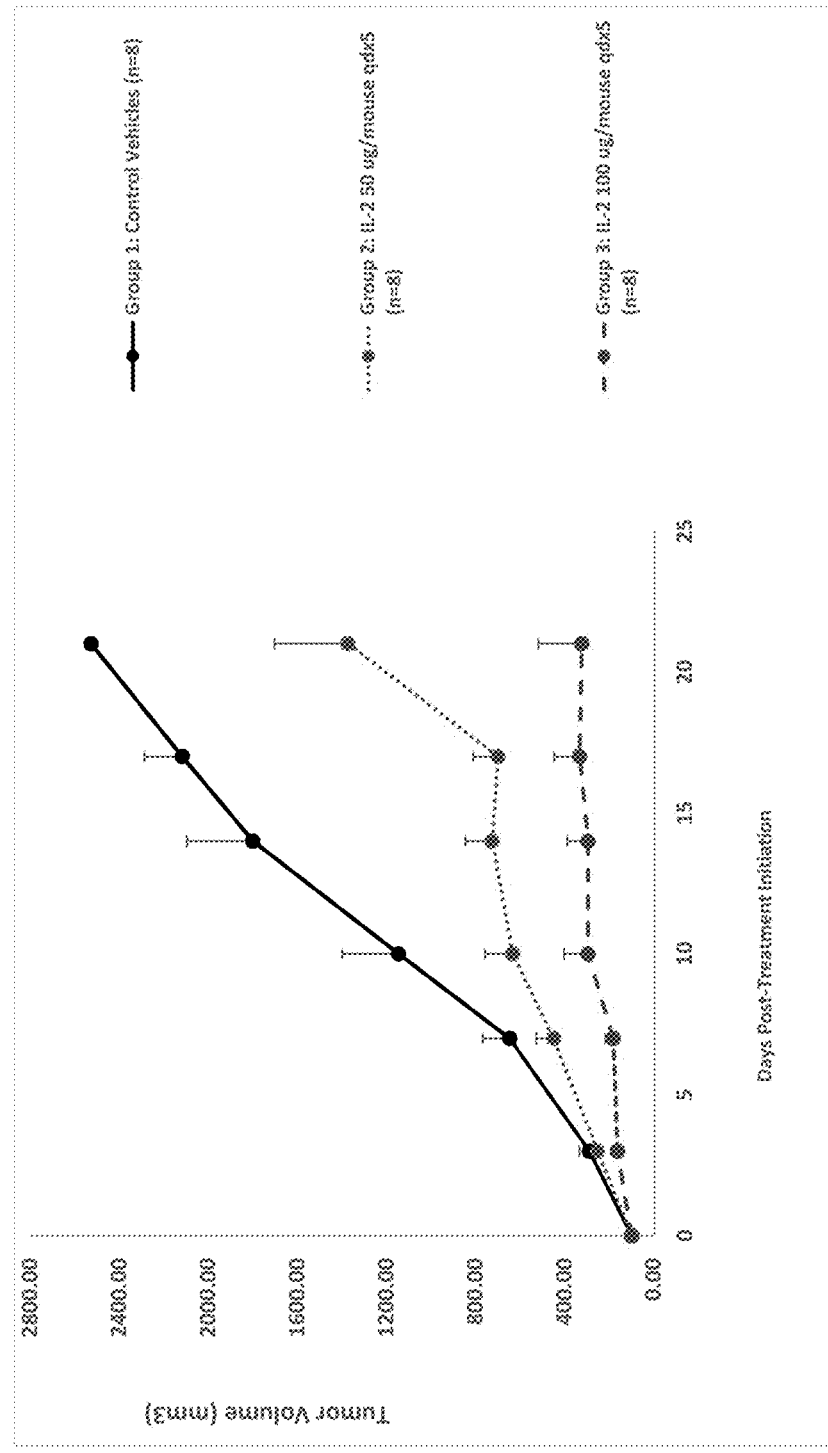
FIG. 16 illustrates results of analysis of the tumor growth outcomes in animals receiving CT26 colon carcinoma cells and treated with IL-2 alone.

Results: An analysis of the tumor growth outcomes in animals treated with just IL-2 shows that while there was a decrease in tumor growth from days 10-20 in the IL-2 50 μg and 100 μg treated groups (approx.1300 m$^3$ and 400 m$^3$ at day 20, respectively) compared to vehicle control (approx. 2600 m$^3$ at day 20)), these mice were lethargic and there was some mortality (3) in the animals (FIG. 16). This is consistent with preclinical reports in the literature and with the challenging nature of effective IL-2 therapy in the clinic. Doses of IL-2 alone below 2.5 mg/kg have minimal anti-tumor efficacy.

In contrast, administration of IL-2 in combination with anti-IL-2 antibody in a ratio of 1:1 showed improved Therapeutic Index (TI) of IL-2:mAb combination compared to vehicle control, and the importance of a 1:1 molar ratio (1:10 mass ratio) and anti-tumor efficacy of a very low dose IL-2 in the presence of IL-2 mAb. Mice were administered various doses of IL-2 and antibody as set out in Table 11.

TABLE 11

| Design | Number of Mice | Treatment/ IP route | Dose (ug/mouse)/ Volume | Dosing Schedule |
|---|---|---|---|---|
| Therapeutic Treatment initiation post-randomization of tumors (~100 mm$^3$) | 6 | Control vehicles | NA/200 ul | Q3 days 1.5 wk |
| | 6 | mAb19 + IL-2 (1:1 molar ratio) | 15 ug/mouse + 1.5 ug/mouse | Q3 days 1.5 wk |
| | 6 | mAb19 + IL-2 (1:2 molar ratio) | 15 ug/mouse + 3.0 ug/mouse | Q3 days 1.5 wk |
| | 6 | mAb19 + IL-2 (3:1 molar ratio) | 15 ug/mouse + 0.5 ug/mouse | Q3 days 1.5 wk |
| | 6 | mAb19 + IL-2 (1:2 molar ratio; ½ total dose vs group 3 above) | 7.5 ug/mouse + 1.5 ug/mouse | Q3 days 1.5 wk |

Figure 17:
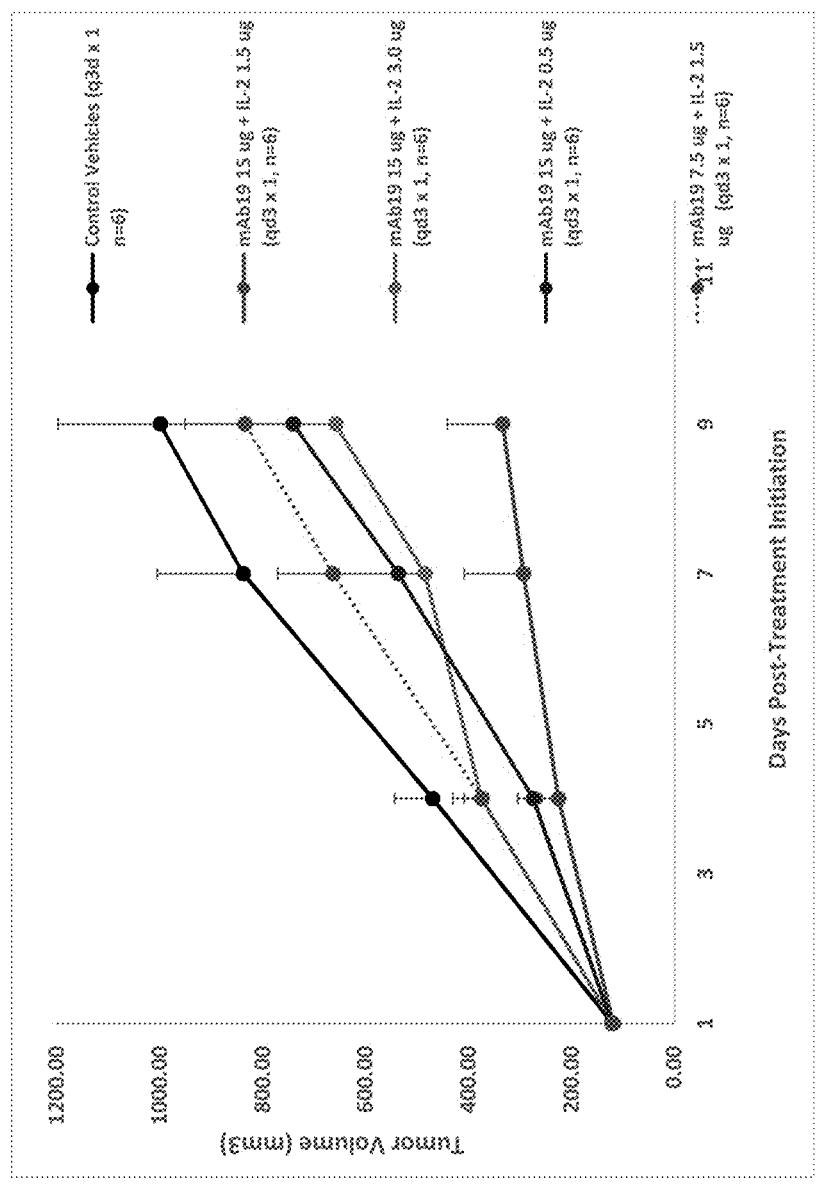
FIG. 17 shows tumor growth outcomes in animals receiving CT26 colon carcinoma and different molar ratios of IL2:mAb IL2, demonstrating that animals receiving a 1:1 ratio of antibody to IL-2 had improved efficacy against tumor growth compared to animals receiving other ratios of IL-2/antibody combination treatment.

FIG. 17 demonstrates that animals receiving a 1:1 ratio of antibody to IL-2 had improved efficacy against tumor growth compared to animals receiving other ratios of IL-2/antibody combination treatment. Additionally, there was no lethality and no clearly adverse weight loss nor adverse behavioral signs in these animals.

These results show that very low doses of IL-2 in combination with anti-IL2 mAb demonstrates moderate to good anti-tumor efficacy and a 1:1 molar ratio of mAb19:IL2, dosed as 15 ug:1.5 ug (i.e. 0.75 mg/kg:0.075 mg/kg) is the most efficacious ratio. Note that the mAb:IL2 15 ug:1.5 ug group at Day 9 is statistically significantly different from all other groups.

An additional study was carried out to further analyze the molar ratio aspect of the IL-2/anti-IL-2 antibody treatment. The treatment regimens are shown below in Table 12.

TABLE 12

| Design | Number of Mice | Treatment/ IP route | Dose (ug/mouse)/ Volume | Dosing Schedule |
|---|---|---|---|---|
| Therapeutic Treatment initiation post-randomization of tumors (~100 mm$^3$) | 11-12 | Control vehicles | NA/200 ul | Q3 days 1.5 wk (i.e. Days 1, 4, 7, 10) |
| | 11-12 | mAb19 + IL-2 (1:1 molar ratio) | 15 ug/mouse + 1.5 ug/mouse | Q3 days 1.5 wk |
| | 11-12 | mAb19 + IL-2 (2:1 molar ratio) | 30 ug/mouse + 1.5 ug/mouse | Q3 days 1.5 wk |

Figure 18:
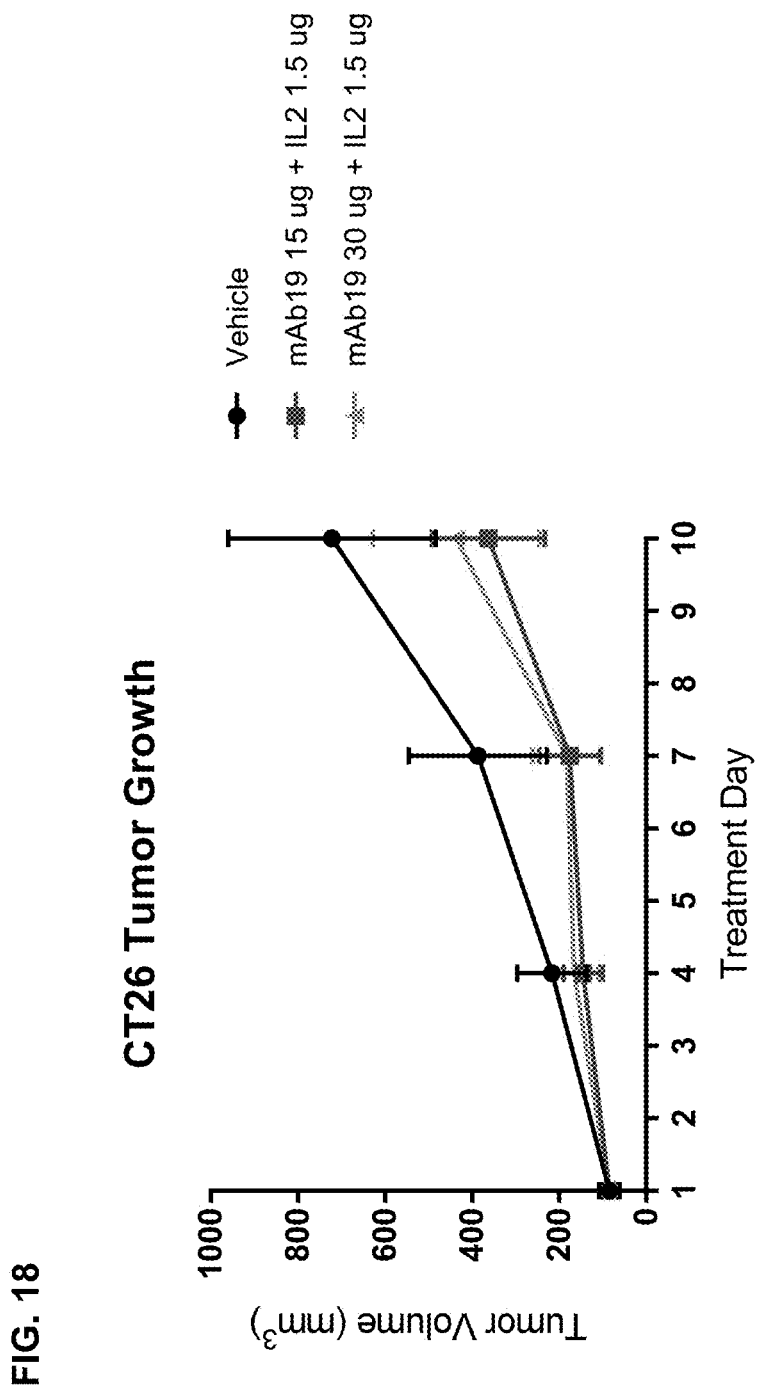
FIG. 18 shows slower tumor growth of a colon cell line in animals treated with a 1:1 or 2:1 molar ratio of the mAb:IL2 complex.

Results are shown in FIG. 18, and illustrate that the slower tumor growth in the mAb:IL2 15 μg:1.5 μg group at Days 7 and 10 is statistically significantly different from the vehicle control group, and that growth in the mAb:IL2 30 μg:1.5 μg group was also lower compared to controls. The experiments demonstrate that very low doses of IL-2 in combination with anti-IL2 mAb demonstrates anti-tumor efficacy and a 1:1 molar ratio of mAb:IL2, dosed as 15 ug:1.5 ug (i.e. 0.75 mg/kg:0.075 mg/kg), is at least as efficacious as the 2:1 ratio. There was no lethality or noticeable adverse events in any of these dose groups. Hence, a therapeutic index of at least 6-fold (15:0.5 to 15:3.0) is indicated in these studies whereas comparable efficacy with IL-2 alone is accompanied by some level of mortality.

Numerous modifications and variations in the invention as set forth in the above illustrative examples are expected to occur to those skilled in the art. Consequently only such limitations as appear in the appended claims should be placed on the invention.

What is claimed:

1. A method for treating a disease, condition or disorder associated with increased interleukin-2 (IL-2) or interleukin-2 receptor (IL-2 R) levels or activity comprising the step of administering to a subject in need thereof a therapeutically effective amount of a human or humanized antibody that binds human interleukin-2 (IL-2) with an affinity $K_D$ of $1\times10^{-10}$ M or less and inhibits binding of IL-2 with an IL-2 receptor alpha (IL-2 Rα) subunit,
wherein the antibody inhibits IL-2 signaling through IL-2 Rαβγ and through IL-2 Rβγ, and
wherein the antibody inhibits IL-2 signaling through IL-2 Rαβγ to a greater extent than through IL-2 Rβγ,
wherein the disease, condition or disorder is cancer, and
wherein the antibody is administered in combination with IL-2 or an IL-2 variant.

2. The method of claim 1, wherein the cancer is selected from the group consisting of melanoma, renal cell carcinoma, lymphoma, sarcoma, breast cancer, lung cancer, bladder cancer, colon cancer, gastric cancer, non small cell lung carcinoma (NSCLC), head and neck cancer, skin cancer, and squamous cell carcinoma (SCC).

3. The method of claim 2, wherein the administration reduces tumor volume in the subject.

4. The method of claim 1 wherein the administration increases the ratio of CD8+T cells to CD4+T cells in the subject.

5. The method of claim 1 wherein the antibody is administered intravenously, intratumorally, intraarterially, intraperitoneally, intramuscularly, intradermally or subcutaneously.

6. The method of claim 1, wherein the antibody is administered in combination with an additional therapeutic agent, optionally wherein the therapeutic agent is a checkpoint inhibitor, a chimeric antigen receptor T-cells/tumor-infiltrating lymphocytes (CART/TIL) agent, an antibody to a tumor antigen or a vaccine.

7. The method of claim 1, wherein the antibody is administered once per week, once every 2 weeks, twice per month, once monthly, once every two months, or once every three months.

8. The method of claim 1 wherein the antibody comprises
i)
(a) a heavy chain CDR1 amino acid sequence set forth in SEQ ID NOs: 17, 20, 23, or 26;
(b) a heavy chain CDR2 amino acid sequence set forth in SEQ ID NOs: 18, 21, 24, or 27 that is from the same heavy chain variable region as (a); and
(c) a heavy chain CDR3 amino acid sequence set forth SEQ ID NOs: 19, 22, 25, or 28 that is from the same heavy chain variable region as (a); and,
ii)
(a) a light chain CDR1 amino acid sequence set forth in SEQ ID NOs: 29, 32, 35, or 38;
(b) a light chain CDR2 amino acid sequence set forth in SEQ ID NOs: 30, 33, 36, or 39 that is from the same light chain variable region as (a); and
(c) a light chain CDR3 amino acid sequence set forth in SEQ ID NOs: 31, 34, 37, or 40 that is from the same light chain variable region as (a).

9. The method of claim 8, wherein the antibody comprises
an amino acid sequence at least 90% identical to a heavy chain variable region amino acid sequence set forth in SEQ ID NOs: 1, 3, 5, or 7, and/or
an amino acid sequence at least 90% identical to a light chain variable region amino acid sequence set forth in any one of SEQ ID NOs: 9, 11, 13, or 15.

10. The method of claim 1, further comprising a heavy chain constant region, wherein the heavy chain constant region is a modified or unmodified IgG, IgM, IgA, IgD, IgE, a fragment thereof, or combinations thereof.

11. The method of claim 1, in which one or more light chain framework amino acids have been replaced with corresponding amino acid(s) from another human antibody amino acid sequence.

12. The method of claim 1, wherein the antibody comprises
   (a) heavy chain HCDR1-HCDR3 amino acid sequences set forth in SEQ ID NOs: 17-19; and
   (b) light chain LCDR1-LCDR3 amino acid sequences set forth in SEQ ID NOs: 29-31.

13. The method of claim 1, wherein the antibody comprises a heavy chain variable region amino acid sequence set forth in SEQ ID NO: 1 and a light chain variable region amino acid sequence set forth in SEQ ID NO: 9.

14. A method for suppressing IL-2 activity in a cell in vitro comprising the step of contacting the cell with an amount of an antibody that binds human interleukin-2 (IL-2) effective to suppress IL-2 activity in the cell, wherein the antibody is a human or humanized antibody that binds human interleukin-2 (IL-2) with an affinity $K_D$ of $1\times10^{-10}$ M or less and inhibits binding of IL-2 with an IL-2 receptor alpha (IL-2 Rα) subunit,
   wherein the antibody inhibits IL-2 signaling through IL-2 Rαβγ and through IL-2 Rβγ, and
   wherein the antibody inhibits IL-2 signaling through IL-2 Rαβγ to a greater extent than through IL-2 Rβγ.

* * * * *

SEQUENCE LISTING

```
<160> NUMBER OF SEQ ID NOS: 54

<210> SEQ ID NO 1
<211> LENGTH: 119
<212> TYPE: PRT
<213> ORGANISM: Homo sapiens
<220> FEATURE:
<221> NAME/KEY: MISC_FEATURE
<223> OTHER INFORMATION: XPA.92.019 HV
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
```

```
<221> NAME/KEY: MISC_FEATURE
<222> LOCATION: (97)..(108)
<223> OTHER INFORMATION: H-CDR3

<400> SEQUENCE: 1

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Tyr Tyr
            20                  25                  30

Gly Met His Trp Val Arg Gln Ala Pro Gly Lys Gly Leu Glu Trp Val
        35                  40                  45

Ala Asp Ile Ser Asn Asp Gly Ser Asn Lys Tyr Tyr Ala Asp Ser Val
    50                  55                  60

Lys Gly Arg Phe Thr Ile Ser Arg Asp Asn Ser Lys Thr Thr Leu Tyr
65                  70                  75                  80

Leu Gln Met Asn Ser Leu Arg Pro Glu Asp Thr Ala Val Tyr Tyr Cys
                85                  90                  95

Ala Thr Pro Tyr Tyr Asp Ser Ser Gly Leu Asp Tyr Trp Gly Gln Gly
            100                 105                 110

Thr Leu Val Thr Val Ser Ser
        115

<210> SEQ ID NO 2
<211> LENGTH: 357
<212> TYPE: DNA
<213> ORGANISM: Homo sapiens
<220> FEATURE:
<221> NAME/KEY: misc_feature
<223> OTHER INFORMATION: XPA.92.019 HV

<400> SEQUENCE: 2
gaagtgcagc tggtggagtc tgggggaggc ttggtccagc ctggagggtc cctgagactc      60
tcctgtgcag cctctggatt caccttcagt tactatggca tgcactgggt ccgccaggct     120
ccaggcaagg ggctagagtg ggtggcagat atatcaaatg atggaagtaa taaatattac     180
gcagactctg tgaagggccg attcaccatc tccagagaca attccaagac cacgctgtat     240
ctgcaaatga acagcctgag acctgaggac acggctgtat attactgtgc gacccccttac    300 tatgatagta gtgggttgga ctactggggc cagggaaccc tggtcaccgt ctcctca       357

<210> SEQ ID NO 3
<211> LENGTH: 117
<212> TYPE: PRT
<213> ORGANISM: Homo sapiens
<220> FEATURE:
<221> NAME/KEY: MISC_FEATURE
<223> OTHER INFORMATION: XPA.92.041 HV
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(106)
<223> OTHER INFORMATION: H-CDR3

<400> SEQUENCE: 3

Glu Val Gln Leu Val Gln Ser Gly Ala Glu Val Lys Lys Pro Gly Glu
1               5                   10                  15
```

Ser Leu Lys Ile Ser Cys Lys Gly Ser Gly Tyr Asn Phe Asp Thr Tyr
            20                  25                  30

Trp Ile Gly Trp Val Arg Gln Met Pro Gly Arg Gly Leu Glu Trp Met
        35                  40                  45

Gly Thr Ile Tyr Pro Ala Asp Ser Asp Thr Arg Tyr Ser Pro Ser Phe
    50                  55                  60

Gln Gly Gln Val Thr Thr Ser Ala Asp Lys Ser Ile Ser Thr Ala Tyr
65                  70                  75                  80

Leu Gln Trp Gly Ser Leu Arg Ala Ser Asp Thr Ala Met Tyr Tyr Cys
                85                  90                  95

Ala Arg Phe Ser Ser Ser Ala Tyr Asp Ile Trp Gly Gln Gly Thr Met
            100                 105                 110

Val Thr Val Ser Ser
        115

<210> SEQ ID NO 4
<211> LENGTH: 351
<212> TYPE: DNA
<213> ORGANISM: Homo sapiens
<220> FEATURE:
<221> NAME/KEY: misc_feature
<223> OTHER INFORMATION: XPA.92.041 HV

<400> SEQUENCE: 4
gaggtccagc tggtacagtc tggagcagag gtgaaaaagc ccggggagtc tctgaagatt      60
tcctgtaagg gttctggata caactttgac acgtactgga tcggctgggt gcgccagatg     120 cccggggagag gcctggagtg gatgggcacc atctatcctg ctgactctga caccagatat   180
agcccgtcct tccaaggcca ggtcaccacc tcagccgaca gtccatcag caccgcctac      240 ctgcagtggg gcagcctgag ggcctcggac accgccatgt attactgtgc gaggtttagc    300
agttctgcct atgacatttg gggccaaggg acaatggtca ccgtctcttc a            351

<210> SEQ ID NO 5
<211> LENGTH: 117
<212> TYPE: PRT
<213> ORGANISM: Homo sapiens
<220> FEATURE:
<221> NAME/KEY: MISC_FEATURE
<223> OTHER INFORMATION: XPA.92.042 HV
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(106)
<223> OTHER INFORMATION: H-CDR3

<400> SEQUENCE: 5

Glu Val Gln Leu Val Gln Ser Gly Thr Glu Val Lys Lys Ala Gly Asp
1               5                   10                  15

Ser Leu Lys Ile Ser Cys Lys Gly Ser Gly Tyr Asn Phe Asp Thr Tyr
            20                  25                  30

Trp Ile Gly Trp Val Arg Gln Met Pro Gly Arg Gly Leu Glu Trp Met
        35                  40                  45

Gly Thr Ile Tyr Pro Ala Asp Ser Asp Thr Arg Tyr Ser Pro Ser Phe
    50                  55                  60

```
Gln Gly Gln Val Thr Met Ser Ala Asp Lys Ser Ile Ser Thr Ala Tyr
 65                  70                  75                  80

Leu Gln Trp Gly Ser Leu Arg Ala Ser Asp Thr Ala Met Tyr Tyr Cys
                 85                  90                  95

Ala Arg Phe Ser Ser Ser Ala Tyr Asp Ile Trp Gly Gln Gly Thr Met
            100                 105                 110

Val Thr Val Ser Ser
            115

<210> SEQ ID NO 6
<211> LENGTH: 351
<212> TYPE: DNA
<213> ORGANISM: Homo sapiens
<220> FEATURE:
<221> NAME/KEY: misc_feature
<223> OTHER INFORMATION: XPA.92.042 HV

<400> SEQUENCE: 6
gaggtccagc tggtacagtc tggaacagag gtgaaaaagg ccggggactc tctgaagatt      60
tcctgtaagg gttctggata caactttgac acgtactgga tcggctgggt gcgccagatg     120
cccgggagag gcctggagtg gatgggcacc atctatcctg ctgactctga caccagatat     180
agtccgtcct tccaaggcca ggtcaccatg tcagccgaca gtccatcag caccgcctac     240 ctgcagtggg gcagcctgag ggcctcggac accgccatgt attactgtgc gaggttcagc     300
agctctgcct atgacatttg gggccaaggg acaatggtca ccgtctcttc a              351

<210> SEQ ID NO 7
<211> LENGTH: 121
<212> TYPE: PRT
<213> ORGANISM: Homo sapiens
<220> FEATURE:
<221> NAME/KEY: MISC_FEATURE
<223> OTHER INFORMATION: XPA.92.099 HV
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(110)
<223> OTHER INFORMATION: H-CDR3

<400> SEQUENCE: 7

Gln Val Gln Leu Val Glu Ser Gly Gly Gly Leu Val Lys Pro Gly Arg
 1               5                  10                  15

Ser Leu Arg Leu Ser Cys Ala Ala Ser Gly Phe Thr Phe Asn Arg Tyr
             20                  25                  30

Ala Met Ser Trp Val Arg Gln Ala Pro Gly Lys Gly Leu Glu Trp Val
            35                  40                  45

Ala Met Ile Ser Phe Asp Gly Gly Asn Gln Tyr Tyr Thr Asp Ser Val
        50                  55                  60

Ser Gly Arg Phe Thr Ile Ser Arg Asp Asn Ser Lys Thr Thr Leu Phe
 65                  70                  75                  80

Leu Gln Met Asp Ser Leu Arg Thr Glu Asp Thr Ala Val Tyr Tyr Cys
                 85                  90                  95

Val Arg Ser Pro Ala Gly Asp Trp Val Ala Tyr Phe Asp Tyr Trp Gly
            100                 105                 110
```

```
Gln Gly Thr Leu Val Thr Val Ser Ser
        115                 120
```

<210> SEQ ID NO 8
<211> LENGTH: 363
<212> TYPE: DNA
<213> ORGANISM: Homo sapiens
<220> FEATURE:
<221> NAME/KEY: misc_feature
<223> OTHER INFORMATION: XPA.92.099 HV

<400> SEQUENCE: 8

```
caggtgcagc tggtggagtc tgggggaggc ttggtcaagc ctggagggtc cctgagactc      60
tcctgtgcag cctctggatt caccttcaat agatatgcca tgagctgggt ccgccaggct     120
ccaggcaagg ggctagagtg ggtggcgatg atatcatttg atggaggtaa tcaatattac     180
acagactccg tgagtggccg attcaccatc tccagagaca attccaagac cacgctgttt     240
ctgcaaatgg acagcctgag aactgaggac acggctgtgt attattgtgt gagatccccg     300
gcgggggact gggttgccta ctttgactac tggggccagg gaaccctggt caccgtctcc     360
tca                                                                    363
```

<210> SEQ ID NO 9
<211> LENGTH: 109
<212> TYPE: PRT
<213> ORGANISM: Homo sapiens
<220> FEATURE:
<221> NAME/KEY: MISC_FEATURE
<223> OTHER INFORMATION: XPA.92.019 LV (lambda)
<220> FEATURE:
<221> NAME/KEY: MISC_FEATURE
<222> LOCATION: (26)..(31)
<223> OTHER INFORMATION: L-CDR1
<220> FEATURE:
<221> NAME/KEY: MISC_FEATURE
<222> LOCATION: (49)..(51)
<223> OTHER INFORMATION: L-CDR2
<220> FEATURE:
<221> NAME/KEY: MISC_FEATURE
<222> LOCATION: (88)..(98)
<223> OTHER INFORMATION: L-CDR3

<400> SEQUENCE: 9

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Arg Phe Ala
            20                  25                  30

Tyr Trp Tyr Gln Gln Lys Ala Gly Gln Ala Pro Val Leu Val Ile Tyr
        35                  40                  45

Glu Asp Asn Lys Arg Pro Ser Gly Ile Pro Glu Thr Leu Ser Gly Ser
    50                  55                  60

Ser Ser Gly Thr Thr Ala Thr Leu Thr Ile Ser Gly Ala Gln Glu Glu
65                  70                  75                  80

Asp Glu Ala Asp Tyr Tyr Cys Tyr Ser Thr Asp Asn Thr Gly Gly Leu
                85                  90                  95

Trp Val Phe Gly Gly Gly Thr Lys Leu Thr Val Leu Gly
            100                 105
```

<210> SEQ ID NO 10
<211> LENGTH: 327
<212> TYPE: DNA
<213> ORGANISM: Homo sapiens
<220> FEATURE:
<221> NAME/KEY: misc_feature
<223> OTHER INFORMATION: XPA.92.019 LV (lambda)

<400> SEQUENCE: 10

```
tcctatgagc tgacacagcc accctcggtg tcagtatccc caggacaaac ggccaggatc    60
acctgctctg gagatgcatt gccaaaaaga tttgcttatt ggtaccagca gaaggcaggc   120
caggcccctg tactggtcat ctatgaggac aacaaacgac cctccgggat ccctgagaca   180
ctgtctggct ccagttcagg gacaacggcc accttgacca tcagtggggc ccaggaggag   240
gatgaagctg actactattg ttactccaca gacaacactg tggtctctg ggtgttcggc   300
ggagggacca agctgaccgt cctaggt                                       327
```

<210> SEQ ID NO 11
<211> LENGTH: 109
<212> TYPE: PRT
<213> ORGANISM: Homo sapiens
<220> FEATURE:
<221> NAME/KEY: MISC_FEATURE
<223> OTHER INFORMATION: XPA.92.041 LV (lambda)
<220> FEATURE:
<221> NAME/KEY: MISC_FEATURE
<222> LOCATION: (26)..(31)
<223> OTHER INFORMATION: L-CDR1
<220> FEATURE:
<221> NAME/KEY: MISC_FEATURE
<222> LOCATION: (49)..(51)
<223> OTHER INFORMATION: L-CDR2
<220> FEATURE:
<221> NAME/KEY: MISC_FEATURE
<222> LOCATION: (88)..(98)
<223> OTHER INFORMATION: L-CDR3

<400> SEQUENCE: 11

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Arg Gln Phe Ala
            20                  25                  30

Tyr Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

His Val Phe Gly Gly Gly Thr Gln Leu Thr Val Leu Gly
            100                 105
```

<210> SEQ ID NO 12
<211> LENGTH: 327
<212> TYPE: DNA
<213> ORGANISM: Homo sapiens
<220> FEATURE:
<221> NAME/KEY: misc_feature
<223> OTHER INFORMATION: XPA.92.041 LV (lambda)

<400> SEQUENCE: 12

```
tcctatgagc tgacacagcc accctcggtg tcagtgtccc caggacagac ggccaggatc    60
acctgctctg gagatgcgtt gccaaggcaa tttgcttatt ggtaccagca gaagccaggc   120
caggcccctg tgctggtgat atataaagac actgagaggc cctcagggat ccctgagcga   180
ttctctggct ccagctcagg gacaacagtc acgttgacca tcagtggagt ccaggcagaa   240
```

```
gacgaggctg actattactg tcaatcagca gacagcagtg gtacttatca cgtgtttgga        300
ggaggcaccc agctgaccgt cctaggt                                            327
```

<210> SEQ ID NO 13
<211> LENGTH: 108
<212> TYPE: PRT
<213> ORGANISM: Homo sapiens
<220> FEATURE:
<221> NAME/KEY: MISC_FEATURE
<223> OTHER INFORMATION: XPA.92.042 LV (lambda)
<220> FEATURE:
<221> NAME/KEY: MISC_FEATURE
<222> LOCATION: (26)..(31)
<223> OTHER INFORMATION: L-CDR1
<220> FEATURE:
<221> NAME/KEY: MISC_FEATURE
<222> LOCATION: (49)..(51)
<223> OTHER INFORMATION: L-CDR2
<220> FEATURE:
<221> NAME/KEY: MISC_FEATURE
<222> LOCATION: (88)..(97)
<223> OTHER INFORMATION: L-CDR3

<400> SEQUENCE: 13

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Arg Lys Phe Ala
            20                  25                  30

Tyr Trp Tyr Gln Gln Lys Ser Gly Gln Ala Pro Val Leu Val Ile Tyr
        35                  40                  45

Gln Asp Thr Lys Arg Pro Ser Gly Ile Pro Glu Arg Phe Ser Gly Ser
    50                  55                  60

Ser Ser Gly Thr Thr Val Thr Leu Thr Ile Ser Asp Val Gln Ala Glu
65                  70                  75                  80

Asp Asp Ala Asp Tyr Tyr Cys Gln Ser Ala Asp Arg Ser Asp Ser Tyr
                85                  90                  95

Val Phe Gly Ala Gly Thr Lys Leu Thr Val Leu Gly
            100                 105

<210> SEQ ID NO 14
<211> LENGTH: 324
<212> TYPE: DNA
<213> ORGANISM: Homo sapiens
<220> FEATURE:
<221> NAME/KEY: misc_feature
<223> OTHER INFORMATION: XPA.92.042 LV (lambda)

<400> SEQUENCE: 14

```
tcctatgagc tgacacagcc accctcggtg tcagtgtccc caggacaaac ggccaggatc        60
acctgctctg gagatgcatt gccaagaaaa tttgcttact ggtaccagca gaagtcaggc        120
caggcccctg tcctggtgat atatcaagac actaagaggc cctcagggat ccctgagcga        180
ttctctggct ccagctcagg gacaacagtc acgttgacca tcagtgacgt ccaggcagag        240
gacgacgctg actattattg tcagtcagcc gacagaagtg attcttatgt cttcggagct        300
gggaccaagc tcaccgtcct aggt                                               324
```

<210> SEQ ID NO 15
<211> LENGTH: 109
<212> TYPE: PRT
<213> ORGANISM: Homo sapiens
<220> FEATURE:
<221> NAME/KEY: MISC_FEATURE
<223> OTHER INFORMATION: XPA.92.099 LV (kappa)

```
<220> FEATURE:
<221> NAME/KEY: MISC_FEATURE
<222> LOCATION: (27)..(32)
<223> OTHER INFORMATION: K-CDR1
<220> FEATURE:
<221> NAME/KEY: MISC_FEATURE
<222> LOCATION: (50)..(52)
<223> OTHER INFORMATION: K-CDR2
<220> FEATURE:
<221> NAME/KEY: MISC_FEATURE
<222> LOCATION: (89)..(98)
<223> OTHER INFORMATION: K-CDR3

<400> SEQUENCE: 15

Asp Ile Gln Met Thr Gln Ser Pro Ser Ser Leu Ser Ala Ser Ile Gly
1               5                   10                  15

Asp Arg Val Thr Ile Pro Cys Gln Ala Ser Glu Asp Ile Ser Asn His
            20                  25                  30

Leu Ser Trp Tyr Gln Gln Lys Pro Gly Lys Ala Pro Lys Pro Leu Ile
        35                  40                  45

Phe Asp Ala Ser Asp Leu Glu Thr Gly Val Pro Ser Arg Phe Ser Gly
    50                  55                  60

Ser Gly Ser Gly Thr Asp Phe Ala Leu Thr Ile Ser Ser Leu Arg Pro
65                  70                  75                  80

Asp Asp Phe Ala Thr Tyr Tyr Cys His Gln Tyr His Asp Tyr Pro Ser
                85                  90                  95

Tyr Thr Phe Gly His Gly Thr Lys Leu Glu Ile Lys Arg
            100                 105

<210> SEQ ID NO 16
<211> LENGTH: 327
<212> TYPE: DNA
<213> ORGANISM: Homo sapiens
<220> FEATURE:
<221> NAME/KEY: misc_feature
<223> OTHER INFORMATION: XPA.92.099 LV (kappa)

<400> SEQUENCE: 16
gacatccaga tgacccagtc tccttcctcc ctgtctgctt ctattggaga cagagtcacc      60
atcccctgcc aggcgagtga ggacattagt aatcatttaa gttggtatca gcagaaacca    120
gggaaagccc ctaaacccct gatcttcgat gcatccgatt tggaaacagg ggtcccatca    180
aggttcagtg gaagtggatc tgggacagat tttgctctca ccatcagcag cctgcggcct    240
gatgattttg caacttatta ctgccaccag tatcatgatt atccctcgta cacttttggc    300
cacgggacca agctggagat caaacgt                                         327

<210> SEQ ID NO 17
<211> LENGTH: 8
<212> TYPE: PRT
<213> ORGANISM: Homo sapiens
<220> FEATURE:
<221> NAME/KEY: MISC_FEATURE
<223> OTHER INFORMATION: XPA.92.019 HV H-CDR1

<400> SEQUENCE: 17

Gly Phe Thr Phe Ser Tyr Tyr Gly
1               5

<210> SEQ ID NO 18
<211> LENGTH: 8
<212> TYPE: PRT
<213> ORGANISM: Homo sapiens
<220> FEATURE:
```

```
<221> NAME/KEY: MISC_FEATURE
<223> OTHER INFORMATION: XPA.92.019 HV H-CDR2

<400> SEQUENCE: 18

Ile Ser Asn Asp Gly Ser Asn Lys
1               5

<210> SEQ ID NO 19
<211> LENGTH: 12
<212> TYPE: PRT
<213> ORGANISM: Homo sapiens
<220> FEATURE:
<221> NAME/KEY: MISC_FEATURE
<223> OTHER INFORMATION: XPA.92.019 HV H-CDR3

<400> SEQUENCE: 19

Arg Pro Glu Asp Thr Ala Val Tyr Tyr Cys Ala Thr
1               5                   10

<210> SEQ ID NO 20
<211> LENGTH: 8
<212> TYPE: PRT
<213> ORGANISM: Homo sapiens
<220> FEATURE:
<221> NAME/KEY: MISC_FEATURE
<223> OTHER INFORMATION: XPA.92.041 HV H-CDR1

<400> SEQUENCE: 20

Gly Tyr Asn Phe Asp Thr Tyr Trp
1               5

<210> SEQ ID NO 21
<211> LENGTH: 8
<212> TYPE: PRT
<213> ORGANISM: Homo sapiens
<220> FEATURE:
<221> NAME/KEY: MISC_FEATURE
<223> OTHER INFORMATION: XPA.92.041 HV H-CDR2

<400> SEQUENCE: 21

Ile Tyr Pro Ala Asp Ser Asp Thr
1               5

<210> SEQ ID NO 22
<211> LENGTH: 10
<212> TYPE: PRT
<213> ORGANISM: Homo sapiens
<220> FEATURE:
<221> NAME/KEY: MISC_FEATURE
<223> OTHER INFORMATION: XPA.92.041 HV H-CDR3

<400> SEQUENCE: 22

Ala Arg Phe Ser Ser Ser Ala Tyr Asp Ile
1               5                   10

<210> SEQ ID NO 23
<211> LENGTH: 8
<212> TYPE: PRT
<213> ORGANISM: Homo sapiens
<220> FEATURE:
<221> NAME/KEY: MISC_FEATURE
<223> OTHER INFORMATION: XPA.92.042 HV H-CDR1

<400> SEQUENCE: 23

Gly Tyr Asn Phe Asp Thr Tyr Trp
1               5
```

```
<210> SEQ ID NO 24
<211> LENGTH: 8
<212> TYPE: PRT
<213> ORGANISM: Homo sapiens
<220> FEATURE:
<221> NAME/KEY: MISC_FEATURE
<223> OTHER INFORMATION: XPA.92.042 HV H-CDR2

<400> SEQUENCE: 24

Ile Tyr Pro Ala Asp Ser Asp Thr
1               5

<210> SEQ ID NO 25
<211> LENGTH: 10
<212> TYPE: PRT
<213> ORGANISM: Homo sapiens
<220> FEATURE:
<221> NAME/KEY: MISC_FEATURE
<223> OTHER INFORMATION: XPA.92.042 HV H-CDR3

<400> SEQUENCE: 25

Ser Ser Ala Tyr Asp Ile Ala Arg Phe Ser
1               5                   10

<210> SEQ ID NO 26
<211> LENGTH: 8
<212> TYPE: PRT
<213> ORGANISM: Homo sapiens
<220> FEATURE:
<221> NAME/KEY: MISC_FEATURE
<223> OTHER INFORMATION: XPA.92.099 HV H-CDR1

<400> SEQUENCE: 26

Gly Phe Thr Phe Asn Arg Tyr Ala
1               5

<210> SEQ ID NO 27
<211> LENGTH: 8
<212> TYPE: PRT
<213> ORGANISM: Homo sapiens
<220> FEATURE:
<221> NAME/KEY: MISC_FEATURE
<223> OTHER INFORMATION: XPA.92.099 HV H-CDR2

<400> SEQUENCE: 27

Ile Ser Phe Asp Gly Gly Asn Gln
1               5

<210> SEQ ID NO 28
<211> LENGTH: 14
<212> TYPE: PRT
<213> ORGANISM: Homo sapiens
<220> FEATURE:
<221> NAME/KEY: MISC_FEATURE
<223> OTHER INFORMATION: XPA.92.099 HV H-CDR3

<400> SEQUENCE: 28

Val Arg Ser Pro Ala Gly Asp Trp Val Ala Tyr Phe Asp Tyr
1               5                   10

<210> SEQ ID NO 29
<211> LENGTH: 6
<212> TYPE: PRT
<213> ORGANISM: Homo sapiens
<220> FEATURE:
<221> NAME/KEY: MISC_FEATURE
<223> OTHER INFORMATION: XPA.92.019 LV (lambda) L-CDR1

<400> SEQUENCE: 29
```

```
Ala Leu Pro Lys Arg Phe
1               5

<210> SEQ ID NO 30
<211> LENGTH: 3
<212> TYPE: PRT
<213> ORGANISM: Homo sapiens
<220> FEATURE:
<221> NAME/KEY: MISC_FEATURE
<223> OTHER INFORMATION: XPA.92.019 LV (lambda) L-CDR2

<400> SEQUENCE: 30

Glu Asp Asn
1

<210> SEQ ID NO 31
<211> LENGTH: 11
<212> TYPE: PRT
<213> ORGANISM: Homo sapiens
<220> FEATURE:
<221> NAME/KEY: MISC_FEATURE
<223> OTHER INFORMATION: XPA.92.019 LV (lambda) L-CDR3

<400> SEQUENCE: 31

Tyr Ser Thr Asp Asn Thr Gly Gly Leu Trp Val
1               5                   10

<210> SEQ ID NO 32
<211> LENGTH: 6
<212> TYPE: PRT
<213> ORGANISM: Homo sapiens
<220> FEATURE:
<221> NAME/KEY: MISC_FEATURE
<223> OTHER INFORMATION: XPA.92.041 LV (lambda) L-CDR1

<400> SEQUENCE: 32

Ala Leu Pro Arg Gln Phe
1               5

<210> SEQ ID NO 33
<211> LENGTH: 3
<212> TYPE: PRT
<213> ORGANISM: Homo sapiens
<220> FEATURE:
<221> NAME/KEY: MISC_FEATURE
<223> OTHER INFORMATION: XPA.92.041 LV (lambda) L-CDR2

<400> SEQUENCE: 33

Lys Asp Thr
1

<210> SEQ ID NO 34
<211> LENGTH: 10
<212> TYPE: PRT
<213> ORGANISM: Homo sapiens
<220> FEATURE:
<221> NAME/KEY: MISC_FEATURE
<223> OTHER INFORMATION: XPA.92.041 LV (lambda) L-CDR3

<400> SEQUENCE: 34

Asp Ser Ser Gly Thr Tyr His Gln Ser Ala
1               5                   10

<210> SEQ ID NO 35
<211> LENGTH: 6
<212> TYPE: PRT
<213> ORGANISM: Homo sapiens
```

```
<220> FEATURE:
<221> NAME/KEY: MISC_FEATURE
<223> OTHER INFORMATION: XPA.92.042 LV (lambda) L-CDR1

<400> SEQUENCE: 35

Ala Leu Pro Arg Lys Phe
1               5

<210> SEQ ID NO 36
<211> LENGTH: 3
<212> TYPE: PRT
<213> ORGANISM: Homo sapiens
<220> FEATURE:
<221> NAME/KEY: MISC_FEATURE
<223> OTHER INFORMATION: XPA.92.042 LV (lambda) L-CDR2

<400> SEQUENCE: 36

Gln Asp Thr
1

<210> SEQ ID NO 37
<211> LENGTH: 10
<212> TYPE: PRT
<213> ORGANISM: Homo sapiens
<220> FEATURE:
<221> NAME/KEY: MISC_FEATURE
<223> OTHER INFORMATION: XPA.92.042 LV (lambda) L-CDR3

<400> SEQUENCE: 37

Gln Ser Ala Asp Arg Ser Asp Ser Tyr Val
1               5                   10

<210> SEQ ID NO 38
<211> LENGTH: 6
<212> TYPE: PRT
<213> ORGANISM: Homo sapiens
<220> FEATURE:
<221> NAME/KEY: MISC_FEATURE
<223> OTHER INFORMATION: XPA.92.099 LV (kappa) K-CDR1

<400> SEQUENCE: 38

Glu Asp Ile Ser Asn His
1               5

<210> SEQ ID NO 39
<211> LENGTH: 3
<212> TYPE: PRT
<213> ORGANISM: Homo sapiens
<220> FEATURE:
<221> NAME/KEY: MISC_FEATURE
<223> OTHER INFORMATION: XPA.92.099 LV (kappa) K-CDR2

<400> SEQUENCE: 39

Asp Ala Ser
1

<210> SEQ ID NO 40
<211> LENGTH: 10
<212> TYPE: PRT
<213> ORGANISM: Homo sapiens
<220> FEATURE:
<221> NAME/KEY: MISC_FEATURE
<223> OTHER INFORMATION: XPA.92.099 LV (kappa) K-CDR3

<400> SEQUENCE: 40

His Gln Tyr His Asp Tyr Pro Ser Tyr Thr
1               5                   10
```

<210> SEQ ID NO 41
<211> LENGTH: 12
<212> TYPE: PRT
<213> ORGANISM: Homo sapiens

<400> SEQUENCE: 41

Ala Thr Pro Tyr Tyr Asp Ser Ser Gly Leu Asp Tyr
1               5                   10

<210> SEQ ID NO 42
<211> LENGTH: 108
<212> TYPE: PRT
<213> ORGANISM: Homo Sapiens

<400> SEQUENCE: 42

Ala Ile Leu Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro Leu
                85                  90                  95

Thr Phe Gly Gly Gly Thr Lys Val Asp Ile Lys Arg
            100                 105

<210> SEQ ID NO 43
<211> LENGTH: 107
<212> TYPE: PRT
<213> ORGANISM: Homo Sapiens

<400> SEQUENCE: 43

Asp Ile Leu Met Thr Gln Ser Pro Ser Phe Leu Ser Ala Ser Val Gly
1               5                   10                  15

Asp Arg Val Thr Ile Thr Cys Arg Ala Ser Gln Gly Ile Asn Ser Phe
            20                  25                  30

Leu Val Trp Tyr Gln Gln Lys Pro Gly Lys Ala Pro Lys Leu Leu Ile
        35                  40                  45

Tyr Asp Ala Ser Asn Leu Gln Asp Gly Val Pro Ser Arg Phe Ser Gly
    50                  55                  60

Ser Gly Ser Arg Thr Asp Phe Thr Leu Thr Ile Arg Ser Leu Gln Pro
65                  70                  75                  80

Glu Asp Phe Ala Thr Tyr Tyr Cys Leu Gln Asp Ser Tyr Pro Leu Thr
                85                  90                  95

Phe Gly Gln Gly Thr Lys Val Glu Ile Lys Arg
            100                 105

<210> SEQ ID NO 44
<211> LENGTH: 108
<212> TYPE: PRT
<213> ORGANISM: Homo Sapiens

<400> SEQUENCE: 44

Asp Ile Gln Met Thr Gln Ser Pro Ser Ser Leu Tyr Ala Ser Val Gly
1               5                   10                  15

```
Asp Arg Val Thr Ile Thr Cys Arg Ala Ser Leu Gly Ile Arg Ser Ala
            20                  25                  30

Leu Ala Trp Tyr Gln Gln Lys Pro Gly Lys Ala Pro Lys Leu Leu Ile
        35                  40                  45

Ser Asp Ala Ser Asp Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Phe Asn Asn Phe Pro Ile
                85                  90                  95

Thr Phe Gly Gln Gly Thr Arg Leu Glu Ile Lys Arg
            100                 105

<210> SEQ ID NO 45
<211> LENGTH: 108
<212> TYPE: PRT
<213> ORGANISM: Homo Sapiens

<400> SEQUENCE: 45

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Ile Ser Ser Trp
            20                  25                  30

Leu Ala Trp Tyr Gln Gln Lys Pro Gly Lys Ala Pro Lys Pro Leu Ile
        35                  40                  45

Tyr Asp Ala Ser Asp Leu Glu Ala Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Ser Ala Thr Tyr Tyr Cys Gln Gln Tyr Asn Glu Tyr Pro Phe
                85                  90                  95

Thr Phe Gly Gln Gly Thr Lys Leu Glu Ile Lys Arg
            100                 105

<210> SEQ ID NO 46
<211> LENGTH: 108
<212> TYPE: PRT
<213> ORGANISM: Homo Sapiens

<400> SEQUENCE: 46

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln His Ile Thr Asn Tyr
            20                  25                  30

Leu Ser Trp Tyr Gln His Lys Pro Gly Arg Ala Pro Arg Leu Leu Ile
        35                  40                  45

Tyr Asp Ala Ser Asp Leu Glu Thr Gly Val Pro Ser Arg Phe Ser Gly
50                  55                  60

Ser Gly Ser Gly Thr Asp Phe Thr Leu Ser Ile Ser Ser Leu Gln Pro
65                  70                  75                  80

Glu Asp Ile Ala Thr Tyr Tyr Cys Gln His Tyr Asp Asn Leu Pro Tyr
                85                  90                  95

Thr Phe Gly Gln Gly Thr Lys Val Glu Ile Lys Arg
            100                 105

<210> SEQ ID NO 47
```

```
<211> LENGTH: 108
<212> TYPE: PRT
<213> ORGANISM: Homo Sapiens

<400> SEQUENCE: 47

Ala Ile Arg Met Thr Gln Ser Pro Ser Leu Ser Ala Ser Val Gly
1               5                   10                  15

Asp Arg Val Thr Ile Thr Cys Gln Ala Ser Gln His Ile Thr Asn Tyr
            20                  25                  30

Leu Ser Trp Tyr Gln His Lys Pro Gly Arg Ala Pro Arg Leu Leu Ile
        35                  40                  45

Tyr Asp Ala Ser Asp Leu Glu Thr Gly Val Pro Ser Arg Phe Ser Gly
    50                  55                  60

Ser Gly Ser Gly Thr Asp Phe Thr Leu Ser Ile Ser Ser Leu Gln Pro
65                  70                  75                  80

Glu Asp Ile Ala Thr Tyr Tyr Cys Gln His Tyr Asp Asn Leu Pro Tyr
                85                  90                  95

Thr Phe Gly Gln Gly Thr Lys Val Glu Ile Lys Arg
            100                 105

<210> SEQ ID NO 48
<211> LENGTH: 108
<212> TYPE: PRT
<213> ORGANISM: Homo Sapiens

<400> SEQUENCE: 48

Asp Ile Gln Met Thr Gln Ser Pro Ser Leu Ser Ala Ser Val Gly
1               5                   10                  15

Asp Arg Val Thr Ile Thr Cys Gln Ala Ser Arg His Ile Ser Asp Tyr
            20                  25                  30

Leu Ser Trp Tyr Gln Gln Lys Pro Gly Lys Ala Pro Lys Leu Leu Ile
        35                  40                  45

Tyr Asp Ala Tyr Asp Leu Glu Pro Gly Val Pro Ser Arg Phe Ser Gly
    50                  55                  60

Ser Lys Ser Gly Thr His Phe Thr Phe Thr Ile Ser Ser Leu Gln Pro
65                  70                  75                  80

Glu Asp Phe Ala Thr Tyr Tyr Cys Gln Gln Tyr Asp Asn Phe Pro Phe
                85                  90                  95

Thr Phe Gly Pro Gly Thr Lys Val Glu Ile Lys Arg
            100                 105

<210> SEQ ID NO 49
<211> LENGTH: 108
<212> TYPE: PRT
<213> ORGANISM: Homo Sapiens

<400> SEQUENCE: 49

Asp Ile Gln Met Thr Gln Ser Pro Ser Leu Ser Ala Ser Val Gly
1               5                   10                  15

Asp Arg Val Thr Ile Thr Cys Gln Ala Ser His His Ile Ser Asp Tyr
            20                  25                  30

Leu Asn Trp Tyr Gln Gln Lys Pro Gly Lys Ala Pro Lys Leu Leu Ile
        35                  40                  45

Phe Asp Val Ser Tyr Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Leu Gln Asp Tyr Asn Tyr Pro Leu
                85                  90                  95

Thr Phe Gly Gln Gly Thr Lys Val Glu Ile Lys Arg
            100                 105

<210> SEQ ID NO 50
<211> LENGTH: 150
<212> TYPE: PRT
<213> ORGANISM: Mus Musculus

<400> SEQUENCE: 50

Met Ala Pro Thr Ser Ser Pro Thr Ser Ser Pro Thr Ser Ser Ser Thr
1               5                   10                  15

Ala Glu Ala Gln Gln Gln Gln Gln Gln His Leu Glu Gln Leu
            20                  25                  30

Leu Met Asp Leu Gln Glu Leu Leu Ser Arg Met Glu Asn Tyr Arg Asn
            35                  40                  45

Leu Lys Leu Pro Arg Met Leu Thr Phe Lys Phe Tyr Leu Pro Lys Gln
50                  55                  60

Ala Thr Glu Leu Lys Asp Leu Gln Cys Leu Glu Asp Glu Leu Gly Pro
65                  70                  75                  80

Leu Arg His Val Leu Asp Leu Thr Gln Ser Lys Ser Phe Gln Leu Glu
                85                  90                  95

Asp Ala Glu Asn Phe Ile Ser Asn Ile Arg Val Thr Val Val Lys Leu
            100                 105                 110

Lys Gly Ser Asp Asn Thr Phe Glu Cys Gln Phe Asp Asp Glu Ser Ala
            115                 120                 125

Thr Val Val Asp Phe Leu Arg Arg Trp Ile Ala Phe Cys Gln Ser Ile
            130                 135                 140

Ile Ser Thr Ser Pro Gln
145                 150

<210> SEQ ID NO 51
<211> LENGTH: 155
<212> TYPE: PRT
<213> ORGANISM: Rattus norvegicus

<400> SEQUENCE: 51

Met Tyr Ser Met Gln Leu Ala Ser Cys Val Ala Leu Thr Leu Val Leu
1               5                   10                  15

Leu Val Asn Ser Ala Pro Thr Ser Ser Pro Ala Lys Glu Thr Gln Gln
            20                  25                  30

His Leu Glu Gln Leu Leu Leu Asp Leu Gln Val Leu Leu Arg Gly Ile
            35                  40                  45

Asp Asn Tyr Lys Asn Leu Lys Leu Pro Met Met Leu Thr Phe Lys Phe
50                  55                  60

Tyr Leu Pro Lys Gln Ala Thr Glu Leu Lys His Leu Gln Cys Leu Glu
65                  70                  75                  80

Asn Glu Leu Gly Ala Leu Gln Arg Val Leu Asp Leu Thr Gln Ser Lys
            85                  90                  95

Ser Phe His Leu Glu Asp Ala Gly Asn Phe Ile Ser Asn Ile Arg Val
            100                 105                 110

Thr Val Val Lys Leu Lys Gly Ser Glu Asn Lys Phe Glu Cys Gln Phe
            115                 120                 125

Asp Asp Glu Pro Ala Thr Val Val Glu Phe Leu Arg Arg Trp Ile Ala
            130                 135                 140
```

Ile Cys Gln Ser Ile Ile Ser Thr Met Thr Gln
145                 150                 155

<210> SEQ ID NO 52
<211> LENGTH: 153
<212> TYPE: PRT
<213> ORGANISM: Homo Sapiens

<400> SEQUENCE: 52

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 53
<211> LENGTH: 153
<212> TYPE: PRT
<213> ORGANISM: Oryctolagus cuniculus

<400> SEQUENCE: 53

Met Tyr Lys Val Gln Leu Leu Ser Cys Ile Ala Leu Thr Leu Ala Leu
1               5                   10                  15

Leu Thr Ser Ser Ala Pro Thr Ser Ser Ser Thr Lys Glu Thr Gln Glu
            20                  25                  30

Gln Leu Asp Gln Leu Leu Leu Asp Leu Gln Val Leu Leu Lys Gly Val
        35                  40                  45

Asn Asp Tyr Lys Asn Ser Lys Leu Ser Arg Met Leu Thr Phe Lys Phe
    50                  55                  60

Tyr Met Pro Lys Lys Val Thr Glu Leu Lys His Leu Gln Cys Leu Glu
65                  70                  75                  80

Glu Glu Leu Lys Pro Leu Glu Glu Val Leu Asn Leu Ala Gln Gly Lys
                85                  90                  95

Asn Ser His Gly Gly Asn Thr Arg Glu Ser Ile Ser Asn Ile Asn Val
            100                 105                 110

Thr Val Leu Lys Leu Lys Gly Ser Glu Thr Phe Met Cys Glu Tyr Asp
        115                 120                 125

Glu Thr Val Thr Ile Val Glu Phe Leu Asn Arg Trp Ile Thr Phe Cys
    130                 135                 140

Gln Ser Ile Ile Ser Ala Ser Ser Ser
145                 150

```
<210> SEQ ID NO 54
<211> LENGTH: 154
<212> TYPE: PRT
<213> ORGANISM: Sus scrofa

<400> SEQUENCE: 54

Met Tyr Lys Met Gln Leu Leu Cys Cys Ile Ala Leu Thr Leu Ala Leu
1               5                   10                  15

Met Ala Asn Gly Ala Pro Thr Ser Ser Ser Thr Lys Asn Thr Lys Lys
            20                  25                  30

Gln Leu Glu Pro Leu Leu Leu Asp Leu Gln Leu Leu Leu Lys Glu Val
        35                  40                  45

Lys Asn Tyr Glu Asn Ala Asp Leu Ser Arg Met Leu Thr Phe Lys Phe
    50                  55                  60

Tyr Met Pro Lys Gln Ala Thr Glu Leu Lys His Leu Gln Cys Leu Val
65                  70                  75                  80

Glu Glu Leu Lys Ala Leu Glu Gly Val Leu Asn Leu Gly Gln Ser Lys
                85                  90                  95

Asn Ser Asp Ser Ala Asn Ile Lys Glu Ser Met Asn Asn Ile Asn Val
            100                 105                 110

Thr Val Leu Glu Leu Lys Gly Ser Glu Thr Ser Phe Lys Cys Glu Tyr
        115                 120                 125

Asp Asp Glu Thr Val Thr Ala Val Glu Phe Leu Asn Lys Trp Ile Thr
    130                 135                 140

Phe Cys Gln Ser Ile Tyr Ser Thr Leu Thr
145                 150
```